(12) United States Patent
Laux et al.

(10) Patent No.: US 10,787,667 B2
(45) Date of Patent: *Sep. 29, 2020

(54) ANTI-CONNEXIN COMPOUNDS TARGETED TO CONNEXINS AND METHODS OF USE THEREOF

(71) Applicant: OCUNEXUS THERAPEUTICS, INC., San Diego, CA (US)

(72) Inventors: Wilda Laux, Mangere (NZ); Colin Richard Green, Auckland (NZ)

(73) Assignee: OCUNEXUS THERAPEUTICS, INC., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/680,298

(22) Filed: Nov. 11, 2019

(65) Prior Publication Data

US 2020/0063136 A1 Feb. 27, 2020

Related U.S. Application Data

(60) Continuation of application No. 16/241,943, filed on Jan. 7, 2019, now Pat. No. 10,472,632, which is a division of application No. 14/467,978, filed on Aug. 25, 2014, now Pat. No. 10,174,316, which is a division of application No. 13/230,744, filed on Sep. 12, 2011, now Pat. No. 8,815,819, which is a division of application No. 10/581,813, filed as application No. PCT/IB2004/004431 on Dec. 3, 2004, now Pat. No. 8,034,789.

(30) Foreign Application Priority Data

Dec. 3, 2003 (NZ) ........................................ 529936

(51) Int. Cl.

| C12N 15/113 | (2010.01) |
| C12N 15/11 | (2006.01) |
| A61K 31/7105 | (2006.01) |
| A61K 31/711 | (2006.01) |
| C12Q 1/68 | (2018.01) |

(52) U.S. Cl.
CPC .......... *C12N 15/113* (2013.01); *A61K 31/711* (2013.01); *A61K 31/7105* (2013.01); *C12N 15/111* (2013.01); *C12N 15/1138* (2013.01); *C12N 2310/11* (2013.01); *C12N 2310/12* (2013.01); *C12N 2310/315* (2013.01); *C12N 2320/31* (2013.01); *Y02P 20/582* (2015.11)

(58) Field of Classification Search
None
See application file for complete search history.

(56) References Cited

U.S. PATENT DOCUMENTS

| 7,098,190 B1 | 8/2006 | Becker et al. |
| 7,615,540 B2 | 11/2009 | Green et al. |
| 7,879,811 B2 | 2/2011 | Green et al. |
| 7,902,164 B2* | 3/2011 | Green ................... C12N 15/111 435/375 |
| 8,034,789 B2 | 10/2011 | Laux et al. |
| 2007/0060538 A1 | 3/2007 | Becker et al. |
| 2007/0072819 A1 | 3/2007 | Becker et al. |
| 2007/0072820 A1 | 3/2007 | Becker et al. |
| 2008/0221051 A1 | 9/2008 | Becker et al. |
| 2008/0249041 A1 | 10/2008 | Becker et al. |

FOREIGN PATENT DOCUMENTS

| CN | 1347902 A | 5/2002 |
| KR | 10-2006-7013276 | 1/2014 |
| WO | WO-1996-19194 | 6/1996 |
| WO | WO-1998-24797 | 6/1998 |
| WO | WO-2000-044409 | 8/2000 |

OTHER PUBLICATIONS

Agrawal, "Antisense oligonucleotides; towards clinical trials." *TIBTECH*, 1996, 14:376-387.
Baldwin et al., "Growth factors in corneal wound healing following refractive surgery: A Review," *ACTA Ophthalmologica Scandinavica*, 2002, 80(3):238-247.
Becker et al., "Connexin α1 and cell proliferation in the developing chick retina," *Experimental Neurology*, Apr. 1999, 156(2):326-332.
Branch, "A good antisense molecule is hard to find," *TIBS*, Feb. 1998, 45-50.
Bregman et al., "Transplants and Neurotrophic Factors Prevent Atrophy of Mature CNS Neurons after Spinal Cord Injury," *Experimental Neurology*, 1998, 149(1):13-27.
Calabrese et al., "Connexin 36 controls synchronization of Ca2+ oscillations and insulin secretion in MIN6 cells," *Diabetes*, 2003, 52(2):417-424.
Davis et al., "Modulation of Connexin43 Expression: Effects on Cellular Coupling," *Journal of Cardiovascular Electrophysiology*, Feb. 1995, 6(2):103-114.
Franteseva et al., "Ischemia-Induced Brain Damage Depends on Specific Gap-Junctional coupling," *Journal of Cerebral Blood Flow and Metabolism*, Apr. 2002, 22(4):453-462.
Goliger et al., "Wounding Alters Epidermal Connexin Expression and Gap Junction-Mediated Intercellular Communication," *Molecular Biology of the Cell*, 1995, 6:1491-1501.
Grazul-Bilska et al., "Transfection of Bovine Luteal Cells With Gap Junctional Protein Connexin 43 (Cx43) Antisense Oligonucleotide Affects Progesterone Secretion," 34th Annual Meeting of the Society for the Study of Reproduction, Aug. 8-11, 1998, College Station, TX, *Biology of Reproduction*, 1998, 58(1):78.

(Continued)

*Primary Examiner* — Sean McGarry
(74) *Attorney, Agent, or Firm* — Duane Morris LLP

(57) ABSTRACT

Methods and compositions for modulating the activities of connexins are provided, including, for example, for use in post-surgical, trauma, or tissue engineering applications. These compounds and methods can be used therapeutically, for example, to reduce the severity of adverse effects associated diseases and disorders where localized disruption in direct cell-cell communication is desirable.

16 Claims, 12 Drawing Sheets

Specification includes a Sequence Listing.

(56) References Cited

OTHER PUBLICATIONS

Green et al., "Spatiotemporal depletion of connexins using antisense oligonucleotides: Techniques in the study of gap junctions," *Methods in Molecular Biology: Connexin Methods and Protocols*, R. Bruzzone et al., eds., 2001, 154:175-185.
Haopeng et al., "Experimental study on spinal cord injury treated with the combination of fetal spinal cord transplantation and methylprednisolone," Journal of Xi'an Medical University, English Edition, 2001, 13(2):138-141 (abstract), 1 page.
Hodgins, "Connecting Wounds with Connexins," *The Journal of Investigative Dermatology*, 2004, 122(5):ix-x.
Jen et al., "Suppression of Gene Expression by Targeted Disruption of Messenger RNA: Available Options and Current Strategies," *Stem Cells*, 2000, 18:307-319.
Jin et al., "Combination of fetal tissue transplantation and gene therapy to promote spinal cord regeneration," Society for Neuroscience, 2003, Presented on Nov. 9, 2003 in New Orleans, LA (abstract), 2 pages.
Le Gurun et al., "Connexin-36 contributes to control function of insulin-producing cells," *Journal of Biological Chemistry*, 2003, 278(39):37690-37697.
Moore et al., "Selective block of gap junction channel expression with connexin-specific antisense oligodeoxynucleotides," *American Journal of Physiology*, Nov. 1994, 265(1):C1371-C1388.
Onifer et al., "Combining methylprednisolone, peripheral nerves, FGF1, fibrin, and vertebral wiring for spinal cord repair," Society for Neuroscience, 1999, 25(1-2):492 (abstract), 2 pages.
Qiu et al., "Targeting connexin43 expression accelerates the rate of wound repair," *Current Biology*, Sep. 30, 2003, 13(19):1967-1703.
Ratkay-Traub et al., "Regeneration of rabbit cornea following excimer laser photorefractive keratectomy; a study on gap junctions, epithelial junctions and epidermal growth factor receptor expression in correlation with cell proliferation," *Experimental Eye Research*, Sep. 2001, 73(3):291-302.
Rozental et al., "Stable Transfection With Connexin43 Inhibits Neuronal Differentiation of PC12 Cells," *Society for Neuroscience Abstracts*, Society for Neuroscience, Oct. 1997, 25:22.
Ruch et al., "Inhibition of Gap Junctional Intercellular Communication and Enhancement of Growth in BALBk 3T3 Cells Treated With Connexin43 Antisense Oligonucleotides," *Molecular Carcinogenesis*, 1995, 14:269-274.
Santoro et al., "A General Purpose RNA-Cleaving DNA Enzyme," *Proc. Natl. Acad. Sci. USA*, Apr. 1997, 94:4262-4266.
Sohl et al., "The murine gap junction gene connexin36 is highly expressed in mouse retina and regulated during brain development," *FEBS Letters*, May 1998, 428(1-2):27-31.
Willecke et al. "Structural and functional diversity of connexin genes in the mouse and human genome," *Biological Chemistry*, May 2002, 383(5):725-737.
International Search Report dated Jun. 19, 2000, from International Patent Application No. PCT/GB00/00238, 5 pages.
Extended Search Report dated Dec. 19, 2005, from corresponding European Patent Application No. 05016736.0, 11 pages.
International Search Report dated Jan. 3, 2006, from International Patent Application No. PCT/IB2004/004431, 7 pages.
Examination Report dated Aug. 30, 2006, from corresponding European Patent Application No. 05016736.0, 7 pages.
Office Action dated Dec. 12, 2011, from corresponding Indian Patent Application No. 1827/KOLNP/2006, 1 page.
Notice of Reasons for Rejection dated Apr. 20, 2012, from corresponding Japanese Patent Application No. 2006-542058, 12 total pages.
Partial Search Report dated Jul. 24, 2012, from corresponding European Patent Application No. 10015438.4, 7 pages.
Notice of Restriction Requirement dated Jul. 30, 2012, from corresponding Canadian Patent Application No. 2,547,780, 3 pages.
Office Action dated Aug. 6, 2012, from corresponding Chinese Patent Application No. 200480041251.9, 7 total pages.
Examination Report dated Aug. 17, 2012, from corresponding Singapore Patent Application No. 200603748-5, 10 pages.
Extended Search Report dated Oct. 24, 2012, from corresponding European Patent Application No. 10015438.4, 14 pages.
Corrected Partial Search Report dated Dec. 21, 2012, from corresponding European Patent Application No. 10015439.2, 13 pages.
Notice of Final Rejection dated May 24, 2013, from corresponding Japanese Patent Application No. 2006-542058, 4 pages.
Examiner's Report dated Oct. 3, 2013, from corresponding Canadian Patent Application No. 2,547,780, 2 pages.
Office Action dated Jan. 30, 2014, from corresponding Chinese Patent Application No. 201310098015.1, 14 total pages.
O'Carroll, Simon J., et al. "Connexin43 mimetic peptides reduce swelling, astrogliosis, and neuronal cell death after spinal cord injury." Cell Communication & Adhesion 15.1-2 (2008): 27-42.
Office Action dated Dec. 29, 2014, from related Chinese Application No. 201310098015.1, 10 total pages.

* cited by examiner

C　　　　　　D

ANTI-CONNEXIN COMPOUNDS TARGETED TO CONNEXINS AND METHODS OF USE THEREOF

RELATED PATENT APPLICATIONS

This application is a Continuation Application of U.S. application Ser. No. 16/241,943 filed Jan. 7, 2019, which is a Divisional Application of U.S. application Ser. No. 14/467,978 entitled "ANTI-CONNEXIN COMPOUNDS TARGETED TO CONNEXINS AND METHODS OF USE THEREOF," filed on Aug. 25, 2014, which is a Divisional Application of U.S. application Ser. No. 13/230,744 entitled "ANTISENSE COMPOUNDS TARGETED TO CONNEXINS AND METHODS OF USE THEREOF," filed on Sep. 12, 2011, which is a Divisional Application of U.S. application Ser. No. 10/581,813, entitled "ANTISENSE COMPOUNDS TARGETED TO CONNEXINS AND METHODS OF USE THEREOF," filed on Jan. 29, 2007, which is the National Stage Application under 35 U.S.C. § 371 of International Application No. PCT/IB2004/004431, entitled "ANTISENSE COMPOUNDS TARGETED TO CONNEXINS AND METHODS OF USE THEREOF," filed on Dec. 3, 2004, which claims the benefit of New Zealand Application No. 529936, entitled "TISSUE ENGINEERING OR REMODELING," filed on Dec. 3, 2003, each of which are incorporated herein by reference in their entirety.

TECHNICAL FIELD

The present disclosure relates to and describes agents, compositions and methods of using compounds for modulation of gap-junction-associated protein expression. These agents, compositions, and methods are useful, for example, for tissue engineering in vivo and in vitro, including for example in the skin, in corneal tissue, and conjunction with surgical procedures of the eye.

BACKGROUND

Tissue or organ failure due to illness or injury is a major health problem worldwide with little option for full recovery other than organ or tissue transplantation. However, problems finding a suitable donor mean that this option is not available to the majority of patients. tissue engineering or remodeling whereby synthetic or semi synthetic tissue or organ mimics that are either fully functional or which are grown in a desired functionality is currently being investigated as replacements.

One area in particular that this technology is becoming increasingly important is in the cornea of the eye. Corneal transplantation is the most common form of solid organ transplant performed worldwide. Each year around 80,000 are performed in the USA and the UK alone. The prevalence of refractive surgery for correction of myopia such as photorefractive keratectomy (PRK) and laser in situ keratomileusis (LASIK) has led to shortage of suitable cornea for transplant for tissue reconstruction after surgery or disease processes and for tissue manipulation in vivo to engineer changes. In addition, approximately 5% of patients undergoing laser surgery experience unexpected outcomes.

The cornea is a transparent tissue that comprises the central one sixth of the outer tunic of the eye. Its unified structure and function provide the eye with a clear refractive interface, tensile strength, and protection from external factors. The cornea is built from three different main layers of cells: the epithelium, the stroma, and the endothelium (Pepose, J. S. et al., "The cornea; Adler's Physiology of the eye: Clinical application", $9^{th}$ ed. St. Louis: Mosby Year Book, 1992, 29-47; Spencer, W. H., "The cornea; Ophthalmic Pathology: an atlas and textbook", $4^{th}$ ed., Philadelphia: W. B. Saunders Co., 1996, 157-65). In addition, the Descemet's membrane, the Bowman's layer, and the basement membrane are structures that are derived in some ways from one of these main cellular layers.

The corneal epithelium is the layer in direct contact with the external environment. It is a stratified squamous, non-keratinized structure with a thickness ranging from 40 to 100 m, in rats and in humans, respectively. It is comprised of a superficial zone, usually formed by two to three layers of flat squamous cells; a middle zone, formed by two or three layers of polyhedral wing cells; and a basal zone consisting of a single row of columnar cells. The stratified corneal epithelium is characterized as a "tight" ion transporting functional syncitium which serves both as a protective barrier to the ocular surface, as well as an adjunct fluid secreting layer assisting the corneal endothelium in the regulation of stromal hydration, and thereby contributing to the maintenance of corneal transparency. The unique and specialized qualities offered by the corneal epithelium have been proven to be essential for the operation of the cornea as the principal refractive element of the eye. It is therefore important that its stratified structure be maintained irrespective of any environmental stresses.

Trauma to the surface of the cornea is highly prevalent; for example, minor scrapes, eye infections and diseases, chemical or mechanical accidents and surgical practice can all damage the cornea. One major complication in post corneal-trauma wound healing is the loss of visual acuity due to tissue reorganization. Patients at risk for ophthalmic healing problems include those who have undergone surgery. Examples of such surgery include, but are not limited to, cataract extraction, with or without lens replacement; corneal transplant or other penetrating procedures, such as penetrating keratoplasty (PKP); excimer laser photorefractive keratectomy; glaucoma filtration surgery; radial keratotomy; and other types of surgery to correct refraction or replace a lens.

The cornea provides the external optically smooth surface to transmit light into the eye. Surgery disrupts the forces which anchor the cornea in its normal configuration. In cataract patients, a full-thickness surgical incision is made in the region of the limbus. The cornea contracts when it heals, causing a local distortion of the tissue and a concomitant distortion in the visual field in the affected region (astigmatism).

Other surgical wounds in the cornea can initiate a wound healing process that causes a predetermined local shift in the curvature of the cornea. The most widely known of these techniques is radial keratotomy (RK), in which several partial-thickness incisions are produced to cause central corneal flattening. This technique, however, is limited due to a lack of predictable results and significant fluctuations in vision, both of which are related to the nature and extent of wound healing (Jester et al., Cornea (1992) 11: 191). For example, a reduction in peripheral bulging of the corneal tissue with an associated regression in the initial visual improvement has been observed in most RK patients (McDonnell and Schanzlin, *Arch. Ophthalmol.* (1988), 106: 212).

Wounds in the cornea also heal slowly, and incomplete healing tends to be associated with instability of visual acuity (with fluctuations in vision from morning to evening, as well as drifting visual acuity occurring over a period of weeks to months). This may be the cause of 34% or more of patients who have had radial keratotomy complaining of fluctuating vision one year after surgery (Waring et al., *Amer. J. Ophthalmol.* (1991) 111: 133). Also, if a corneal wound fails to heal completely, a wound "gape" can occur leading to a progressive hyperopic effect. Up to 30% of patients having the RK procedure are afflicted with hyperopic shifts associated with wound gape (Dietz et al., *Ophthalmology* (1986) 93: 1284).

Corneal regeneration after trauma is complex and not well understood. It involves the regeneration of three tissues: the epithelium, the stroma and the endothelium. Three main intercellular signaling pathways are thought to coordinate tissue regeneration: one mediated by growth factors (Baldwin, H. C. and Marshall, J., *Acta Ophthalmol. Scand.*, (2002) 80: 238-47), cytokines (Ahmadi, A. J. and Jakobiec, F. A., *Int. Ophthalmol. Clinics*, (2002) 42(3): 13-22) and chemokines (Kurpakus-Wheater, M, et al., *Biotech. Histochem*, (1999) 74: 146-59); another mediated by cell-matrix interactions (Tanaka, T., et al., *Jpn. J. Ophthalmol.*, (1999) 43: 348-54); and another mediated by the gap-junctions and the connexin family of channel forming proteins.

Gap junctions are cell membrane structures, which facilitate direct cell-cell communication. A gap junction channel is formed of two connexons, each composed of six connexin subunits. Each hexameric connexon docks with a connexon in the opposing membrane to form a single gap junction. Gap junction channels can be found throughout the body. A tissue such as the corneal epithelium, for example, has six to eight cell layers, yet expresses different gap junction channels in different layers with connexin-43 in the basal layer and connexin-26 from the basal to middle wing cell layers. In general, connexins are a family of proteins, commonly named according to their molecular weight or classified on a phylogenetic basis into alpha, beta, and gamma subclasses. To date, 20 human and 19 murine isoforms have been identified (Willecke, K. et al., *Biol. Chem.*, (2002) 383, 725-37) perhaps indicating that each different connexin protein may be functionally specialized. Different tissues and cell types have characteristic patterns of connexin protein expression and tissues such as cornea have been shown to alter connexin protein expression pattern following injury or transplantation (Qui, C. et al., (2003) *Current Biology*, 13: 1967-1703; Brander et al., (2004), *J Invest Dermatol.* 122(5): 1310-20).

The corneal regeneration process post-trauma can result in the loss of corneal clarity and therefore influence the outcome of refractive surgery. Present treatments for damaged cornea generally include corneal transplant or attempts to use corneal cells/tissue for reconstruction. However, post-operative trauma to the corneal and the surrounding soft tissue following surgical procedures such as, for example, excimer laser photorefractive keratectomy, often results in scarring due to hypercellularity associated with modification of the extracellular matrix; including changes in epithelial cell patterning, myofibroblast differentiation, stromal remodeling, and epithelial hyperplasia at the site of a laser induced lesion.

In severe spinal cord injuries, the pathological changes that occur, whether by transection, contusion or compression, share some similarities with post-operative scar formation and tissue remodeling. Within 24-48 hours after injury, the damage spreads and significantly increases the size of the affected area. A gap junction-mediated bystander effect (Lin, J. H. et al., 1998, *Nature Neurosci.* 1: 431-432), by which gap junction channels spread neurotoxins and calcium waves from the damage site to otherwise healthy tissue may be involved. This is accompanied by the characteristic inflammatory swelling. The region of damage in the spinal cord is replaced by a cavity or connective tissue scar, both of which impede axonal regeneration (McDonald, J. W. et al, (September 1999) *Scientific American.* 55-63; Ramer, M. S. et al., *Spinal Cord.* (2000) 38: 449-472; Schmidt, C. E. and Baler Leach, J.; (2003) *Ann. Rev. Biomed. Eng.* 5: 293-347). Although progress has been made with some current therapeutic modalities, major constraints to spinal cord repair still remains, including the invasive intervention itself can further lesion spread and glial scar formation, impeding the repair process and risk further loss of neural function (Raisman, G J. *Royal Soc. Med.* 96: 259-261).

Antisense technology has been used for the modulation of the expression for genes implicated in viral, fungal and metabolic diseases. U.S. Pat. No. 5,166,195, proposes oligonucleotide inhibitors of HIV. U.S. Pat. No. 5,004,810 proposes oligomers for hybridizing to herpes simplex virus Vmw65 mRNA and inhibiting replication. See also WO00/44409 to Becker et al., filed Jan. 27, 2000, and entitled "Formulations Comprising Antisense Nucleotides to Connexins", the contents of which are hereby incorporated by reference in their entirety, describes the use of antisense (AS) oligodeoxynucleotides to downregulate connexin expression to treat local neuronal damage in the brain, spinal cord or optic nerve, in the promotion of wound healing and reducing scar formation of skin tissue following surgery or burns. However, many difficulties remain that need to be overcome. It is often the case, for example, that the down regulation of a particular gene product in a non-target cell type can be deleterious. Additional problems that need to be overcome include the short half life of such ODN's (unmodified phosphodiester oligomers) typically have an intracellular half life of only 20 minutes owing to intracellular nuclease degradation (Wagner 1994, supra) and their delivery consistently and reliably to target tissues.

Therefore, there is a need and there are enormous potential advantages for the development of compounds for the problems described above. Such compounds, related compositions, and methods for their use are described and claimed herein.

BRIEF SUMMARY

The inventions described and claimed herein have many attributes and embodiments including, but not limited to, those set forth or described or referenced in this Summary. The inventions described and claimed herein are not limited to or by the features or embodiments identified in this Summary, which is included for purposes of illustration only and not restriction.

Provided herein are compounds useful for tissue engineering, including antisense compounds. Also provided are antisense compounds and methods for reducing tissue damage associated with ophthalmic procedures. The methods comprise, for example, administering an antisense compound to the eye of a subject in an amount sufficient to inhibit the expression of a connexin protein in the eye or in cells associated with the eye of the subject. While it is preferred that the expression of connexin protein is inhibited, it is envisioned that other proteins may be targets for modulation by the compounds, including the antisense compounds, either alone of in combination with antisense or other compounds that inhibit the expression of human connexins.

In certain embodiments, the ophthalmic procedure is an ophthalmic surgery, including but not limited to an excimer laser photorefractive keratectomy, a cataract extraction, corneal transplant, a surgery to correct refraction, a radial keratotomy, a glaucoma filtration surgery, a keratoplasty, an excimer laser photorefractive keratectomy, a corneal transplant, a surgery to correct refraction, a ocular surface neoplasm excision, a conjunctival or amniotic membrane graft, a pterygium and pingeculae excision, a ocular plastic surgery, a lid tumour excision, a reconstructive lid procedures for congentital abnormalities, an ectropian and entropian eyelid repair, a strabismus surgery (occular muscle), or any penetrating eye trauma.

Generally, at least a portion of the nucleotide sequence is known for connexins in which the inhibition of expression is desired. Preferably, an antisense compound is targeted to one or more specific connexin isotypes. Specific isotypes of connexins that may be targeted by the antisense compounds include, without limitation, 43, 37, 31.1, and 26. It is preferred, but not required, that the targeted connexins are human. A connexin (e.g., human) may, for example, have a nucleobase sequence selected from SEQ ID NO: 12-31.

In certain embodiments, antisense compounds are targeted to at least about 8 nucleobases of a nucleic acid molecule encoding a connexin having a nucleobase sequence selected from SEQ ID NO: 12-31.

In certain other embodiments, a second antisense compound is administered to the subject (e.g. the eye), wherein one or more other antisense compounds are targeted to at least about 8 nucleobases of a nucleic acid molecule encoding a connexin (e.g., human) having a nucleobase sequence selected from SEQ ID NO: 12-31. At least a second antisense compound may, for example, be targeted to a different connexin than a first antisense compound.

Examples of types of antisense compounds that may be used in various aspects of the invention include antisense oligonucleotides, antisense polynucleotides, deoxyribozymes, morpholino oligonucleotides, dsRNA, RNAi molecules, siRNA molecules, PNA molecules, DNAzymes, and 5'-end-mutated U1 small nuclear RNAs, analogs of the preceding; as well other compounds provided herein or known in the art; including but not limited to, for example, non-specific uncouplers such as octanol, glycerhetinic acids, and heptanol.

In certain embodiments, for example, the antisense compounds are antisense oligonucleotides that comprise naturally occurring nucleobases and an unmodified internucleoside linkage. In other embodiments, for example, the antisense compounds are antisense oligonucleotides comprising at least one modified internucleoside linkage, including those with a phosphorothioate linkage. Suitable antisense compounds also include, for example, oligonucleotides comprising at least one modified sugar moiety. Suitable antisense compounds also include, by way of example, oligonucleotides comprising at least one modified nucleobase.

In certain embodiments, antisense compounds provided herein are administered in combination with another compound, for example a compound useful for reducing tissue damage, reducing inflammation, promoting healing, or some other desired activity.

In another aspect, the invention includes methods of treating a subject (e.g., a patient) by administering antisense compounds to the subject.

In certain embodiments, antisense compounds provided herein are administered by local or topical administration.

Antisense compounds provided herein can also be administered, for example, systemically or by intraocular injection.

Antisense compounds provided herein can be administered to a subject at a predetermined time, for example, relative to the formation of a wound, such as that occurs in an ophthalmic procedure (e.g., surgical). For example, antisense compounds can be administered before an ophthalmic procedure is performed, during an ophthalmic procedure, or after an ophthalmic procedure. Antisense compounds, for example, may be administered to a subject within minutes or hours before or after an ophthalmic procedure is performed. In certain embodiments, an antisense compound is administered after an ophthalmic procedure is performed, and for example the antisense compound is administered within about 4 hours of the procedure, within about 3 hours of the procedure, and more typically within about 2 hours of the ophthalmic procedure, or within about 1 hour of an ophthalmic procedure.

In another aspect, antisense compounds provided herein may be administered in a methods to effect tissue engineering. For example, antisense compounds provided herein may be administered in conjunction with a method that increases the thickness of cornea tissue in a subject. Such method may, or may not, be associated with an ophthalmic procedure (e.g., surgery). As an example, antisense compounds provided herein may be administered in conjunction with a method that promotes healing or prevents tissue damage in cells associated with the cornea of the subject (e.g., corneal cells).

In certain embodiments, for example, the antisense compound decreases scar formation. In certain embodiments, for example, the antisense compound reduces inflammation. In certain embodiments, for example, the antisense compound promotes wound healing.

In certain preferred embodiments, for example, the antisense compound is used in association with a surgical implantation procedure.

In certain embodiments, for example, the antisense compound is directed to connexin 43 and is administered to regulate epithelial basal cell division and growth.

In certain embodiments, for example, the antisense compound is directed to connexin 31.1 and is administered to regulate outer layer keratinisation.

According to certain embodiments, for example, the ophthalmic procedure is cataract extraction. In other embodiments, for example, the ophthalmic procedure is a corneal transplant. In other embodiments, for example, the ophthalmic surgical procedure is surgery to correct refraction. In another embodiments, for example, the ophthalmic procedure is radial keratotomy. In another embodiments, for example, the ophthalmic procedure is glaucoma filtration surgery. In still other embodiments, for example, the ophthalmic procedure is keratoplasty. In other embodiments, for example, the ophthalmic procedure is an ocular surface neoplasm excision. In other embodiments, for example, the ophthalmic procedure is a conjunctival or amniotic membrane graft. In other embodiments, for example, the ophthalmic procedure is a pterygium and pingeculae excision. In other embodiments, for example, the ophthalmic procedure is an ocular plastic surgery. In other embodiments, for example, the ophthalmic procedure is a lid tumour excision. In other embodiments, for example, the ophthalmic procedure is a reconstructive lid procedure for congentital abnormalities. In other embodiments, for example, the ophthalmic procedure is an ectropian and entropian eyelid repair. In other embodiments, for example, the ophthalmic procedure is a strabismus surgery (occular muscle). In other embodiments, for example, the ophthalmic procedure is a penetrating eye trauma.

In certain further embodiments, for example, compounds and compositions are used to promote healing or to prevent tissue damage in cells associated with cornea, where the cells associated with the cornea may be any cell in the eye, including but not limited to corneal cells.

The agents provided herein, including antisense compounds, may increase the thickness of cornea tissue in a subject. In certain embodiments, for example, the antisense compound is used in combination with another compound useful for reducing tissue damage or promoting healing. For example, the antisense compounds may be coadministered with a growth factor, cytokine, or the like.

In another aspect, for example, a pharmaceutical composition for reducing tissue damage associated with ophthalmic surgery is provided. The pharmaceutical composition is suitably formulated, for example, for topical or local administration to the eye of a subject comprising an antisense compound present in an amount sufficient to inhibit the expression of a human connexin protein in cells associated with the eye of the subject. The antisense compound, for example, is preferably targeted to at least about 8 nucleobases of a nucleic acid molecule encoding a connexin (e.g., human) having a nucleobase sequence selected from SEQ ID NO:12-31.

In certain embodiments, for example, the antisense compounds are in the form of a pharmaceutical composition comprising a pharmaceutically acceptable carrier or vehicle and the agent or antisense compound is present in an amount effective to promote wound healing in a subject. In certain embodiments, the pharmaceutical compositions may be, for example, in a form suitable for topical administration, including in a form suitable for topical or local administration to the eye of a subject. In certain further embodiments, for example, the compositions and formulations may be in the form of a gel, a cream, or any of the forms described herein or known in the art, whether currently or in the future.

In another aspect, the invention includes pharmaceutical compositions comprising antisense compounds. In one embodiment, for example, a pharmaceutical composition is provided for reducing tissue damage associated with an ophthalmic procedure (e.g., surgery), such that the pharmaceutical composition is formulated for topical or local administration to the eye of a subject and it comprises an antisense compound present in an amount sufficient to inhibit the expression of a human connexin protein in cells associated with the eye of the subject. In certain embodiments, for example, the antisense compound is targeted to at least about 8 nucleobases of a nucleic acid molecule encoding a connexin (e.g., human) having a nucleobase sequence selected from SEQ ID NO: 12-31.

In certain embodiments, for example, the pharmaceutical composition includes a pharmaceutically acceptable carrier comprising a buffered pluronic acid or gel. This includes in one embodiment, for example, up to about 30% pluronic acid in phosphate buffered saline.

In another aspect, methods of designing antisense oligonucleotides that are targeted to one or more connexin are provided. The method may include the optimization of selected parameters, such as the thermo stability, affinity, and specificity of a particular oligonucleotide with a selected target. This method may be used to selected and develop antisense oligonucleotides comprising one or more particular desired polynucleotide sequence. Testing of the antisense oligonucleotides may be performed in conjunction with the method, for example, for their ability to cleave mRNA or block the translation of a connexin protein.

BRIEF DESCRIPTION OF THE DRAWINGS

FIGS. 4A, 4B, and 4C are controls; and 4D, 4E, and 4F are antisense treated corneas.

FIG. 5F—central) and it was very uneven (5E). In contrast antisense ODN treated corneas had a continuous and relatively even basal lamina at the wound edge (5G) and centrally (5H).

FIG. 4A shows the normal connexin-43 protein expression (light, gray-scale) in the basal cells and connexin-26 protein expression (dark,gray-scale) in the basal to intermediate cells of a Pluronic gel control treated corneal epithelium. As14 (14B), as769 (14D), as892 (14F), all three showing no deoxyribozyme cleavage in vitro) and DB1 sense control (14H) oligomers did not affect the expression of both connexins in ex vivo cultures. as605 (14C), as783 (14E) and DB1 (14G) (all three showing positive in vitro deoxyribozyme cleavage) showed only specific connexin-43 knock down in the epithelium of treated corneas.

DETAILED DESCRIPTION

Figure 1:
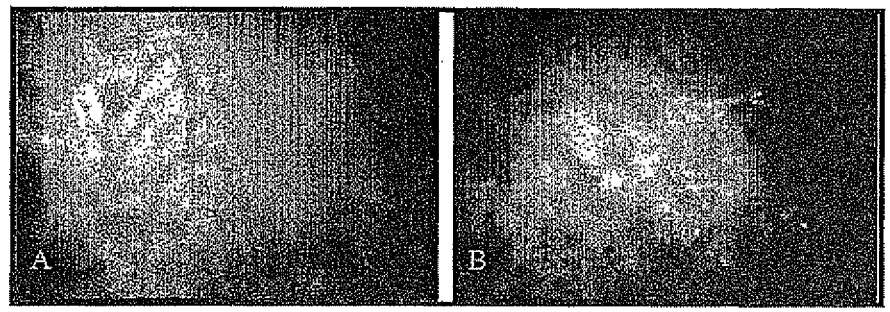
FIG. 1 shows in vivo confocal microscopic images of corneas 12 hours post photorefractive keratectomy in control and antisense oligonucleotides treated eyes.

The practice of the present inventions may employ various conventional techniques of molecular biology (including recombinant techniques), microbiology, cell biology, biochemistry, nucleic acid chemistry, and immunology, which are within the skill of the art. Such techniques are explained fully in the literature, and include but are not limited to, by way of example only, Molecular Cloning: A Laboratory Manual, second edition (Sambrook et al., 1989) and Molecular Cloning: A Laboratory Manual, third edition (Sambrook and Russel, 2001), jointly and individually referred to herein as "Sambrook"; Oligonucleotide Synthesis (M. J. Gait, ed., 1984); Animal Cell Culture (R. I. Freshney, ed., 1987); Handbook of Experimental Immunology (D. M. Weir & C. C. Blackwell, eds.); Gene Transfer Vectors for Mammalian Cells (J. M. Miller & M. P. Calos, eds., 1987); Current Protocols in Molecular Biology (F. M. Ausubel et al., eds., 1987, including supplements through 2001); PCR: The Polymerase Chain Reaction, (Mullis et al., eds., 1994); Current Protocols in Immunology (J. E. Coligan et al., eds., 1991); The Immunoassay Handbook (D. Wild, ed., Stockton Press NY, 1994); Bioconjugate Techniques (Greg T. Hermanson, ed., Academic Press, 1996); Methods of Immunological Analysis (R. Masseyeff, W. H. Albert, and N. A. Staines, eds., Weinheim: VCH Verlags gesellschaft mbH, 1993), Harlow and Lane (1988) Antibodies, A Laboratory Manual, Cold Spring Harbor Publications, New York, and Harlow and Lane (1999) Using Antibodies: A Laboratory Manual Cold Spring Harbor Laboratory Press, Cold Spring Harbor, N.Y. (jointly and individually referred to herein as Harlow and Lane), Beaucage et al. eds., Current Protocols in Nucleic Acid Chemistry John Wiley & Sons, Inc., New York, 2000); and Agrawal, ed., Protocols for Oligonucleotides and Analogs, Synthesis and Properties Humana Press Inc., New Jersey, 1993).

Definitions

Before further describing the inventions in general and in terms of various nonlimiting specific embodiments, certain terms used in the context of the describing the invention are set forth. Unless indicated otherwise, the following terms have the following meanings when used herein and in the appended claims. Those terms that are not defined below or elsewhere in the specification shall have their art-recognized meaning.

"Antisense compounds" include different types of molecule that act to inhibit gene expression, translation, or function, including those that act by sequence-specific targeting of mRNAs for therapeutic applications.

Antisense compounds thus include, for example, the major nucleic-acid based gene-silencing molecules such as, for example, chemically modified antisense oligodeoxyribonucleic acids (ODNs), ribozymes and siRNAs (Scherer, L. J. and Rossi, J. J. *Nature Biotechnol.* 21: 1457-1465 (2003). Antisense compounds may also include antisense molecules such as, for example, peptide nucleic acids (PNAs) (Braasch, D. A. and Corey, D. R., *Biochemistry* 41, 4503-4510 (2002)), morpholino phosphorodiamidates (Heasman, J., *Dev. Biol.,* 243, 209-214 (2002), DNAzymes (Schubert, S. et al., *Nucleic Acids Res.* 31, 5982-5992 (2003). Chakraborti, S. and Banerjea, A. C., *Mol. Ther.* 7, 817-826 (2003), Santoro, S. W. and Joyce, G. F. *Proc. Natl Acad. Sci. USA* 94, 4262-4266 (1997), and the recently developed 5'-end-mutated U1 small nuclear RNAs (Fortes, P. et al., *Proc. Natl. Acad. Sci. USA* 100, 8264-8269 (2003)).

The term "antisense sequences" refers to polynucleotides having antisense compound activity and include, but are not limited to, sequences complementary or partially complementary, for example, to an RNA sequence. Antisense sequences thus include, for example, include nucleic acid sequences that bind to mRNA or portions thereof to block transcription of mRNA by ribosomes. Antisense methods are generally well known in the art. See, for example, PCT publication WO94/12633, and Nielsen et al., 1991, Science 254:1497; Oligonucleotides and Analogues, A Practical Approach, edited by F. Eckstein, IRL Press at Oxford University Press (1991); Antisense Research and Applications (1993, CRC Press.

As used herein, "messenger RNA" includes not only the sequence information to encode a protein using the three letter genetic code, but also associated ribonucleotide sequences which form the 5'-untranslated region, the 3'-untranslated region, and the 5' cap region, as well as ribonucleotide sequences that form various secondary structures. Oligonucleotides may be formulated in accordance with this invention which are targeted wholly or in part to any of these sequences.

In general, nucleic acids (including oligonucleotides) may be described as "DNA-like" (i.e., having 2'-deoxy sugars and, generally, T rather than U bases) or "RNA-like" (i.e., having 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-form-like structure are "RNA-like".

The term "complementary" generally refers to the natural binding of polynucleotides under permissive salt and temperature conditions by base pairing. For example, the sequence "A-G-T" binds to the complementary sequence "T-C-A". Complementarity between two single-stranded molecules may be "partial", such that only some of the nucleic acids bind, or it may be "complete", such that total complementarity exists between the single stranded molecules. The degree of complementarity between nucleic acid molecules has significant effects on the efficiency and strength of the hybridization between them. "Hybridizable" and "complementary" are terms that are used to indicate a sufficient degree of complementarity such that stable and binding occurs between the DNA or RNA target and the oligonucleotide. It is understood that an oligonucleotide need not be 100% complementary to its target nucleic acid sequence to be hybridizable, and it is also understood that the binding may be target-specific, or may bind to other non-target molecules so long as the non-specific binding does not significantly or undesireably thwart the therapeutic or other objective. An oligonucleotide is used to interfere with the normal function of the target molecule to cause a loss or diminution of activity, and it is preferred that there is a sufficient degree of complementarity to avoid non-specific or unwanted binding of the oligonucleotide to non-target sequences under conditions in which specific binding is desired, i.e., under physiological conditions in the case of in vivo assays or therapeutic treatment or, in the case of in vitro assays, under conditions in which the assays are conducted. In the context of certain embodiments of the invention, absolute complementarity is not required. Polynucleotides that have sufficient complementarity to form a duplex having a melting temperature of greater than 20° C., 30° C., or 40° C. under physiological conditions, are generally preferred.

A "disorder" is any condition that would benefit from treatment with a molecule or composition of the invention, including those described or claimed herein. This includes chronic and acute disorders or diseases including those pathological conditions that predispose the mammal to the disorder in question.

"Targeting" an oligonucleotide to a chosen nucleic acid target can be a multistep process. The process may begin with identifying a nucleic acid sequence whose function is to be modulated. This may be, for example, a cellular gene (or mRNA made from the gene) whose expression is associated with a particular disease state, or a foreign nucleic acid (RNA or DNA) from an infectious agent. The targeting process may also include determination of a site or sites within the nucleic acid sequence for the oligonucleotide interaction to occur such that the desired effect, i.e., inhibition of protein expression, reduced protein detection, or other modulation of activity, will result. Once a target site or sites have been identified, antisense compounds (e.g., oligonucleotides) are chosen which are sufficiently or desirably complementary to the target, i.e., hybridize sufficiently and with an adequate or otherwise desired specificity, to give the desired modulation. In the present invention, targets include nucleic acid molecules encoding one or more connexins. The targeting process may also include determination of a site or sites for the antisense interaction to occur such that the desired effect, will result. A preferred intragenic site, for example, is the region encompassing the translation initiation or termination codon of the open reading frame (ORF) of the gene. The translation initiation codon is typically 5'-AUG (in transcribed mRNA molecules; 5'-ATG in the corresponding DNA molecule), tand may also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions.

The term "oligonucleotide" includes an oligomer or polymer of nucleotide or nucleoside monomers consisting of naturally occurring bases, sugars and intersugar (backbone) linkages. The term "oligonucleotide" also includes oligomers or polymers comprising non-naturally occurring monomers, or portions thereof, which function similarly. Such modified or substituted oligonucleotides are often preferred over native forms because of properties such as, for example, enhanced cellular uptake, increased stability in the presence of nucleases, or enhanced target affinity. A number of nucleotide and nucleoside modifications have been shown to make the oligonucleotide into which they are incorporated more resistant to nuclease digestion than the native oligodeoxynucleotide (ODN). Nuclease resistance is routinely measured by incubating oligonucleotides with cellular extracts or isolated nuclease solutions and measuring the extent of intact oligonucleotide remaining over time, usually by gel electrophoresis. Oligonucleotides, which have been modified to enhance their nuclease resistance, can survive intact for a longer time than unmodified oligonucleotides. A number of modifications have also been shown to increase binding (affinity) of the oligonucleotide to its target. Affinity of an oligonucleotide for its target is routinely determined by measuring the Tm (melting temperature) of an oligonucleotide/target pair, which is the temperature at which the oligonucleotide and target dissociate. Dissociation is detected spectrophotometrically. The greater the Tm, the greater the affinity of the oligonucleotide has for the target. In some cases, oligonucleotide modifications which enhance target-binding affinity are also able to enhance nuclease resistance.

A "polynucleotide" means a plurality of nucleotides. Thus, the terms "nucleotide sequence" or "nucleic acid" or "polynucleotide" or "oligonucleotide" or "oligodeoxynucleotide" all refer to a heteropolymer of nucleotides or the sequence of these nucleotides. These phrases also refer to DNA or RNA of genomic or synthetic origin which may be single-stranded or double-stranded and may represent the sense or the antisense strand, to peptide nucleic acid (PNA) or to any DNA-like or RNA-like material.

A polynucleotide that encodes a connexin, a connexin fragment, or a connexin variant includes a polynucleotide encoding: the mature form of the connexin found in nature; the mature form of the connexin found in nature and additional coding sequence, for example, a leader or signal sequence or a proprotein sequence; either of the foregoing and non-coding sequences (for example, introns or non-coding sequence 5' and/or 3' of the coding sequence for the mature form of the polypeptide found in nature); fragments of the mature form of the connexin found in nature; and variants of the mature form of the connexin found in nature. Thus, "connexin-encoding polynucleotide" and the like encompass polynucleotides that include only a coding sequence for a desired connexin, fragment, or variant, as well as a polynucleotide that includes additional coding and/or non-coding sequences.

The terms "peptidomimetic" and "mimetic" refer to a synthetic chemical compound that may have substantially the same structural and functional characteristics of the antisense polypeptides provided herein and that mimic the connexin-specific inhibitory activity, at least in part and to some degree. Peptide analogs are commonly used in the pharmaceutical industry as non-peptide drugs with properties analogous to those of the template peptide. These types of non-peptide compound are termed "peptide mimetics" or "peptidomimetics" (Fauchere, *J. Adv. Drug Res.* 15: 29 (1986); Veber and Freidinger; *TINS;* 392 (1985); and Evans et al., *J. Med. Chem.* 30: 1229 (1987); Beeley N., *Trends Biotechnol.* 1994 June; 12(6): 213-6; Kieber-Emmons T, et al.; *Curr Opin Biotechnol.* 1997 August; 8(4): 435-41. Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as a antisense polynucleotide, but have one or more peptide linkages optionally replaced by a linkage selected from the group consisting of, for example, —CH2NH—, —CH2S—, —CH2-CH2-, —CH=CH— (cis and trans), —COCH2-, —CH(OH)CH2-, and —CH2SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. For example, a mimetic composition is within the scope of the invention if it is capable of down-regulating biological activities of connexin proteins, such as, for example, gap-junction-mediated-cell-cell communication.

The term "composition" is intended to encompass a product comprising one or more ingredients.

The terms "modulator" and "modulation" of connexin activity, as used herein in its various forms, is intended to encompass inhibition in whole or in part of the expression or activity of a connexin. Such modulators include small molecules agonists and antagonists of connexin function or expression, antisense molecules, ribozymes, triplex molecules, and RNAi polynucleotides, gene therapy methods, and others.

The phrase "percent (%) identity" refers to the percentage of sequence similarity found in a comparison of two or more sequences. Percent identity can be determined electronically using any suitable software Likewise, "similarity" between two sequences (or one or more portions of either or both of them) is determined by comparing the sequence of one sequence to the a second sequence.

By "pharmaceutically acceptable" it is meant, for example, a carrier, diluent or excipient that is compatible with the other ingredients of the formulation and suitable for administration to a recipient thereof.

In general, the term "protein" refers to any polymer of two or more individual amino acids (whether or not naturally occurring) linked via peptide bonds, as occur when the carboxyl carbon atom of the carboxylic acid group bonded to the alpha-carbon of one amino acid (or amino acid residue) becomes covalently bound to the amino nitrogen atom of the amino group bonded to the alpha-carbon of an adjacent amino acid. These peptide bond linkages, and the atoms comprising them (i.e., alpha-carbon atoms, carboxyl carbon atoms (and their substituent oxygen atoms), and amino nitrogen atoms (and their substituent hydrogen atoms)) form the "polypeptide backbone" of the protein. In addition, as used herein, the term "protein" is understood to include the terms "polypeptide" and "peptide" (which, at times, may be used interchangeably herein). Similarly, protein fragments, analogs, derivatives, and variants are may be referred to herein as "proteins," and shall be deemed to be a "protein" unless otherwise indicated. The term "fragment" of a protein refers to a polypeptide comprising fewer than all of the amino acid residues of the protein. As will be appreciated, a "fragment" of a protein may be a form of the protein truncated at the amino terminus, the carboxy terminus, and/or internally (such as by natural splicing), and may also be variant and/or derivative. A "domain" of a protein is also a fragment, and comprises the amino acid residues of the protein required to confer biochemical activity corresponding to naturally occurring protein. Truncated molecules that are linear biological polymers such as nucleic acid molecules or polypeptides may have one or more of a deletion from either terminus of the molecule and/or one or more deletions from a non-terminal region of the molecule, where such deletions may be deletions of from about 1-1500 contiguous nucleotide or amino acid residues, preferably about 1-500 contiguous nucleotide or amino acid residues and more preferably about 1-300 contiguous nucleotide or amino acid residues, including deletions of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31-40, 41-50, 51-74, 75-100, 101-150, 151-200, 201-250 or 251-299 contiguous nucleotide or amino acid residues.

The term "stringent conditions" refers to conditions that permit hybridization between polynucleotides. Stringent conditions can be defined by salt concentration, the concentration of organic solvent (for example, formamide), temperature, and other conditions well known in the art. Stringency can be increased by reducing the concentration of salt, increasing the concentration of organic solvents, (for example, formamide), or raising the hybridization temperature. For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, for example, formamide, while high stringency hybridization can be obtained in the presence of an organic solvent (for example, at least about 35% formamide, most preferably at least about 50% formamide). Stringent temperature conditions will ordinarily include temperatures of at least about 30° C., more preferably of at least about 37° C., and most preferably of at least about 42° C. Varying additional parameters, for example, hybridization time, the concentration of detergent, for example, sodium dodecyl sulfate (SDS), and the inclusion or exclusion of carrier DNA, are well known to those skilled in the art. Various levels of stringency are accomplished by combining these various conditions as needed, and are within the skill in the art. Stringent hybridization conditions may also be defined by conditions in a range from about 5° C. to about 20° C. or 25° C. below the melting temperature (Tm) of the target sequence and a probe with exact or nearly exact complementarity to the target. As used herein, the melting temperature is the temperature at which a population of double-stranded nucleic acid molecules becomes half-dissociated into single strands. Methods for calculating the Tm of nucleic acids are well known in the art (see, for example, Berger and Kimmel, 1987, Methods In Enzymology, Vol. 152: *Guide To Molecular Cloning Techniques*, San Diego: Academic Press, Inc. and Sambrook et al., (1989) Molecular Cloning: A Laboratory Manual, 2nd Ed., Vols. 1-3, Cold Spring Harbor Laboratory). As indicated by standard references, a simple estimate of the Tm value may be calculated by the equation: Tm=81.5+0.41(% G+C), when a nucleic acid is in aqueous solution at 1 M NaCl (see for example, Anderson and Young, "Quantitative Filter Hybridization" in Nucleic Acid Hybridization (1985)). The melting temperature of a hybrid (and thus the conditions for stringent hybridization) is affected by various factors such as the length and nature (DNA, RNA, base composition) of the probe and nature of the target (DNA, RNA, base composition, present in solution or immobilized, and the like), and the concentration of salts and other components (for example for example, the presence or absence of formamide, dextran sulfate, polyethylene glycol). The effects of these factors are well known and are discussed in standard references in the art, see for example, Sambrook, supra, and Ausubel, supra. Typically, stringent hybridization conditions are salt concentrations less than about 1.0 M sodium ion, typically about 0.01 to 1.0 M sodium ion at pH 7.0 to 8.3, and temperatures at least about 30° C. for short probes (for example, 10 to 50 nucleotides) and at least about 60° C. for long probes (for example, greater than 50 nucleotides). As noted, stringent conditions may also be achieved with the addition of destabilizing agents such as formamide, in which case lower temperatures may be employed. In the present invention, the polynucleotide may be a polynucleotide which hybridizes to the connexin mRNA under conditions of medium to high stringency such as 0.03M sodium chloride and 0.03M sodium citrate at from about 50 to about 60 degrees centigrade.

The term "therapeutically effective amount" means the amount of the subject compound that will elicit a desired response, for example, a biological or medical response of a tissue, system, animal or human that is sought, for example, by a researcher, veterinarian, medical doctor, or other clinician.

"Treatment" refers to both therapeutic treatment and prophylactic or preventive measures. Those in need of treatment include those already with the disorder as well as those in which the disorder is to be prevented.

The term "vector" refers to a nucleic acid molecule amplification, replication, and/or expression vehicle in the form of a plasmid, phage, viral, or other system (be it naturally occurring or synthetic) for the delivery of nucleic acids to cells where the plasmid, phage, or virus may be functional with bacterial, yeast, invertebrate, and/or mammalian host cells. The vector may remain independent of host cell genomic DNA or may integrate in whole or in part with the genomic DNA. The vector will generally but need not contain all necessary elements so as to be functional in any host cell it is compatible with. An "expression vector" is a vector capable of directing the expression of an exogenous polynucleotide, for example, a polynucleotide encoding a binding domain fusion protein, under appropriate conditions.

As described herein, the terms "homology and homologues" include polynucleotides that may be a homologue of sequence in connexin polynucleotide (e.g. mRNA). Such polynucleotides typically have at least about 70% homology, preferably at least about 80%, 90%, 95%, 97% or 99% homology with the relevant sequence, for example over a region of at least about 15, 20, 30, 40, 50, 100 more contiguous nucleotides (of the homologous sequence).

Homology may be calculated based on any method in the art. For example the UWGCG Package provides the BEST-FIT program which can be used to calculate homology (for example used on its default settings) (Devereux et al. (1984) Nucleic Acids Research 12, p 387-395). The PILEUP and BLAST algorithms can be used to calculate homology or line up sequences (typically on their default settings), for example as described in Altschul S. F. (1993); *J Mol Evol* 36: 290-300; Altschul, S. F. et al.; (1990); *J Mol Biol* 215: 403-10. Software for performing BLAST analyses is publicly available through the National Center for Biotechnology Information (http://www.ncbi.nlm.nih.gov/L). This algorithm involves first identifying high scoring sequence pair by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence is less than about 1, preferably less than about 0.1, more preferably less than about 0.01, and most preferably less than about 0.001.

The homologous sequence typically differs from the relevant sequence by at least (or by no more than) about 1, 2, 5, 10, 15, 20 or more mutations (which may be substitutions, deletions or insertions). These mutations may be measured across any of the regions mentioned above in relation to calculating homology. The homologous sequence typically hybridizes selectively to the original sequence at a level significantly above background. Selective hybridization is typically achieved using conditions of medium to high stringency (for example 0.03M sodium chloride and 0.03M sodium citrate at from about 50 degrees C. to about 60 degrees C.). However, such hybridization may be carried out under any suitable conditions known in the art (see Sambrook et al. (1989), Molecular Cloning: A Laboratory Manual). For example, if high stringency is required, suitable conditions include 0.2×SSC at 60 degrees C. If lower stringency is required, suitable conditions include 2×SSC at 60 degrees C.

A "cell" means any living cell suitable for the desired application. Cells include eukaryotic and prokaryotic cells.

The term "gene product" refers to an RNA molecule transcribed from a gene, or a polypeptide encoded by the gene or translated from the RNA.

The term "recombinant" refers to a polynucleotide synthesized or otherwise manipulated in vitro (for example, "recombinant polynucleotide"), to methods of using recombinant polynucleotides to produce gene products in cells or other biological systems, or to a polypeptide ("recombinant protein") encoded by a recombinant polynucleotide. Thus, a "recombinant" polynucleotide is defined either by its method of production or its structure. In reference to its method of production, the process refers to use of recombinant nucleic acid techniques, for example, involving human intervention in the nucleotide sequence, typically selection or production. Alternatively, it can be a polynucleotide made by generating a sequence comprising a fusion of two or more fragments that are not naturally contiguous to each other. Thus, for example, products made by transforming cells with any non-naturally occurring vector is encompassed, as are polynucleotides comprising sequence derived using any synthetic oligonucleotide process. Similarly, a "recombinant" polypeptide is one expressed from a recombinant polynucleotide.

A "recombinant host cell" is a cell that contains a vector, for example, a cloning vector or an expression vector, or a cell that has otherwise been manipulated by recombinant techniques to express a protein of interest.

This invention includes methods of using compounds and compositions for site-specific modulation of gap-junction-associated protein expression for wound-healing, for example, well as, for example, surgically related wound-healing and/or tissue remodeling applications. The invention is useful, for example, for correcting visual defects in conjunction with laser surgery, for in vitro corneal engineering, and for direct eye treatments where remodeling of the cornea is desired, including those preformed independent of or alternatively, in conjunction with, a procedure (e.g., surgery) performed on the eye. Antisense modulation of direct cell-cell communication is preferably mediated by molecules that directly or indirectly reduce coupling between cells in tissues. Such molecules include polynucleotides such as antisense deoxynucleotides, morpholino nucleotides, RNAi and deoxyribozymes targeted to specific connexin isoforms which result in reduced translation of the protein isoform and interfere with the function of cell gap junctions. Administration of these antisense compounds results in the reduction of gap-junction-mediated cell-cell communication at the site at which connexin expression is downregulated.

Connexins play important roles in gap junction-mediated cell-cell signaling. Overexpression of connexin is associated with post surgical scarring and post-trauma-induced tissue remodeling. According to certain embodiments of the invention, connexins represent useful targets for treatment of adverse effects associated with corneal trauma and post-surgical tissue remodeling; and for diseases and disorders where localized disruption in direct cell-cell communication is desirable. Particularly, modulation of the expression of connexins can be useful for the site-specific modulation of gap-junction-associated protein expression for tissue remodeling/tissue engineering applications. Antisense compounds provided herein may be used for the modulation of connexins in association with ophthalmic procedures or surgeries such as, for example, cataract surgery, intraocular lens surgery, corneal transplant surgery and some types of glaucoma surgery, and other procedures described herein.

In certain embodiments, the modulation of the connexins can be applied in ophthalmic disorders affecting the posterior segment, including the retina and lens. In another aspect of this invention, the modulation of the connexins can be applied in ophthalmic disorders affecting the anterior segment, which includes the cornea, conjunctiva and sclera. In the context of this invention, posterior segment disorders include macular holes and degeneration, retinal tears, diabetic retinopathy, vitreoretinopathy and miscellaneous disorders. Also in the context of this invention, a disorder of the lens may include cataracts. In yet another aspect, it is contemplated that the disorders of the cornea are refractive disorders such as the sequalae of radial keratotomy, dry eye, viral conjunctivitis, ulcerative conjunctivitis and scar formation in wound healing, such as, for example, corneal epithelial wounds, and the consequences of Sjogren's syndrome.

The present invention discloses antisense compounds, particularly oligonucleotides, for use in modulating the function of nucleic acid molecules encoding connexins, ultimately modulating the amount of connexins produced. This is accomplished by providing oligonucleotides which specifically hybridize with nucleic acids, preferably mRNA, encoding connexins.

This relationship between an antisense compound such as an oligonucleotide and its complementary nucleic acid target, to which it hybridizes, is commonly referred to as "antisense". As described herein, "targeting" of an oligonucleotide to a chosen nucleic acid target is typically a multistep process. The process usually begins with identifying a nucleic acid sequence whose function is to be modulated. This may be, as an example, a cellular gene (or mRNA made from the gene) whose expression is associated with a particular disease state. In the present invention, the targets are nucleic acids encoding connexins; in other words, a gene encoding connexin, or mRNA expressed from the connexin gene. mRNA which encodes connexin is presently a preferred target. The targeting process also includes determination of a site or sites within the nucleic acid sequence for the antisense interaction to occur such that modulation of gene expression will result.

In the context of the invention, messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with the present invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding connexin, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns", which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

In the context of this invention, an antisense polynucleotide may, for example, hybridize to all or part of a connexin mRNA. Typically the antisense polynucleotide hybridizes to the ribosome binding region or the coding region of the connexin mRNA. The polynucleotide may be complementary to all of or a region of a connexin mRNA. For example, the polynucleotide may be the exact complement of all or a part of connexin mRNA. The antisense polynucleotide may inhibit transcription and/or translation of the connexin. Preferably the polynucleotide is a specific inhibitor of transcription and/or translation of the connexin gene, and does not inhibit transcription and/or translation of other genes. The product may bind to the connexin gene or mRNA either (i) 5' to the coding sequence, and/or (ii) to the coding sequence, and/or (iii) 3' to the coding sequence. Generally the antisense polynucleotide will cause the expression of connexin mRNA and/or protein in a cell to be reduced. The antisense polynucleotide is generally antisense to the connexin mRNA. Such a polynucleotide may be capable of hybridizing to the connexin mRNA and may inhibit the expression of connexin by interfering with one or more aspects of connexin mRNA metabolism including transcription, mRNA processing, mRNA transport from the nucleus, translation or mRNA degradation. The antisense polynucleotide typically hybridizes to the connexin mRNA to form a duplex which can cause direct inhibition of translation and/or destabilization of the mRNA. Such a duplex may be susceptible to degradation by nucleases.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of expression of connexin. In the context of this invention "modulation" includes either inhibition or stimulation; i.e., either a decrease or increase in expression. This modulation can be measured in ways which are routine in the art, for example by Northern blot assay of mRNA expression, or reverse transcriptase PCR, as taught in the examples of the instant application or by Western blot or ELISA assay of protein expression, or by an immunoprecipitation assay of protein expression. Effects on cell proliferation or tumor cell growth can also be measured, as taught in the examples of the instant application. Inhibition is presently preferred.

Once the target site or sites have been identified, oligonucleotides are chosen which are sufficiently complementary to the target, i.e., hybridize sufficiently well and with sufficient specificity, to give the desired modulation. The antisense nucleic acids (DNA, RNA, modified, analogues, and the like) can be made using any suitable method for producing a nucleic acid. Oligodeoxynucleotides directed to other connexin proteins can be selected in terms of their nucleotide sequence by any art recognized approach, such as, for example, the computer programs MacVector and OligoTech (from Oligos etc. Eugene, Oreg., USA). Equipment for such synthesis is available through several vendors including MacVector and OligoTech (from Oligos etc. Eugene, Oreg., USA). For general methods relating to antisense polynucleotides, see Antisense RNA and DNA, D. A. Melton, Ed., Cold Spring Harbor Laboratory, Cold Spring Harbor, N.Y. (1988)). See also, Dagle et al., *Nucleic Acids Research,* 19: 1805 (1991). For antisense therapy, see, for example, Uhlmann et al., *Chem. Reviews,* 90: 543-584 (1990). Typically, at least a portion of the nucleotide sequence is known for connexins in which the inhibition of expression is desired. Preferably, an antisense compound is targeted to one or more specific connexin isotypes. Specific isotypes of connexins that may be targeted by the antisense compounds include, without limitation, 43, 37, 31.1, 26, and others described herein. It is preferred, but not required, that the targeted connexins are human. A connexin may, for example, have a nucleobase sequence selected from SEQ ID NO:12-31. In certain embodiments, antisense compounds are targeted to at least 8 nucleobases of a nucleic acid molecule encoding a connexin having a nucleobase sequence selected from SEQ ID NO:12-31.

In certain other embodiments, a second antisense compound is administered to the eye of the subject, wherein the second antisense compound is targeted to at least about 8 nucleobases of a nucleic acid molecule encoding a connexin having a nucleobase sequence selected from SEQ ID NO:12-31, wherein said second antisense compound is targeted to a different connexin than a first antisense compound.

Connexin targets will vary depending upon the type of tissue to be engineered or remodeled and the precise sequence of the antisense polynucleotide used in the invention will depend upon the target connexin protein. The connexin protein or proteins targeted by the oligonucleotides will be dependent upon the site at which downregulation is to be directed. This reflects the nonuniform make-up of gap junction (s) at different sites throughout the body in terms of connexin sub-unit composition. Some connexin proteins are however more ubiquitous than others in terms of distribution in tissue. As described herein, cornea-associated connexins such as connexin 43 are preferred in some embodiments. Therefore, in the context of the invention, oligonucleotides either alone or in combination, targeted towards connexin 43, 26, 37, 30 and/or 31.1 (e.g. see SEQ. ID. NOS: 1-11) which are suitable for corneal engineering or remodeling application. In one aspect of the invention, the oligodeoxynucleotides may be unmodified phosphodiester oligomers. In another aspect of the invention, the polynucleotides may be single or double stranded.

It is also contemplated that oligonucleotides targeted at separate connexin proteins may be used in combination (for example one, two, three, four or more different connexins may be targeted). For example, ODNs targeted to connexin 43, and one or more other members of the connexin family (such as connexin 26, 30, 31.1, 37 and 43) can be used in combination. It is also contemplated that individual antisense polynucleotides may be specific to a particular connexin, or may target 1, 2, 3 or more different connexins. Specific polynucleotides will generally target sequences in the connexin gene or mRNA which are not conserved between connexins, whereas non-specific polynucleotides will target conserved sequences. Thus, in certain embodiments, antisense compounds are targeted to at least 8 nucleobases of a nucleic acid molecule encoding human connexin 26, connexin 30, connexin 31.1, human connexin 37, connexin 43, wherein said antisense compound inhibits the expression of a human connexin protein in cells associated with the eye of said patient.

In certain embodiments, the nucleic acid molecules encoding a connexin have a nucleobase sequence selected from SEQ. ID NO:12-31. In certain embodiments, the compositions target two or more human connexin proteins and inhibit the expression of two or more human connexin proteins. In further certain embodiments, the antisense compounds are antisense oligonucleotides. Exemplary antisense oligonucleotide to connexin 43 selected include GTA ATT GCG GCA AGA AGA ATT GTT TCT GTC (SEQ ID NO: 1); GTA ATT GCG GCA GGA GGA ATT GTT TCT GTC (SEQ ID NO: 2); and GGC AAG AGA CAC CAA AGA CAC TAC CAG CAT (SEQ ID NO: 3). An example of an antisense oligonucleotide to connexin 26 has the sequence TCC TGA GCA ATA CCT AAC GAA CAA ATA (SEQ ID NO: 4). Exemplary antisense oligonucleotide to connexin 37 selected include 5' CAT CTC CTT GGT GCT CAA CC 3' (SEQ ID NO: 5) and 5' CTG AAG TCG ACT TGG CTT GG 3' (SEQ ID NO: 6). Exemplary antisense oligonucleotide to connexin 30 selected include 5' CTC AGA TAG TGG CCA GAA TGC 3' (SEQ ID NO: 7) and 5' TTG TCC AGG TGA CTC CAA GG 3' (SEQ ID NO: 8). Exemplary antisense oligonucleotide to connexin 31.1 selected include 5' CGT CCG AGC CCA GAA AGA TGA GGT C 3'(SEQ ID NO: 9); 5' AGA GGC GCA CGT GAG ACA C 3' (SEQ ID NO: 10); and 5' TGA AGA CAA TGA AGA TGT T 3'(SEQ ID NO: 11).

In a further embodiment, oligodeoxynucleotides selected from the following sequences are particularly suitable for down-regulating connexin43 expression:

```
                                          (SEQ ID NO: 1)
5' GTA ATT GCG GCA AGA AGA ATT GTT TCT GTC 3'

(SEQ ID NO: 2)
5' GTA ATT GCG GCA GGA GGA ATT GTT TCT GTC 3';
and (SEQ ID NO: 3)
5' GGC AAG AGA CAC CAA AGA CAC TAC CAG CAT 3'
```

In yet another embodiment, oligodeoxynucleotides selected from the group following sequences are particularly suitable for connexins 26, 37, 30, and 31.1:

```
(connexin26)
                                          (SEQ ID NO: 4)
5' TCC TGA GCA ATA CCT AAC GAA CAA ATA 3'

(connexin37)
                                          (SEQ ID NO: 5)
5' CAT CTC CTT GGT GCT CAA CC 3'

(connexin37)
                                          (SEQ ID NO: 6)
5' CTG AAG TCG ACT TGG CTT GG 3'

(connexin30)
                                          (SEQ ID NO: 7)
5' CTC AGA TAG TGG CCA GAA TGC 3'

(connexin30)
                                          (SEQ ID NO: 8)
5' TTG TCC AGG TGA CTC CAA GG 3'

(connexin31.1)
                                          (SEQ ID NO: 9)
5' CGT CCG AGC CCA GAA AGA TGA GGT C 3'

(connexin31.1)
                                          (SEQ ID NO: 10)
5' AGA GGC GCA CGT GAG ACA C 3'

(connexin31.1)
                                          (SEQ ID NO: 11)
5' TGA AGA CAA TGA AGA TGT T 3'
```

The antisense compounds provided herein generally comprise from about 8 to about 40 nucleobases (i.e. from about 8 to about 40 linked nucleosides), and more typically those comprising from about 12 to about 40 nucleobases, and even more typically about 30 nucleobases. Antisense compounds comprising polynucleotides may be at least about 40, for example at least about 60 or at least about 80, nucleotides in length and up to 100, 200, 300, 400, 500, 1000, 2000 or 3000 or more nucleotides in length. Suitable antisense compounds include, for example, a 30 mer ODN.

In certain embodiments, antisense compounds are targeted to at least about 8 nucleobases of a nucleic acid molecule encoding a connexin having a nucleobase sequence selected from SEQ ID NO:12-31. In other embodiments, the antisense compound is targeted to at least about 10, at least about 12, at least about 14, at least about 16, at least about 18, at least about 20, at least about 25, at least about 30, and at least about 35 nucleobases of a nucleic acid molecule encoding a connexin having a nucleobase sequence selected from SEQ ID NO:12-31. The size of the antisense compounds, including oligonucleotides targeted to between at least about 8 and 35 nucleobases of a nucleic acid molecule encoding a human connexin, may be 8 nucleobases in length or longer, between 8 and 100 nucleobases, between eight and 50 nucleobases, between eight and 40 nucleobases, between 10 and 50 nucleobases, between 12 and 50 nucleobases, between 14 and 50 nucleobases, between 16 and 50 nucleobases, between 18 and 50 nucleobases, between 20 and 50 nucleobases, between 25 and 50 nucleobases, between 15 and 35 nucleobases in length, and the like. Other antisense compounds of the invention may be or smaller or larger is size, for example having more than 100 nucleobases in length.

Antisense compounds include antisense oligonucleotides (ODN), antisense polynucleotides, deoxyribozymes, morpholino oligonucleotides, RNAi molecules or analogs thereof, siRNA molecules or analogs thereof, PNA molecules or analogs thereof, DNAzymes or analogs thereof, 5'-end-mutated U1 small nuclear RNAs and analogs thereof.

As provided herein, the antisense compound may include the use of oligodeoxynucleotides (ODNs). ODNs are generally about 20 nucleotides in length and act by hybridizing to pre-mRNA and mRNA to produce a substrate for ribonuclease H (RNase H), which specifically degrades the RNA strand of the formed RNA-DNA duplexes. If modified in a way to prevent the action of RNase H, ODNs can inhibit translation of mRNA via steric hindrance, or inhibit splicing of pre-mRNAs. ODNs and modifications thereof have been used to target dsDNA for the inhibition of transcription by the formation of triple helices. ODN may be obtained by art recognized methods of automated synthesis and it is relatively straightforward to obtain ODNs of any sequence and to block gene expression via antisense base pairing.

In certain aspects, the phosphodiester backbone of ODNs can be modified to increase their efficacy as target-specific agents for blocking gene expression. These backbone modifications were developed to improve the stability of the ODNs and to enhance their cellular uptake. The most widely used modification is one in which the nonbridging oxygen is replaced by a sulfur atom, creating phosphorothioate ODNs. At least one phosphorothioate ODN has been approved by the FDA, and several other phosphorothioate antisense ODNs are in earlier stages of clinical trials for a variety of cancers and inflammatory diseases.

The mechanisms of action of ODNs with respect to blocking gene function vary depending upon the backbone of the ODN (Branch, A. D. Hepatology 24, 1517-1529 (1996); Dias, N. and Stein, C. A. Mol. Cancer Thor. 1, 347-355 (2002); Stein, C. A. and Cohen, J. S., Cancer Res. 48, 2659-2668 (1988); Zon, G. Ann. N.Y. Acad Sci., 616, 161-172 (1990). Net negatively charged ODNs, such as phosphodiesters and phosphorothioates, elicit RNAse H-mediated cleavage of the target mRNA. Other backbone modifications that do not recruit RNAse H, because of their lack of charge or the type of helix formed with the target RNA, can be classified as steric hindrance ODNs. Popularly used members of this latter group include morpholinos, U-O-methyls, 2"-O-allyls, locked nucleic acids and peptide nucleic acids (PNAs). These ODNs can block splicing, translation, nuclear-cytoplasmic transport and translation, among other inhibition targets.

In another aspect, modulation of the connexin expression involves the use of ribozymes. Ribozymes are RNA molecules that act as enzymes, even in the complete absence of proteins. They have the catalytic activity of breaking and/or forming covalent bonds with extraordinary specificity, thereby accelerating the spontaneous rates of targeted reactions by many orders of magnitude.

Ribozymes bind to RNA through Watson-Crick base pairing and act to degrade target RNA by catalysing the hydrolysis of the phosphodiester backbone. There are several different classes of ribozymes, with the 'hammerhead' ribozyme being the most widely studied. As its name implies, the hammerhead ribozyme forms a unique secondary structure when hybridized to its target mRNA. The catalytically important residues within the ribozyme are flanked by target-complementary sequences that flank the target RNA cleavage site. Cleavage by a ribozyme requires divalent ions, such as magnesium, and is also dependent on target RNA structure and accessibility. Co-localizing a ribozyme with a target RNA within the cell through the use of localization signals greatly increases their silencing efficiency. The hammerhead ribozymes are short enough to be chemically synthesized or can be transcribed from vectors, allowing for the continuous production of ribozymes within cells.

The ability of RNA to serve as a catalyst was first demonstrated for the self-splicing group I intron of *Tetrahymena thermophila* and the RNA moiety of RNAse. After the discovery of these two RNA enzymes, RNA-mediated catalysis has been found associated with the self-splicing group II introns of yeast, fungal and plant mitochondria (as well as chloroplasts) single-stranded plant viroid and virusoid RNAs, hepatitis delta virus and a satellite RNA from *Neurospora crassa* mitochondria. Ribozymes occur naturally, but can also be artificially engineered for expression and targeting of specific sequences in cis (on the same nucleic acid strand) or trans (a noncovalently linked nucleic acid). New biochemical activities are being developed using in vitro selection protocols as well as generating new ribozyme motifs that act on substrates other than RNA.

The group I intron of *T. thermophila* was the first cis-cleaving ribozyme to be converted into a trans-reacting form, which we refer to as an intron/ribozyme, making it useful both in genomic research and as a possible therapeutic. In the trans-splicing reaction, a defective exon of a targeted mRNA can be exchanged for a correct exon that is covalently attached to the intron/ribozyme. This occurs via a splicing reaction in which the exon attached to the intron is positioned by base pairing to the target mRNA so that it can be covalently joined to the 5" end of the target transcript in a transesterification reaction. This reaction has been used to trans-splice wild-type sequences into sickle cell globin transcripts and mutant p53 transcripts and replace the expanded triplets in the 3"-UTR of protein kinase transcripts in a myotonic dystrophy allele.

The endoribonuclease RNAse P is found in organisms throughout nature. This enzyme has RNA and one or more protein components depending upon the organism from which it is isolated. The RNA component from the *Escherichia coli* and *Bacillus subtilis* enzymes can act as a site-specific cleavage agent in the absence of the protein trader certain salt and ionic conditions. Studies of the substrate requirements for human and bacterial enzymes have shown that the minimal substrates for either enzyme resemble a segment of a transfer RNA molecule. This structure can be mimicked by uniquely designed antisense RNAs, which pair to the target RNA, and serve as substrates for RNAse P-mediated, site-specific cleavage both in the test tube and in cells. It has also been shown that the antisense component can be covalently joined to the RNAse P RNA, thereby directing the enzyme only to the target RNA of interest. Investigators have taken advantage of this property in the design of antisense RNAs, which pair with target mRNAs of interest to stimulate site-specific cleavage of the target and for targeted inhibition of both herpes simplex virus and cytomegalovirus in cell culture.

A number of small plant pathogenic RNAs (viroids, satellite RNAs and virusoids), a transcript from a *N. crassa* mitochondrial DNA plasmid and the animal hepatitis delta virus undergo a self-cleavage reaction in vitro in the absence of protein. The reactions require neutral pH and $Mg^{2+}$. The self-cleavage reaction is an integral part of the in vivo rolling circle mechanism of replication. These self-cleaving RNAs can be subdivided into groups depending on the sequence and secondary structure formed about the cleavage site. Small ribozymes have been derived from a motif found in single-stranded plant viroid and virusoid RNAs. On the basis of a shared secondary structure and a conserved set of nucleotides, the term "hammerhead" has been given to one group of this self-cleavage domain. The hammerhead ribozyme is composed of 30 nucleotides. The simplicity of the hammerhead catalytic domain has made it a popular choice in the design of trans-acting ribozymes. Using Watson-Crick base pairing, the hammerhead ribozyme can be designed to cleave any target RNA. The requirements at the cleavage site are relatively simple, and virtually any UH sequence motif (where H is U, C or A) can be targeted.

A second plant-derived, self-cleavage motif, initially identified in the negative strand of the tobacco ringspot satellite RNA, has been termed the 'hairpin' or "paperclip." The hairpin ribozymes cleave RNA substrates in a reversible reaction that generates 2", Y-cyclic phosphate and 5"-hydroxT1 termini-engineered versions of this catalytic motif also cleave and turn over multiple copies of a variety of targets in trans. Substrate requirements for the hairpin include a GUC, with cleavage occurring immediately upstream of the G. The hairpin ribozyme also catalyzes a ligation reaction, although it is more frequently used for cleavage reactions.

There have been numerous applications of both hammerhead and hairpin ribozymes in cells for downregulating specific cellular and viral targets. Haseloff and Gerlach designed a hammerhead motif (Haseloff and Gerlach; Nature. 1988 Aug. 18; 334(6183):585-91) that can be engineered to cleave any target by modifying the arms that base pair with right target. Ramemzani et al. demonstrated that this hammerhead ribozyme motif had potential therapeutic applications in a study in which there was a virtual complete inhibition of viral gene expression and replication using cells engineered to express an anti-human immunodeficiency virus (HIV) gag ribozyme (Ramezani A. et al., *Frontiers in Bioscience* 7:a, 29-36; 2002).

In another aspect, modulation of the connexin expression involves the use of catalytic DNAs (or DNAzymes). Small DNAs capable of site specifically cleaving RNA targets have been developed via in vitro evolution (as no known DNA enzymes occur in nature). Two different catalytic motifs, with different cleavage site specificities have been identified. The most commonly used 10-20 enzymes bind to their RNA substrates via Watson-Crick base pairing and site specifically cleave the target RNA, as do the hammerhead and hairpin ribozymes, resulting in 2; 3"-cyclic phosphate and 5"-OH termini. Cleavage of the target mRNAs results in their destruction and the DNAzymes recycle and cleave multiple substrates. Catalytic DNAs are relatively inexpensive to synthesize and have good catalytic properties, making them useful substitutes for either antisense DNA or ribozymes.

Several applications of DNAzymes in cell culture have been published including the inhibition of veg FmRNA and consequent prevention of angiogenesis, and inhibition of expression of the bcr/abl fusion transcript characteristic of chronic myelogenous leukemia. Catalytic DNAs can be delivered exogenously, and they can be backbone-modified to in order to optimize systemic delivery in the absence of a carrier.

In another aspect of the present invention, the modulation of the constitutive connexin gene involves the use of oligonucleotides having morpholino backbone structures. Summerton, J. E. and Weller, D. D. U.S. Pat. No. 5,034,506.

In another aspect of the invention, the antisense polynucleotides may be chemically modified in order to enhance their resistance to nucleases and increase the efficacy of cell entry. For example, mixed backbone oligonucleotides (MBOs) containing segments of phosphothioate oligodeoxynucleotides and appropriately placed segments of modified oligodeoxyor oligoribonucleotides may be used. MBOs have segments of phosphorothioate linkages and other segments of other modified oligonucleotides, such as methylphosphonates, phosphoramidates, phosphorodithioates, N3'P5'-phosphoramidates and oligoribonucleotide phosphorothioates and their 2'-O-alkyl analogs and 2'-O-methylribonucleotide methylphosphonates, which are non-ionic, and very resistant to nucleases or 2'-O-alkyloligoribonucleotides.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

The antisense compounds useful in this invention may include oligonucleotides containing modified backbones or non-natural internucleoside linkages. Oligonucleotides having modified backbones include those that retain a phosphorus atom in the backbone and those that do not have a phosphorus atom in the backbone. In the context of this invention, modified oligonucleotides that do not have a phosphorus atom in their internucleoside backbone can also be considered to be oligonucleosides.

The antisense compounds with modified oligonucleotide backbones useful in this invention may include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

In one aspect, it is contemplated that modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

In one aspect, it is contemplated that oligonucleotide mimetics, both the sugar and the internucleoside linkage, i. e. the backbone of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Further teaching of PNA compounds can be found in Nielsen et al. (Science, 1991, 254, 1497-1500).

In one aspect, oligonucleotides with phosphorothioate backbones and oligonucleosides with heteroatom backbones, and in particular —CH2-NH—O—CH2-, —CH-2 N(CH)3-O—CH-2 [known as a methylene (methylimino) or MMI backbone], —CH2-O—N(CH3)-CH2-, —CH2-N (CH3)-N(CH3)-CH2- and —O—N(CH3)-CH2-CH2- [wherein the native phosphodiester backbone is represented as —O—P—O—CH2-] are contemplated. In yet another aspect, oligonucleotides having morpholino and amide backbone structures are also contemplated.

In another aspect, it is contemplated that the modified oligonucleotides may also contain one or more substituted sugar moieties. For example, oligonucleotides comprising one of the following at the 2' position: OH; F; O-, S-, or N-alkyl, O-alkyl-O-alkyl, O-, S-, or N-alkenyl, or O-, S- or N-alkynyl, wherein the alkyl, alkenyl and alkynyl may be substituted or unsubstituted C1 to C10 alkyl or C2 to C10 alkenyl and alkynyl. Particularly preferred are O[(CH2)n O]m CH3, O(CH2)n OCH3, O(CH2)2 ON(CH3)2, O(CH2)n NH2, O(CH2)n CH3, O(CH2)n ONH2, and O(CH2)n ON[(CH2)n CH3)]2, where n and m are from 1 to about 10. Other preferred oligonucleotides may comprise one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2 CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH2 CH2 OCH,3 also known as 2'-O-(2-methoxyethyl)

or 2'-MOE) (Martin et al. Helv. Chim. Acta 1995, 78, 486-504) i.e. an alkoxyalkoxy group. Other modification includes 2'-dimethylaminooxyethoxy, i.e., a O(CH2)2 ON(CH3). 2 group, also known as 2'-DMAOE, and 2'-dimethylamino-ethoxyethoxy (2'-DMAEOE), i.e., 2'-O—CH2-O-CH2-N(CH2)2.

It is further contemplated that the modifications may include 2'-methoxy (2'-O—CH3), 2'-aminopropoxy (2'-OCH2 CH2 CH2 NH2) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

In another aspect, it is contemplated that the oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the Concise Encyclopedia Of Polymer Science And Engineering 1990, pages 858-859, Kroschwitz, J. John Wiley & Sons, those disclosed by Englisch et al. (Angewandte Chemie, International Edition 1991, 30, 613-722), and those disclosed by Sanghvi, Y. S., Chapter 15, Antisense Research and Applications 1993, pages 289-302, Crooke, S. T. and Lebleu, B., ed., CRC Press. Certain of these nucleobases are particularly useful for increasing the binding affinity of the oligomeric compounds. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications 1993, CRC Press, Boca Raton, pages 276-278) and are presently preferred base substitutions, even more particularly when combined with 2'-O-methoxyethyl sugar modifications.

In another aspect, it is contemplated that the modification of the oligonucleotides involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA 1989, 86, 6553-6556), cholic acid (Manoharan et al., Bioorg. Med. Chem. Lett. 1994, 4, 1053-1059), a thioether, e.g., hexyl-S-tritylthiol (Manoharan et al., Ann. N.Y. Acad. Sci. 1992, 660, 306-309; Manoharan et al., Bioorg. Med. Chem. Let. 1993, 3, 2765-2770), a thiocholesterol (Oberhauser et al., Nucl. Acids Res. 1992, 20, 533-538), an aliphatic chain, e.g., dodecandiol or undecyl residues (Saison-Behmoaras et al., EMBO J. 1991, 10, 1111-1118; Kabanov et al., FEBS Lett. 1990, 259, 327-330; Svinarchuk et al., Biochimie 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett. 1995, 36, 3651-3654; Shea et al., Nucl. Acids Res. 1990, 18, 3777-3783), a polyamine or a polyethylene glycol chain (Manoharan et al., Nucleosides & Nucleotides 1995, 14, 969-973), or adamantane acetic acid (Manoharan et al., Tetrahedron Lett. 1995, 36, 3651-3654), a palmityl moiety (Mishra et al., Biochim. Biophys. Acta 1995, 1264, 229-237), or an octadecylamine or hexylamino-carbonyl-oxycholesterol moiety (Crooke et al., J. Pharmacol. Exp. Ther. 1996, 277, 923-937).

Also contemplated are the use of oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g. fluoro- or 2'-O-methoxyethyl-substituted). Chimeric oligonucleotides are not limited to those with modifications on the sugar, but may also include oligonucleosides or oligonucleotides with modified backbones, e.g., with regions of phosphorothioate (P=S) and phosphodiester (P=O) backbone linkages or with regions of MMI and P=S backbone linkages. Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa. In one embodiment, the oligonucleotides of the present invention contain a 2'-O-methoxyethyl (2'-O—CH2 CH2 OCH3) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides may bear a 2'-O-methoxyethyl (—O—CH2 CH2 OCH3) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 21-O-methoxyethyl modifications, oligonucleotides containing other modifications which enhance antisense efficacy, potency or target affinity are also contemplated.

The present invention also provides polynucleotides (for example, DNA, RNA, PNA or the like) that bind to double-stranded or duplex connexin nucleic acids (for example, in a folded region of the connexin RNA or in the connexin gene), forming a triple helix-containing, or "triplex" nucleic acid. Triple helix formation results in inhibition of connexin expression by, for example, preventing transcription of the connexin gene, thus reducing or eliminating connexin activity in a cell. Without intending to be bound by any particular mechanism, it is believed that triple helix pairing compromises the ability of the double helix to open sufficiently for the binding of polymerases, transcription factors, or regulatory molecules to occur.

Triplex oligo- and polynucleotides are constructed using the base-pairing rules of triple helix formation (see, for example, Cheng et al., J. Biol. Chem. 263: 15110 (1988); Ferrin and Camerini-Otero, Science 354:1494 (1991); Ramdas et al., J. Biol. Chem. 264:17395 (1989); Strobel et al., Science 254:1639 (1991); and Rigas et al., Proc. Natl. Acad. Sci. U.S.A. 83: 9591 (1986)) and the connexin mRNA and/or gene sequence. Typically, the triplex-forming oligonucleotides comprise a specific sequence of from about 10 to about 25 nucleotides or longer "complementary" to a specific sequence in the connexin RNA or gene (i.e., large enough to form a stable triple helix, but small enough, depending on the mode of delivery, to administer in vivo, if desired). In this context, "complementary" means able to form a stable triple helix. In one embodiment, oligonucleotides are designed to bind specifically to the regulatory regions of the connexin gene (for example, the connexin 5'-flanking sequence, promoters, and enhancers) or to the transcription initiation site, (for example, between −10 and +10 from the transcription initiation site). For a review of recent therapeutic advances using triplex DNA, see Gee et al., in Huber and Carr, 1994, Molecular and Immunologic Approaches, Futura Publishing Co, Mt Kisco NY and Rininsland et al., 1997, *Proc. Natl. Acad. Sci. USA* 94:5854.

The present invention also provides ribozymes useful for inhibition of connexin activity. The ribozymes bind and specifically cleave and inactivate connexin mRNA. Useful ribozymes can comprise 5'- and 3'-terminal sequences complementary to the connexin mRNA and can be engineered by one of skill on the basis of the connexin mRNA sequence. It is contemplated that ribozymes provided herein include those having characteristics of group I intron ribozymes (Cech, *Biotechnology* 13:323 (1995)) and others of hammerhead ribozymes (Edgington, *Biotechnology* 10:256 (1992)).

Ribozymes include those having cleavage sites such as GUA, GUU and GUC. Short RNA oligonucleotides between 15 and 20 ribonucleotides in length corresponding to the region of the target connexin gene containing the cleavage site can be evaluated for secondary structural features that may render the oligonucleotide more desirable. The suitability of cleavage sites may also be evaluated by testing accessibility to hybridization with complementary oligonucleotides using ribonuclease protection assays, or by testing for in vitro ribozyme activity in accordance with standard procedures known in the art.

Further contemplated are antisense compounds in which antisense and ribozyme functions can be combined in a single oligonucleotide. Moreover, ribozymes can comprise one or more modified nucleotides or modified linkages between nucleotides, as described above in conjunction with the description of illustrative antisense oligonucleotides provided herein.

The present invention also provides polynucleotides useful for inhibition of connexin activity by methods such as RNA interference (RNAi) This and other techniques of gene suppression are well known in the art. A review of this technique is found in Science 288:1370-1372 (2000). RNAi operates on a post-transcriptional level and is sequence specific. The process comprises introduction of RNA with partial or fully double-stranded character, or precursors of or able to encode such RNA into the cell or into the extracellular environment.

As described by Fire et al., U.S. Pat. No. 6,506,559, the RNA may comprise one or more strands of polymerized ribonucleotide. The double-stranded structure may be formed by a single self-complementary RNA strand or two complementary RNA strands. The RNA may include modifications to either the phosphate-sugar backbone or the nucleosides. RNA duplex formation may be initiated either inside or outside the cell.

Studies have demonstrated that one or more ribonucleases specifically bind to and cleave double-stranded RNA into short fragments. The ribonuclease(s) remains associated with these fragments, which in turn specifically bind to complementary mRNA, i.e., specifically bind to the transcribed mRNA strand for the connexin gene. The mRNA for the connexin gene is also degraded by the ribonuclease(s) into short fragments, thereby obviating translation and expression of the connexin gene, and so inhibiting connexin activity. Additionally, an RNA polymerase may act to facilitate the synthesis of numerous copies of the short fragments, which exponentially increases the efficiency of the system. A unique feature of this gene suppression pathway is that silencing is not limited to the cells where it is initiated. The gene-silencing effects may be disseminated to other parts of an organism and even transmitted through the germ line to several generations.

In one aspect, the double-stranded (ds)RNA-dependent gene specific post transcriptional silencing strategy of RNAi involves the use of short interfering RNAs (siRNA). The use of the general RNAi approach is subject to certain limitations, including the nonspecific antiviral defense mechanism in mammalian cells activated in response to long dsRNA molecules (Gil J, Esteban M, "Induction of apoptosis by the dsRNA-dependent protein kinase (PKR): Mechanisms of action". Apoptosis 2000, 5:107-114). Advances in the field have been made with the demonstration that synthetic duplexes of 21 nucleotide RNAs could mediate gene specific RNAi in mammalian cells without invoking generic antiviral defense mechanisms (Elbashir S, et al., "Duplexes of 21-nucleotide RNAs mediate RNA interference in cultured mammalian cells". Nature 2001, 411:494-498; Caplen N. et al., Proc Natl Acad Sci 2001, 98:9742-9747). Thus, siRNAs are increasingly being recognized as powerful tools for gene-specific modulation.

As described herein, RNAi includes to a group of related gene-silencing mechanisms sharing many common biochemical components in which the terminal effector molecule is for example, but not limited to, a small 21-23-nucleotide antisense RNA. One mechanism uses a relatively long, dsRNA 'trigger; which is processed by the cellular enzyme Dicer into short, for example, but not limited to, 21-23-nucleotide dsRNAs, referred to as siRNAs. The strand of the siRNA complementary to the target RNA becomes incorporated into a multi-protein complex termed the RNA-induced silencing complex (RISC), where it serves as a guide for endonucleolytic cleavage of the mRNA strand within the target site. This leads to degradation of the entire mRNA; the antisense siRNA can then be recycled. In lower organisms, RNA-dependent RNA polymerase also uses the annealed guide siRNA as a primer, generating more dsRNA front the target, which serves in turn as a Dicer substrate, generating more siRNAs and amplifying the siRNA signal. This pathway is commonly used as a viral defense mechanism in plants.

As described herein, the siRNA may consist of two separate, annealed single strands of for example, but not limited to, 21-23 nucleotides, where the terminal two 3"-nucleotides are unpaired (3" overhang). Alternatively, the siRNA may be in the form of a single stem-loop, often referred to as a short hairpin RNA (shRNA). Typically, but not always, the antisense strand of shRNAs is also completely complementary to the sense partner strand of the si/shRNA.

In mammalian cells, long dsRNAs (usually greater than 30 nucleotides in length) trigger the interferon pathway, activating protein kinase R and 2; 5"-oligoadenylate synthetase. Activation of the interferon pathway can lead to global downregulation of translation as well as global RNA degradation. However, shorter siRNAs exogenously introduced into mammalian cells have been reported to bypass the interferon pathway.

The siRNA antisense product can also be derived from endogenous microRNAs. In human cells, regardless of the initial form (siRNAs and microRNAs) or processing pathway, a final mature for example, but not limited to, 21-23-nucleotide antisense RNA that is completely homologous to the mRNA will direct mRNA cleavage. In general, the effect of mismatches between siRNAs and target sites can vary from almost none to complete abrogation of activity, for reasons that are only partially understood; however, in at least one case, partial homology resulted in mRNA translation inhibition. In general, siRNA with target mismatches designed to mimic a prototypical microRNA-target interaction can mediate varying degrees of translational repression, depending on both the specific interaction and the number of target sites in the mRNA. RNAi can be activated by either exogenous delivery of preformed siRNAs or via promoter-based expression of siRNAs or shRNAs.

Short interfering RNAs (siRNA) can be chemically synthesized or generated by DNA-based vectors systems. In general, this involves transcription of short hairpin (sh) RNAs that are efficiently processed to form siRNAs within cells (Paddison P, Caudy A, Hannon G: Stable suppression of gene expression by RNAi in mammalian cells. *Proc Natl Acad Sci USA* 2002, 99:1443-1448; Paddison P, Caudy A, Bernstein E, Hannon G, Conklin D: Short hairpin RNAs (shRNAs) induce sequence-specific silencing in mammalian cells. *Genes & Dev* 2002, 16:948-958; Sui G, et al., *Proc Natl Acad Sci* 2002, 8:5515-5520; Brummelkamp T, et al., *Science* 2002, 296:550-553). Therefore, in the context, siRNAs can be employed as an effective strategy for the tissue-specific targeting and modulation of gene expression.

The oligonucleotides used in accordance with this invention may be conveniently and routinely made through the well-known technique of solid phase synthesis. Equipment for such synthesis is sold by several vendors known in the art. Any other means for such synthesis may also be employed; the actual synthesis of the oligonucleotides is well recognized in the art. It is well known to use similar techniques to prepare oligonucleotides such as the phosphorothioates and 2'-alkoxy or 21-alkoxyalkoxy derivatives, including 2'-O-methoxyethyl oligonucleotides (Martin, P. Helv. Chim. Acta 1995, 78, 486-504). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

Methods

In another aspect, the invention includes methods of treating a subject (e.g. patient) by administering antisense compounds to the subject. Generally, these methods include methods for tissue engineering and methods for reducing tissue damage associated with medical procedures, including but not limited to ophthalmic procedures.

The method may comprise, for example, administering an antisense compound to the eye of said subject in an amount sufficient to inhibit the expression of a human connexin protein in the eye or in cells associated with the eye of the subject. While it is preferred that the expression of human connexin protein is inhibited, it is envisioned that other proteins may be targets for modulation by the antisense compounds, either alone of in combination with antisense compounds which inhibit the expression of human connexins.

In certain embodiments, the ophthalmic procedure is an ophthalmic surgery, including but not limited to an excimer laser photorefractive keratectomy, a cataract extraction, corneal transplant, a surgery to correct refraction, a radial keratotomy, a glaucoma filtration surgery, a keratoplasty, an excimer laser photorefractive keratectomy, a corneal transplant, a surgery to correct refraction, a ocular surface neoplasm excision, a conjunctival or amniotic membrane graft, a pterygium and pingeculae excision, a ocular plastic surgery, a lid tumour excision, a reconstructive lid procedures for congenital abnormalities, an ectropian and entropian eyelid repair, a strabismus surgery (occular muscle), a penetrating eye trauma.

In certain embodiments, antisense compounds provided herein are administered by local or topical administration. Antisense compounds provided herein can also be administered, for example, systemically or by intraocular injection.

Antisense compounds provided herein can be administered to a subject at a predetermined time, for example, relative to the formation of a wound, such as that occurs in an ophthalmic procedure (e.g. surgical). For example, antisense compounds can be administered before an ophthalmic procedure is performed, during an ophthalmic procedure, or after an ophthalmic procedure. For example, antisense compounds may be administered to a subject within minutes or hours before or after an ophthalmic procedure is performed.

In certain embodiments, an antisense compound is administered after an ophthalmic procedure is performed, and for example the antisense compound is administered within about 4 hours of the procedure, within about 3 hours of the procedure, and more typically within about 2 hours of the ophthalmic procedure, or within about 1 hour of an ophthalmic procedure. Alternatively, an antisense compound may be administered within minutes of an ophthalmic procedure, for example within 5, 10, 15, 20, 30, 45, minutes of an ophthalmic procedure. Antisense compounds may also be administered after 4 hours of an ophthalmic procedure.

In another aspect, antisense compounds provided herein may be administered in a methods to effect tissue engineering. In these embodiments, and some others provided herein, antisense compounds are typically administered over a longer periods of time, for example over the course of days, weeks, months, or even longer, and can be administered independent of a particular procedure performed on a patient, such as one performed on an eye.

Antisense compounds provided herein may be administered in conjunction with a method that increases the thickness of cornea tissue in a subject, including in methods that are not associated with an ophthalmic procedure, and in methods in which antisense compounds are administered in association with an ophthalmic procedure (e.g. surgery). Antisense compounds provided herein may be administered in conjunction with a method that promotes healing or prevents tissue damage, for example in cells associated with the cornea of the subject (e.g. corneal cells). Antisense compounds provided herein may be administered in conjunction with a method that reduces scarring in the eye of a subject.

Antisense compounds provided herein may be administered in conjunction with a method that reduces hazing in the eye of a subject. Antisense compounds provided herein may be administered in conjunction with a method that modulates hypercellularity associated with myofibroblast differentiation associated with a site of a laser induced lesion, preferably in the 24 hr to 48 hr post-surgery period. Antisense compounds provided herein may be administered in conjunction with a method that modulates stromal remodeling and reduces haze associated with a site of a laser-induced lesion, preferably in the 24 hr to 72 hr post-surgery period. Antisense compounds provided herein may be administered in conjunction with a method that increases epithelial cell movement in the eye of a subject. Antisense compounds provided herein may be administered in conjunction with a method that results in an increase in epithelial cell movement within 12 hours of administering an antisense compound to the eye of the subject. Antisense compounds provided herein may be administered in conjunction with a method that results in an increase in epithelial cell movement within 24 hours of administering the antisense compound to the eye of the subject. Antisense compounds provided herein may be administered in conjunction with a method that prevents an increase in stromal cell density. Antisense compounds provided herein may be administered in conjunction with a method that inhibits stromal edema associated with a site of a laser-induced lesion in the 24 hr to 72 hr post-surgery period. Antisense compounds provided herein may be administered in conjunction with a method that reduces epithelial hyperplasia in the 24 hr to 72 hr post-surgery. Antisense compounds provided herein may be administered in conjunction with a method that reduces myofibroblast activation up to 1 week post-surgery. Antisense compounds provided herein may be administered in conjunction with a method that modulates cell differentiation that modifies the extracellular matrix. Antisense compounds provided herein may be administered in conjunction with a method that reduces cell proliferation.

In certain embodiments, the antisense compound decreases scar formation. In certain embodiments, the antisense compound reduces inflammation. In certain embodiments, the antisense compound promotes wound healing. In certain preferred embodiments, the antisense compound is used in association with a surgical implantation procedure. In certain preferred embodiments, the antisense compound is directed to connexin 43 and is administered to regulate epithelial basal cell division and growth. In certain embodiments, the antisense compound is directed to connexin 31.1 and is administered to regulate outer layer keratinisation.

In other embodiments, the method promotes healing or prevents tissue damage in cells associated with the cornea of the subject. According to certain embodiment, antisense compounds are used in methods that increase the thickness of cornea tissue in a subject, or in a method that results in the reduction of tissue damage in corneal cells of a subject, or in a method that results in the reduction of tissue damage in cells associated with the cornea of a subject, or in a method performed in association with an excimer laser photorefractive keratectomy procedure in a subject, or in a method that modulates hypercellularity associated with myofibroblast differentiation associated with a site of a laser induced lesion, preferably in the 24 hr to 48 hr post-surgery period, or in a method that modulates stromal remodeling and reduces haze associated with a site of a laser-induced lesion, preferably in the 24 hr to 72 hr post-surgery period, or in a method that inhibits stromal edema associated with a site of a laser induced lesion in the 24 hr to 72 hr post-surgery period, or in a method that reduces epithelial hyperplasia, preferably in the 24 hr to 72 hr post-surgery, or in a method that reduces myofibroblast activation up to 1 week post-surgery, or in a method that modulates cell differentiation that modifies the extracellular matrix, or in a method that reduces cell proliferation.

In certain embodiments, the ophthalmic procedure is cataract extraction. In a other embodiments, the ophthalmic procedure is a corneal transplant. In other embodiments, the ophthalmic surgical procedure is surgery to correct refraction. In a other embodiments, the ophthalmic procedure is radial keratotomy. In a other embodiments, the ophthalmic procedure is glaucoma filtration surgery. In still other embodiments, the ophthalmic procedure is keratoplasty.

In certain embodiments, the antisense compound or composition is administered by local or topical administration. In certain embodiments, the antisense compound or composition is administered by direct application in the surgical wound. In certain embodiments, the antisense compound or composition is administered by intraocular injection. In certain embodiments, the antisense compound or composition is administered before the surgical procedure is performed. In certain embodiments, the antisense compound or composition is administered during the surgical procedure. In certain non-limiting embodiments, the antisense compound or composition is administered within about 15 minutes before an ophthalmic procedure is performed or up to about 2 hours after an ophthalmic procedure is performed. In certain other embodiments, for example for tissue engineering, antisense compounds provided herein may be administered for days or even months.

In certain further embodiments, compounds and compositions are used to promote healing or to prevent tissue damage in cells associated with cornea, where the cells associated with the cornea may be any cell in the eye, including but not limited to corneal cells. The agents provided herein, including antisense compounds, may increase the thickness of cornea tissue in a subject. In certain embodiments, the antisense compound is used in combination with another compound useful for reducing tissue damage or promoting healing. For example, the antisense compounds may be coadministered with a growth factor, cytokine, or the like, including but not limited to FGF, NGF, NT3, PDGF, TGF, VEGF, BDGF, EGF, KGF, integrins, interleukins, plasmin, and semaphorins.

In another aspect, a pharmaceutical composition for reducing tissue damage associated with ophthalmic surgery is provided. The pharmaceutical composition is suitably formulated for topical or local administration to the eye of a subject comprising an antisense compound present in an amount sufficient to inhibit the expression of a human connexin protein in cells associated with the eye of the subject. The antisense compound is preferably targeted to at least about 8 nucleobases of a nucleic acid molecule encoding a connexin having a nucleobase sequence selected from SEQ ID NO:12-31. In certain embodiments, the antisense compounds are in the form of a pharmaceutical composition comprising a pharmaceutically acceptable carrier or vehicle and the agent or antisense compound is present in an amount effective to promote wound healing in a subject. In certain embodiments, the pharmaceutical compositions may be, for example, in a form suitable for topical administration, including in a form suitable for topical or local administration to the eye of a subject. In certain further embodiments, the compositions and formulations may be in the form of a gel, a cream, or any of the forms described herein.

In another aspect, methods of treating an injury to the central nervous system are provided. The method comprising administering an antisense compound to a site proximal to a preexisting wound of the central nervous system in association with a surgical procedure performed on a patient to treat said injury to the central nervous system, wherein said antisense compound is targeted to at least about 8 nucleobases of a nucleic acid molecule encoding a connexin having a nucleobase sequence selected from SEQ ID NO:12-31. In certain embodiments of the method, the antisense compound is administered to reduce neuronal loss due to physical trauma to the spinal cord. In certain embodiments of the method, the antisense compound is administered to a site adjacent to a wound that is the result of trauma. In certain embodiments of the method, the antisense compound is administered to a site adjacent to a wound that is the result of a surgery. In certain embodiments of the method, the antisense compound is administered to a site adjacent to a spinal cord injury. In certain embodiments of the method, the antisense compound is directed to connexin 43 and is administered to regulate epithelial basal cell division and growth. In certain embodiments of the method, the antisense compound promotes wound healing. In certain embodiments of the method, the antisense compound reduces inflammation. In certain embodiments of the method, the antisense compound decreases scar formation. In certain embodiments of the method, the injury to the central nervous system is a spinal cord injury. In certain embodiments of the method, the antisense compound is administered to a patient at least about 24 hours after a physical trauma to the spinal cord. In certain embodiments of the method, the antisense compound is used in association with a surgical implantation procedure. In certain further embodiments of the method, the surgical implantation procedure is associated with an implant pre-treated with antisense-compound to promote wound healing. In another aspect, antisense compounds capable of promoting the regeneration of neurons in association with a procedure for the treatment of a preexisting wound in a patient character-ized by neuronal loss are provided. In certain embodiments, the agents are antisense compounds up to 40 nucleobases in length that are targeted to at least about 8 nucleobases of a nucleic acid molecule encoding a human connexin and the antisense compound inhibits the expression of one or more human connexin in association with a procedure to promote the regeneration neurons for the treatment of a preexisting wound in a patient. The wound includes those characterized by neuronal loss. Connexins that may be targeted include connexins having a nucleobase sequence selected from SEQ ID NO:12-31. In these embodiments, the antisense compounds may be administered to a patient at least 24 hours after a physical trauma to the spinal cord of said patient that resulted in a neuronal loss. The antisense compounds may be administered to a patient at more than 24 hours after a physical trauma to the spinal cord for times periods of weeks, months, or years after the physical trauma that resulted in a neuronal loss.

In certain embodiments of pharmaceutical compositions and methods, the antisense compound is targeted to at least about 8 nucleobases of a nucleic acid molecule encoding human connexin 30 or human connexin 37. Preferably, the antisense compound inhibits the expression of a human connexin 30 or 37 protein in cells associated with the eye of a patient. Other pharmaceutical compositions comprise an antisense compound targeted to at least about 8 nucleobases of a nucleic acid molecule encoding a connexin (e.g. human) having a nucleobase sequence selected from SEQ ID NO:12-31, and preferably the antisense compound inhibits the expression of a human connexin in association with a procedure to promote the regeneration neurons for the treatment of a preexisting wound in a patient that is characterized by neuronal loss.

Pharmaceutical Compositions

In another aspect, the invention includes pharmaceutical compositions comprising antisense compounds. In one embodiment, a pharmaceutical composition is provided for reducing tissue damage associated with an ophthalmic procedure (e.g. surgery), such that the pharmaceutical composition is formulated for topical or local administration to the eye of a subject and it comprises an antisense compound present in an amount sufficient to inhibit the expression of a human connexin protein in cells associated with the eye of the subject. In certain embodiments, the antisense compound is targeted to at least about 8 nucleobases of a nucleic acid molecule encoding a connexin (e.g. human) having a nucleobase sequence selected from SEQ ID NO:12-31. In certain embodiments, the pharmaceutical composition includes a pharmaceutically acceptable carrier comprising a buffered pluronic acid or gel, for example up to about 30% pluronic acid in phosphate buffered saline. Antisense composition may comprise different amounts of pluronic acid or gel, including without limitation in amounts up to about 5% pluronic acid in phosphate buffered saline, up to about 10% pluronic acid in phosphate buffered saline, up to about 15% pluronic acid in phosphate buffered saline, up to about 20% pluronic acid in phosphate buffered saline, up to about 25% pluronic acid in phosphate buffered saline, and up to about 30% pluronic acid in phosphate buffered saline.

The antisense compounds provided herein may also include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids and prodrugs of such nucleic acids. "Pharmaceutically acceptable salts" are physiologically and pharmaceutically acceptable salts of the nucleic acids provided herein: i.e., salts that retain the desired biological activity of the parent compound and do not impart undesired toxicological effects thereto (see, for example, Berge et al., J. of Pharma Sci. 1977, 66, 1-19).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides provided herein may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides may be prepared as SATE [(S-acetyl-2-thioethyl) phosphate] derivatives according to the methods disclosed in WO 93/24510 to Gosselin et al., published Dec. 9, 1993.

Antisense compounds may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide.

Pharmaceutical compositions may also include one or more active ingredients such as interferons, antimicrobial agents, anti-inflammatory agents, anesthetics, and the like. Formulations for parenteral administration may include sterile aqueous solutions which may also contain buffers, liposomes, diluents and other suitable additives. Pharmaceutical compositions comprising the oligonucleotides provided herein may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., Critical Reviews in Therapeutic Drug Carrier Systems 1991, 8, 91-192; Muranishi, Critical Reviews in Therapeutic Drug Carrier Systems 1990, 7, 1-33). One or more penetration enhancers from one or more of these broad categories may be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.). Lee et al., Critical Reviews in Therapeutic Drug Carrier Systems 1991, page 92; Muranishi, Critical Reviews in Therapeutic Drug Carrier Systems 1990, 7, 1; El-Hariri et al., J. Pharm. Pharmacol. 1992 44, 651-654).

The physiological roles of bile include the facilitation of dispersion and absorption of lipids and fat-soluble vitamins (Brunton, Chapter 38 In: Goodman & Gilman's The Pharmacological Basis of Therapeutics, 9th Ed., Hardman et al. McGraw-Hill, New York, N.Y., 1996, pages 934-935). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations. Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) [Lee et al., Critical Reviews in Therapeutic Drug Carrier Systems 1991, page 92; Muranishi, Critical Reviews in Therapeutic Drug Carrier Systems 1990, 7, 1-33; Buur et al., J. Control Rel. 1990, 14, 43-51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., Critical Reviews in Therapeutic Drug Carrier Systems 1991, page 92); and perfluorochemical emulsions, such as FC-43 (Takahashi et al., J. Pharm. Pharmacol. 1988, 40, 252-257). Non-surfactants include, for example, unsaturated cyclic ureas, 1-alkyl- and 1-alkenylazacyclo-alkanone derivatives (Lee et al., Critical Reviews in Therapeutic Drug Carrier Systems 1991, page 92); and non-steroidal anti-inflammatory agents such as diclofenac sodium, indomethacin and phenylbutazone (Yamashita et al., J. Pharm. Pharmacol. 1987, 39, 621-626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.).

The compositions provided herein may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions provided herein.

Regardless of the method by which the oligonucleotides are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., Current Op. Biotech. 1995, 6, 698-708).

The antisense polynucleotides may be present in a substantially isolated form. It will be understood that the product may be mixed with carriers or diluents which will not interfere with the intended purpose of the product and still be regarded as substantially isolated. A product may also be in a substantially purified form, in which case it will generally comprise 90%, e.g. at least about 95%, 98% or 99% of the polynucleotide or dry mass of the preparation.

The antisense polynucleotides may be administered topically (at the site to be treated). Preferably the antisense polynucleotides are combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intracerebral, intravenous, subcutaneous, or transdermal administration. Uptake of nucleic acids by mammalian cells is enhanced by several known transfection techniques, for example, those that use transfection agents. The formulation which is administered may contain such agents. Example of these agents include cationic agents (for example calcium phosphate and DEAE-dextran) and lipofectants (for example Lipofectam™ and Transfectam™).

In one aspect, the oligonucleotides may require site-specific delivery. They also require delivery over an extended period of time. While clearly the delivery period will be dependent upon both the site at which the down-regulation is to be induced and the therapeutic effect which is desired, continuous delivery for 24 hours or longer will often be required. In on aspect of the present invention, this is achieved by inclusion of the antisense compounds in a formulation together with a pharmaceutically acceptable carrier or vehicle, particularly in the form of a formulation for topical administration. In particular, topical formulations such as creams, drops, and other described herein can be employed to regulate epithelial basal cell division and growth (using antisense compounds targeted to connexin 43) and outer layer keratinization (using antisense compounds targeted to connexin31.1).

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Compositions for oral administration include powders or granules, suspensions or solutions in water or non-aqueous media, capsules, sachets or tablets. Thickeners, flavoring agents, diluents, emulsifiers, dispersing aids or binders may be desirable. Compositions for parenteral administration may include sterile aqueous solutions which may also contain buffers, diluents and other suitable additives. In some cases it may be more effective to treat a patient with an oligonucleotide in conjunction with other traditional therapeutic modalities in order to increase the efficacy of a treatment regimen. As used herein, the term "treatment regimen" is meant to encompass therapeutic, palliative and prophylactic modalities.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50 s found to be effective in vitro and in in vivo animal models. In general, dosage is from 0.01 mg/kg to 100 mg per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 mg/kg to 100 mg per kg of body weight, once or more daily, to once every 20 years. In the treatment or prevention of conditions which require connexin modulation an appropriate dosage level will generally be about 0.001 to 100 mg per kg patient body weight per day which can be administered in single or multiple doses. Preferably, the dosage level will be about 1 to about 40 mg/kg per day.

The oligonucleotides of this invention can be used in diagnostics, therapeutics, prophylaxis, and as research reagents and in kits. Since the oligonucleotides of this invention hybridize to nucleic acids encoding connexin, sandwich, calorimetric and other assays can easily be constructed to exploit this fact. Provision of means for detecting hybridization of oligonucleotide with the connexin genes or mRNA can routinely be accomplished. Such provision may include enzyme conjugation, radiolabel ling or any other suitable detection systems. Kits for detecting the presence or absence of connexin may also be prepared.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

Exemplary connexins that may be targeted in certain embodiments described herein include, but are not limited to the following.

```
Human Cx 43, α1
LOCUS        NM_000165 3088 bp mRNA linear PRI 26 Oct. 2004
DEFINITION   Homo sapiens gap junction protein, alpha 1, 43 kDa (connexin 43)
             (GJA1), mRNA.
                                                                (SEQ ID NO: 12)
    1        acaaaaaagc ttttacgagg tatcagcact tttctttcat taggggaag gcgtgaggaa
   61        agtaccaaac agcagcggag ttttaaactt taaatagaca ggtctgagtg cctgaacttg
  121        ccttttcatt ttacttcatc ctccaaggag ttcaatcact tggcgtgact tcactacttt
  181        taagcaaaag agtggtgccc aggcaacatg ggtgactgga gcgccttagg caaactcctt
  241        gacaaggttc aagcctactc aactgctgga gggaaggtgt ggctgtcagt acttttcatt
  301        ttccgaatcc tgctgctggg acagcggtt gagtcagcct ggggagatga gcagtctgcc
  361        tttcgttgta acactcagca acctggttgt gaaaatgtct gctatgacaa gtctttccca
  421        atctctcatg tgcgcttctg ggtcctgcag atcatatttg tgtctgtacc cacactcttg
  481        tacctggctc atgtgttcta tgtgatgcga aaggaagaga actgaacaa gaaagaggaa
  541        gaactcaagg ttgcccaaac tgatggtgtc aatgtgaca tgcacttgaa gcagattgag
  601        ataaagaagt tcaagtacgg tattgaagag catggtaagg tgaaaatgcg agggggttg
  661        ctgcgaacct acatcatcag tatcctcttc aagtctatct ttgaggtggc cttcttgctg
  721        atccagtggt acatctatgg attcagcttg agtgctgttt acacttgcaa aagagatccc
  781        tgcccacatc aggtggactg tttcctctct cgccccacgg agaaaaccat cttcatcatc
  841        ttcatgctgg tggtgtcctt ggtgtccctg gccttgaata tcattgaact cttctatgtt
  901        ttcttcaagg gcgttaagga tcgggttaag ggaaagagcg acccttacca tgcgaccagt
  961        ggtgcgctga gccctgccaa agactgtggg tctcaaaat atgcttattt caatggctgc
 1021        tcctcaccaa ccgctcccct ctcgcctatg tctcctcctg ggtacaagct ggttactggc
 1081        gacagaaaca attcttcttg ccgcaattac aacaagcaag caagtgagca aaactgggct
 1141        aattacagtg cagaacaaaa tcgaatgggg caggcgggaa gcaccatctc taactcccat
 1201        gcacagcctt tgatttccc cgatgataac cagaattcta aaaaactagc tgctggacat
 1261        gaattacagc cactagccat tgtggaccag cgaccttcaa gcagagccag cagtcgtgcc
 1321        agcagcgac ctcggcctga tgacctggag atctagatac aggcttgaaa gcatcaagat
 1381        tccactcaat tgtggagaag aaaaaaggtg ctgtagaaag tgcaccaggt gttaattttg
 1441        atccggtgga ggtggtactc aacagcctta ttcatgagcc ttagaaaaca caaagacatt
 1501        agaataccta ggttcactgg gggtgtatgg ggtagatggg tggagaggga ggggataaga
 1561        gaggtgcatg ttggtattta aagtagtgga ttcaaagaac ttagattata aataagagtt
 1621        ccattaggtg atacatagat aagggctttt tctccccgca aacaccccta agaatggttc
 1681        tgtgtatgtg aatgagcggg tggtaattgt ggctaaatat ttttgtttta ccaagaaact
 1741        gaaataattc tggccaggaa taaatacttc ctgaacatct taggtctttt caacaagaaa
 1801        aagacagagg attgtcctta agtccctgct aaaacattcc attgttaaaa tttgcactt
 1861        gaaggtaagc tttctaggcc tgaccctcca ggtgtcaatg gacttgtgct actatatttt
 1921        tttattcttg gtatcagttt aaaattcaga caaggcccac agaataagat tttccatgca
 1981        tttgcaaata cgtatattct ttttccatcc acttgcacaa tatcattacc atcacttttt
```

-continued

```
2041    catcattcct cagctactac tcacattcat ttaatggttt ctgtaaacat ttttaagaca
2101    gttgggatgt cacttaacat tttttttttt tgagctaaag tcagggaatc aagccatgct
2161    taatatttaa caatcactta tatgtgtgtc gaagagtttg ttttgtttgt catgtattgg
2221    tacaagcaga tacagtataa actcacaaac acagatttga aaataatgca catatggtgt
2281    tcaaatttga acctttctca tggatttttg tggtgtgggc caatatggtg tttacattat
2341    ataattcctg ctgtggcaag taaagcacac tttttttttc tcctaaaatg ttttttccctg
2401    tgtatcctat tatggatact ggttttgtta attatgattc tttattttct ctccttttt
2461    taggatatag cagtaatgct attactgaaa tgaatttcct ttttctgaaa tgtaatcatt
2521    gatgcttgaa tgatagaatt ttagtactgt aaacaggctt tagtcattaa tgtgagagac
2581    ttagaaaaaa tgcttagagt ggactattaa atgtgcctaa atgaattttg cagtaactgg
2641    tattcttggg ttttcctact taatacacag taattcagaa cttgtattct attatgagtt
2701    tagcagtctt ttggagtgac cagcaacttt gatgtttgca ctaagatttt atttggaatg
2761    caagagaggt tgaaagagga ttcagtagta cacatacaac taatttattt gaactatatg
2821    ttgaagacat ctaccagttt ctccaaatgc ctttttttaaa actcatcaca gaagattggt
2881    gaaaatgctg agtatgacac ttttcttctt gcatgcatgt cagctacata aacagttttg
2941    tacaatgaaa attactaatt tgtttgacat tccatgttaa actacggtca tgttcagctt
3001    cattgcatgt aatgtagacc tagtccatca gatcatgtgt tctggagagt gttctttatt
3061    caataaagtt ttaatttagt ataaacat
```

Human Cx 46, α3
LOCUS       NM_021954 1308 bp mRNA linear PRI 27 Oct. 2004
DEFINITION  *Homo sapiens* gap junction protein, alpha 3, 46 kDa (connexin 46) (GJA3), mRNA.

(SEQ ID NO: 13)

```
   1    atgggcgact ggagctttct gggaagactc ttagaaaatg cacaggagca ctccacggtc
  61    atcggcaagg tttggctgac cgtgctgttc atcttccgca tcttggtgct gggggccgcg
 121    gcggaggacg tgtggggcga tgagcagtca gacttcacct gcaacaccca gcagccgggc
 181    tgcgagaacg tctgctacga cagggccttc cccatctccc acatccgctt ctgggcgctg
 241    cagatcatct tcgtgtccac gcccacccctc atctacctgg ccacgtgct gcacatcgtg
 301    cgcatggaag agaagaagaa agagagggag gaggaggagc agctgaagag agagagcccc
 361    agccccaagg agccaccgca ggacaatccc tcgtcgcggg acgaccgcg cagggtgcgc
 421    atggccgggg cgctgctgcg gacctacgtc ttcaacatca tcttcaagac gctgttcgag
 481    gtgggcttca tcgccggcca gtacttctg tacggcttcg agctgaagcc gctctaccgc
 541    tgcgaccgct ggccctgccc caacacggtg gactgcttca tctccaggcc cacggagaag
 601    accatcttca tcatcttcat gctggcggtg gcctgcgcgt ccctgctgct caacatgctg
 661    gagatctacc acctgggctg gaagaagctc aagcagggcg tgaccagccg cctcggcccg
 721    gacgcctccg aggccccgct ggggacagcc gatccccgc ccctgccccc cagctcccgg
 781    ccgcccgccg ttgccatcgg gttcccaccc tactatgcgc acaccgctgc gccctggga
 841    caggcccgcg ccgtgggcta ccccgggcc ccgccaccag ccgcggactt caaactgcta
 901    gccctgaccg aggcgcgcgg aaagggccag tccgccaagc tctacaacgc ccaccaccac
 961    ctgctgatga ctgagcagaa ctgggccaac caggcggccg agcggcagcc ccggcgctc
1021    aaggcttacc cggcagcgtc cacgcctgca gccccagcc cgtcggcag cagctcccg
1081    ccactcgcgc acgaggctga ggcgggcgcg gcgccctgc tgctggatgg gagcggcagc
1141    agtctggagg ggagcgccct ggcagggacc cccgaggagg aggagcaggc cgtgaccacc
```

-continued

```
1201        gcggcccaga tgcaccagcc gcccttgccc ctcggagacc caggtcgggc cagcaaggcc 1261        agcagggcca gcagcgggcg ggccagaccg gaggacttgg ccatctag
```

Human Cx 37, α4
LOCUS       NM_002060 1601 bp mRNA linear PRI 26 Oct. 2004
DEFINITION  *Homo sapiens* gap junction protein, alpha 4, 37 kDa (connexin 37)
            (GJA4), mRNA.
                                                              (SEQ ID NO: 14)

```
   1        ctccggccat cgtccccacc tccacctggg ccgcccgcga ggcagcggac ggaggccggg 61        agccatgggt gactgggget tcctggagaa gttgctggac caggtccgag agcactcgac 121        cgtggtgggt aagatctggc tgacggtgct cttcatcttc cgcatcctca tcctgggcct 181        ggccggcgag tcagtgtggg gtgacgagca gtcagatttc gagtgtaaca cggcccagcc 241        aggctgcacc aacgtctgct atgaccaggc cttccccatc tcccacatcc gctactgggt 301        gctgcagttc ctcttcgtca gcacacccac cctggtctac ctgggccatg tcatttacct 361        gtctcggcga gaagagcggc tggcgcagaa ggagggggag ctgcgggcac tgccggccaa 421        ggacccacag gtggagcggg cgctggccgg catagagctt cagatggcca agatctcggt 481        ggcagaagat ggtcgcctgc gcattccgcg agcactgatg ggcacctatg tcgccagtgt 541        gctctgcaag agtgtgctag aggcaggctt cctctatggc cagtggcgcc tgtacggctg 601        gaccatggag cccgtgtttg tgtgccagcg agcaccctgc cctacctcg tggactgctt 661        tgtctctcgc cccacggaga agaccatctt catcatcttc atgttggtgg ttggactcat 721        ctccctggtg cttaacctgc tggagttggt gcacctgctg tgtcgctgcc tcagccgggg 781        gatgagggca cggcaaggcc aagacgcacc cccgacccag ggcacctcct cagaccctta 841        cacggaccag ggtcttcttc tacctccccg tggccagggg ccctcatccc caccatgccc 901        cacctacaat gggctctcat ccagtgagca gaactgggcc aacctgacca cagaggagag 961        gctggcgtct tccaggcccc ctctcttcct ggacccaccc cctcagaatg ccaaaaaacc 1021        cccaagtcgt cccagcagct ctgcttctaa gaagcagtat gtatagaggc ctgtggctta 1081        tgtcacccaa cagaggggtc ctgagaagtc tggctgcctg ggatgccccc tgcccctcc 1141        tggaaggctc tgcagagatg actgggctgg ggaagcagat gcttgctggc catggagcct 1201        cattgcaagt tgttcttgaa cacctgaggc cttcctgtgg cccaccaggc actacggctt 1261        cctctccaga tgtgctttgc ctgagcacag acagtcagca tggaatgctc ttggccaagg 1321        gtactggggc cctctggcct tttgcagctg atccagagga acccagagcc aacttacccc 1381        aacctcaccc tatggaacag tcacctgtgc gcaggttgtc ctcaaaccct ctcctcacag 1441        gaaaaggcgg attgaggctg ctgggtcagc cttgatcgca cagacagagc ttgtgccgga 1501        tttggccctg tcaagggac tggtgccttg ttttcatcac tccttcctag ttctactgtt 1561        caagcttctg aaataaacag gacttgatca caaaaaaaaa a
```

Human Cx 40, α5
LOCUS       NM_005266 2574 bp mRNA linear PRI 27 Oct. 2004
DEFINITION  *Homo sapiens* gap junction protein, alpha 5, 40 kDa (connexin 40)
            (GJA5), transcript variant A, mRNA.
                                                              (SEQ ID NO: 15)

```
   1        gcaaaaagcg tgggcagttg gagaagaagc agccagagtg tgaagaagcc cacggaagga 61        aagtccaggg aggaggaaaa gaagcagaag ttttggcatc tgttccctgg ctgtgccaag 121        atgggcgatt ggagcttcct gggaaatttc ctggaggaag tacacagca ctcgaccgtg 181        gtaggcaagg tctggctcac tgtcctcttc atattccgta tgctcgtgct gggcacagct 241        gctgagtctt cctgggggga tgagcaggct gatttccggt gtgatacgat tcagcctggc 301        tgccagaatg tctgctacga ccaggctttc cccatctccc acattcgcta ctgggtgctg 361        cagatcatct tcgtctccac gcctctctg gtgtacatgg ccacgccat gcacactgtg
```

-continued

```
 421    cgcatgcagg agaagcgcaa gctacgggag gccgagaggg ccaaagaggt ccggggctct
 481    ggctcttacg agtacccggt ggcagagaag gcagaactgt cctgctggga ggaagggaat
 541    ggaaggattg ccctccaggg cactctgctc aacacctatg tgtgcagcat cctgatccgc
 601    accaccatgg aggtgggctt cattgtgggc cagtacttca tctacggaat cttcctgacc
 661    accctgcatg tctgccgcag gagtccctgt ccccacccgg tcaactgtta cgtatcccgg
 721    cccacagaga agaatgtctt cattgtcttt atgctggctg tggctgcact gtccctcctc
 781    cttagcctgg ctgaactcta ccacctgggc tggaagaaga tcagacagcg atttgtcaaa
 841    ccgcggcagc acatggctaa gtgccagctt tctggcccct ctgtgggcat agtccagagc
 901    tgcacaccac cccccgactt taatcagtgc ctggagaatg ccctgggggg aaaattcttc
 961    aatcccttca gcaataatat ggcctcccaa caaaacacag acaacctggt caccgagcaa
1021    gtacgaggtc aggagcagac tcctggggaa ggtttcatcc aggttcgtta tggccagaag
1081    cctgaggtgc ccaatggagt ctcaccaggt caccgccttc ccatggctca tcatagtgac
1141    aagcgacgtc ttagtaaggc cagcagcaag gcaaggtcag atgacctatc agtgtgaccc
1201    tcctttatgg gaggatcagg accaggtggg aacaaaggag gctcagagaa gaaagacgtg
1261    tcccttctga actgatgctt tctcactgtc atcactgctt ggctcctttg agccccgggt
1321    ctcaatgacg ttgctcatta attctagaaa ctataaccag ggctctggga tagtaagaga
1381    ggtgacaacc cacccagact gcagttccct ccccacctc tacccagtat acgaagcctt
1441    tcagattact catgaaacag ggtagaggga agaagggaa gcatggcaaa agctggcctg
1501    gaagggatag ccagaggat agaatgactc tctctctaca taccagcagc ataccaaatg
1561    cgttctctaa gttcctacct ccttgacctg atcaccctcc ctcctccaag gaagagctca
1621    aagttcccag ccaatagaca gcatgaatca aggaacttgc attatatgtg ctcttgaatc
1681    tgttgtctcc atggaccatt cctcggagta gtggtgagat ggcttgggt tgcccttggc
1741    ttctcctccc tctactcagc cttaaaaagg gcttcttgga actttaccag cagcctcagc
1801    tttacaaatg ccttggtatg tacctctggc aaatgcccca ccttggtgat gttgcaacct
1861    ttccttctgc tagggtgtac acctagcctg tgcaggtgtc agccctgcta gggagtcact
1921    gtacacacaa actctactgg aattcctgcc aacatctgtc accctgcagc tcctttacag
1981    ttcaatccaa tgatagaaac catcccttcc ctttctccct ggctgttca cccagccatt
2041    ccctgaaggc cttaccaaca ggaatatcca agaagctgtt gtcccctctc gaaccctgac
2101    cagatcatca gccactgagg ccagtggaat ttccccaggc cttgttaaaa caaagaaagc
2161    attgtacctc tcagattccc cttgtggaaa aaaaaattct gctgtgaaga tgaaaataaa
2221    aatggagaga aaacactgga aaactatttt cccctcctat ttacttcctt gctgactgc
2281    caacttagtg ccaagaggag gtgtgatgac agctatggag gccccagat ctctctctcc
2341    tggaggcttt agcaggggca aggaaatagt agggaatct ccagctctct tggcagggcc
2401    tttattaaa gagcgcagag attcctatgt ctccctagtg ccctaatga gactgccaag
2461    tgggggctgt agaaaagcct tgccttcccc agggattggc ctggtctctg tattcactgg
2521    atccataatg ggttgctgtt gttttggatg aaggtaaacg atgcttggaa ttgg
```

Human Cx 45, α7
LOCUS       NM_005497 1191 bp mRNA linear PRI 23 Dec. 2003
DEFINITION  *Homo sapiens* gap junction protein, alpha 7, 45 kDa (connexin 45)
            (GJA7), mRNA.

(SEQ ID NO: 16)

```
   1    atgagttgga gctttctgac tcgcctgcta gaggagattc acaaccattc cacatttgtg
  61    gggaagatct ggctcactgt tctgattgtc ttccggatcg tccttacagc tgtaggagga
```

-continued

```
  121       gaatccatct attacgatga gcaaagcaaa tttgtgtgca acacagaaca gccgggctgt
  181       gagaatgtct gttatgatgc gtttgcacct ctctcccatg tacgcttctg ggtgttccag
  241       atcatcctgg tggcaactcc ctctgtgatg tacctgggct atgctatcca caagattgcc
  301       aaaatggagc acggtgaagc agacaagaag gcagctcgga gcaagcccta tgcaatgcgc
  361       tggaaacaac accgggctct ggaagaaacg gaggaggaca cgaagagga tcctatgatg
  421       tatccagaga tggagttaga aagtgataag gaaataaag agcagagcca acccaaacct
  481       aagcatgatg gccgacgacg gattcgggaa gatgggctca tgaaaatcta tgtgctgcag
  541       ttgctggcaa ggaccgtgtt tgaggtgggt tttctgatag ggcagtattt tctgtatggc
  601       ttccaagtcc acccgtttta tgtgtgcagc agacttcctt gtcctcataa gatagactgc
  661       tttatttcta gacccactga aaagaccatc ttccttctga taatgtatgt gttacaggc
  721       ctttgcctct tgcttaacat ttgggagatg cttcatttag ggtttgggac cattcgagac
  781       tcactaaaca gtaaaaggag ggaacttgag gatccgggtg cttataatta tcctttcact
  841       tggaatacac catctgctcc ccctggctat aacattgctg tcaaaccaga tcaaatccag
  901       tacaccgaac tgtccaatgc taagatcgcc tacaagcaaa acaaggccaa cacagcccag
  961       gaacagcagt atggcagcca tgaggagaac ctcccagctg acctggaggc tctgcagcgg
 1021       gagatcagga tggctcagga acgcttggat ctggcagttc aggcctacag tcaccaaaac
 1081       aaccctcatg gtccccggga agaaggcc aaagtgggt ccaaagctgg gtccaacaaa
 1141       agcactgcca gtagcaaatc aggggatggg aagaactctg tctggattta a
```

Human Cx 50, α8
LOCUS       NM_005267 1362 bp mRNA linear PRI 26 Oct. 2004
DEFINITION  *Homo sapiens* gap junction protein, alpha 8, 50 kDa (connexin 50)
            (GJA8), mRNA.
                                                              (SEQ ID NO: 17)

```
    1       agcgccaaga gagaaagagc acatatttct ccgtgggaca ctccttgtat tggtgggtga
   61       gaaatgggcg actggagttt cctggggaac atcttggagg aggtgaatga gcactccacc
  121       gtcatcggca gagtctggct caccgtgctt ttcatcttcc ggatcctcat ccttggcacg
  181       gccgcagagt tcgtgtgggg ggatgagcaa tccgacttcg tgtgcaacac ccagcagcct
  241       ggctgcgaga acgtctgcta cgacgaggcc tttcccatct cccacattcg cctctgggtg
  301       ctgcagatca tcttcgtctc caccccgtcc ctgatgtacg tggggcacgc ggtgcactac
  361       gtccgcatgg aggagaagcg caaaagccgc gacgaggagc tgggccagca ggcggggact
  421       aacggcggcc cggaccaggg cagcgtcaag aagagcagcg gcagcaaagg cactaagaag
  481       ttccggctgg aggggaccct gctgaggacc tacatctgcc acatcatctt caagaccctc
  541       tttgaagtgg gcttcatcgt gggccactac ttcctgtacg ggttccggat cctgcctctg
  601       taccgctgca gccggtggcc ctgcccaat gtggtggact gcttcgtgtc cggcccacg
  661       gagaaaacca tcttcatcct gttcatgttg tctgtggcct ctgtgtccct attcctcaac
  721       gtgatggagt tgagccacct gggcctgaag gggatccggt ctgccttgaa gaggcctgta
  781       gagcagcccc tggggagat tcctgagaaa tccctccact ccattgctgt ctcctccatc
  841       cagaaagcca agggctatca gcttctagaa gaagagaaaa tcgtttccca ctatttcccc
  901       ttgaccgagg ttgggatggt ggagaccagc ccactgcctg ccaagccttt caatcagttc
  961       gaggagaaga tcagcacagg accctggg gacttgtccc ggggctacca agagacactg
 1021       ccttcctacg ctcaggtggg ggcacaagaa gtggagggcg aggggccgcc tgcagaggag
 1081       ggagccgaac ccgaggtggg agagaagaag gaggaagcag agaggctgac cacggaggag
 1141       caggagaagg tggccgtgcc agaggggag aaagtagaga ccccccggagt ggataaggag
```

```
1201        ggtgaaaaag aagagccgca gtcggagaag gtgtcaaagc aagggctgcc agctgagaag 1261        acaccttcac tctgtccaga gctgacaaca gatgatgcca gaccctgag caggctaagc 1321        aaagccagca gccgagccag gtcagacgat ctaaccgtat ga
```

Human Cx 36, α9, γ1
LOCUS       NM_020660 966 bp mRNA linear PRI 3 Sep. 2004
DEFINITION  *Homo sapiens* connexin-36 (CX36), mRNA.
(SEQ ID NO: 18)

```
  1         atgggggaat ggaccatctt ggagaggctg ctagaagccg cggtgcagca gcactccact 61         atgatcggaa ggatcctgtt gactgtggtg gtgatcttcc ggatcctcat tgtggccatt 121         gtggggagga cggtgtacga tgatgagcag accatgtttg tgtgcaacac cctgcagccc 181         ggctgtaacc aggcctgcta tgaccgggcc ttccccatct cccacatacg ttactgggtc 241         ttccagatca taatggtgtg taccccccagt ctttgcttca tcacctactc tgtgcaccag 301         tccgccaagc agcgagaacg ccgctactct acagtcttcc tagccctgga cagagacccc 361         cctgagtcca taggaggtcc tggaggaact gggggtgggg gcagtggtgg gggcaaacga 421         gaagataaga agttgcaaaa tgctattgtg aatggggtgc tgcagaacac agagaacacc 481         agtaaggaga cagagccaga ttgtttagag gttaaggagc tgactccaca cccatcaggt 541         ctacgcactg catcaaaatc caagctcaga aggcaggaag gcatctcccg cttctacatt 601         atccaagtgg tgttccgaaa tgccctggaa attgggttcc tggttggcca atattttctc 661         tatggcttta gtgtcccagg ttgtatgag tgtaaccgct accctgcat caaggagtg 721         gaatgttatg tgtcccggcc aactgagaag actgtctttc tagtgttcat gtttgctgta 781         agtggcatct gtgttgtgct caacctggct gaactcaacc acctgggatg gcgcaagatc 841         aagctggctg tgcgaggggc tcaggccaag agaaagtcaa tctatgagat tcgtaacaag 901         gacctgccaa gggtcagtgt tcccaatttt ggcaggactc agtccagtga ctctgcctat 961         gtgtga
```

Human Cx 59/58, α10
LOCUS       NM_030772 1901 bp mRNA linear PRI 27 Oct. 2004
DEFINITION  *Homo sapiens* gap junction protein, alpha 10, 59 kDa (GJA10), mRNA.
(SEQ ID NO: 19)

```
  1         cagggagttg tggttgcaac actgtactcc agcctgggca acagagggag actctgtctc 61         aacaaacaaa caaacaaaga aaaaacccca cagctatcta gggaaaaagt aaagcaacca 121         gcatatagaa gtgacatatt gttatatttt caccataggt ttgctttaag aaatagtgct 181         cccttcagaa tggaagaatt tatctgcctc ttatttgatg tggatcagag ctaagatggc 241         tgactaaata aacatggggg actggaatct ccttggagat actctggagg aagttcacat 301         ccactccacc atgattggaa agatctggct caccatcctg ttcatatttc gaatgcttgt 361         tctgggtgta gcagctgaag atgtctggaa tgatgagcag tctggcttca tctgcaatac 421         agaacaacca ggctgcagaa atgtatgcta cgaccaggcc tttcctatct ccctcattag 481         atactgggtt ctgcaggtga tatttgtgtc ttcaccatcc ctggtctaca tgggccatgc 541         attgtaccga ctgagagttc ttgaggaaga gaggcaaagg atgaaagctc agttaagagt 601         agaactggag gaggtagagt ttgaaatgcc tagggatcgg aggagattgg agcaagagct 661         ttgtcagctg gagaaaagga aactaaataa agctccactc agaggaacct gctttgcac 721         ttatgtgata cacattttca ctcgctctgt ggttgaagtt ggattcatga ttggacagta 781         cctttttatat ggatttcact tagagccgct attaagtgc catggccacc cgtgtccaaa 841         tataatcgac tgttttgtct caagaccaac agaaaagaca atattcctat tatttatgca 901         atctatagcc actatttcac ttttcttaaa cattcttgaa attttccacc taggttttaa
```

```
 961        aaagattaaa agagggcttt ggggaaaata caagttgaag aaggaacata atgaattcca
1021        tgcaaacaag gcaaaacaaa atgtagccaa ataccagagc acatctgcaa attcactgaa
1081        gcgactccct tctgcccctg attataatct gttagtggaa aagcaaacac acactgcagt
1141        gtaccctagt ttaaattcat cttctgtatt ccagccaaat cctgacaatc atagtgtaaa
1201        tgatgagaaa tgcattttgg atgaacagga aactgtactt tctaatgaga tttccacact
1261        tagtactagt tgtagtcatt ttcaacacat cagttcaaac aataacaaag acactcataa
1321        aatatttgga aaagaactta atggtaacca gttaatggaa aaagagaaa ctgaaggcaa
1381        agacagcaaa aggaactact actctagagg tcaccgttct attccaggtt ttgctataga
1441        tggagagaac aacatgaggc agtcacccca aacagttttc tccttgccag ctaactgcga
1501        ttggaaaccg cggtggctta gctacatg gggttcctct acagaacatg aaaaccgggg
1561        gtcacctcct aaaggtaacc tcaagggcca gttcagaaag gcacagtca gaacccttcc
1621        tccttcacaa ggagattctc aatcacttga cattccaaac actgctgatt ctttgggagg
1681        gctgtccttt gagccagggt tggtcagaac ctgtaataat cctgtttgtc ctccaaatca
1741        cgtagtgtcc ctaacgaaca atctcattgg taggcgggtt cccacagatc ttcagatcta
1801        aacagcggtt ggcttttaga cattatatat attatcagag aagtagccta gtggtcgtgg
1861        ggcacagaaa aaatagatag gggcagctct aaagaccagc t
```

Human Cx 46.6/47, α12
LOCUS       AY285161 1311 bp mRNA linear PRI 19 May 2003
DEFINITION  *Homo sapiens* connexin47 mRNA, complete cds.
(SEQ ID NO: 20)

```
   1        atgagctgga gcttcctgac gcggctgctg gaggagatcc acaaccactc caccttcgtg
  61        ggcaaggtgt ggctcacggt gctggtggtc ttccgcatcg tgctgacggc tgtgggcggc
 121        gaggccatct actcggacga gcaggccaag ttcacttgca acacgcggca gccaggctgc
 181        gacaacgtct gctatgacgc cttcgcgccc ctgtcgcacg tgcgcttctg ggtcttccag
 241        attgtggtca tctccacgcc ctcggtcatg tacctgggct acgccgtgca ccgcctggcc
 301        cgtgcgtctg agcaggagcg gcgccgcgcc ctccgccgcc gcccggggcc acgccgcgcg
 361        ccccgagcgc acctgccgcc cccgcacgcc ggctggcctg agcccgccga cctgggcgag
 421        gaggagccca tgctgggcct gggcgaggag gaggaggagg aggagacggg ggcagccgag
 481        ggcgccggcg aggaagcgga ggaggcaggc gcggaggagg cgtgcactaa ggcggtcggc
 541        gctgacggca aggcggcagg gaccccgggc ccgaccgggc aacacgatgg gcggaggcgc
 601        atccagcggg agggcctgat gcgcgtgtac gtgcccagc tggtggccag ggcagctttc
 661        gaggtggcct tcctggtggg ccagtacctg ctgtacggct tcgaggtgcg accgttcttt
 721        ccctgcagcc gccagccctg cccgcacgtg gtggactgct tcgtgtcgcg ccctactgaa
 781        aagacggtct tcctgctggt tatgtacgtg gtcagctgcc tgtgcctgct gctcaacctc
 841        tgtgagatgg cccacctggg cttgggcagc gcgcaggacg cggtgcgcgg ccgccgcggc
 901        ccccggcct ccgccccgc ccccgcgccg cggcccccgc cctgcgcctt cctgcggcg
 961        gccgctggct tggcctgccc gcccgactac agcctggtgg tgcgggcggc cgagcgcgct
1021        cgggcgcatg accagaacct ggcaaacctg gccctgcagg cgctgcgcga cggggcagcg
1081        gctggggacc gcgaccggga cagttcgccg tgcgtcggcc tcctgcggc ctccggggg
1141        ccccccagag caggcgcccc cgcgtcccgg acgggcagtg ctacctctgc gggcactgtc
1201        ggggagcagg gccggccgg cacccacgag cggccaggag ccaagcccag ggctggctcc
1261        gagaagggca gtgccagcag cagggacggg aagaccaccg tgtggatctg a
```

Human Cx 32, β1
LOCUS       BC039198 1588 bp mRNA linear PRI 7 Oct. 2003
DEFINITION  *Homo sapiens* gap junction protein, beta 1, 32 kDa (connexin 32,
            Charcot-Marie-Tooth neuropathy, X-linked), mRNA (cDNA clone
            MGC: 22506 IMAGE: 4710239), complete cds.
                                                            (SEQ ID NO: 21)
       1    agacattctc tgggaaaggg cagcagcagc caggtgtggc agtgacaggg aggtgtgaat
      61    gaggcaggat gaactggaca ggtttgtaca ccttgctcag tggcgtgaac cggcattcta
     121    ctgccattgg ccgagtatgg ctctcggtca tcttcatctt cagaatcatg gtgctggtgg
     181    tggctgcaga gagtgtgtgg ggtgatgaga atcttccttt catctgcaac acactccagc
     241    ctggctgcaa cagcgtttgc tatgaccaat tcttccccat ctcccatgtg cggctgtggt
     301    ccctgcagct catcctagtt tccacccag ctctcctcgt ggccatgcac gtggctcacc
     361    agcaacacat agagaagaaa atgctacggc ttgagggcca tggggacccc ctacacctgg
     421    aggaggtgaa gaggcacaag gtccacatct cagggacact gtggtggacc tatgtcatca
     481    gcgtggtgtt ccggctgttg tttgaggccg tcttcatgta tgtcttttat ctgctctacc
     541    ctggctatgc catggtgcgg ctggtcaagt gcgacgtcta ccctgcccc aacacagtgg
     601    actgcttcgt gtcccgcccc accgagaaaa ccgtcttcac cgtcttcatg ctagctgcct
     661    ctggcatctg catcatcctc aatgtggccg aggtggtgta cctcatcatc cgggcctgtg
     721    cccgccgagc cagcgccgc tccaatccac cttcccgcaa gggctcgggc ttcggccacc
     781    gcctctcacc tgaatacaag cagaatgaga tcaacaagct gctgagtgag caggatggct
     841    ccctgaaaga catactgcgc cgcagccctg caccggggc tgggctggct gaaaagagcg
     901    accgctgctc ggcctgctga tgccacatac caggcaacct cccatcccac ccccgaccct
     961    gccctgggcg agccctcct ctcccctgc cggtgcacag gcctctgcct gctggggatt
    1021    actcgatcaa aaccttcctt ccctggctac ttcccttcct cccggggcct tccttttgag
    1081    gagctggagg ggtggggagc tagaggccac ctatgccagt gctcaaggtt actgggagtg
    1141    tgggctgccc ttgttgcctg caccttccc tcttccctct ccctctctct gggaccactg
    1201    ggtacaagag atgggatgct ccgacagcgt ctccaattat gaaactaatc ttaaccctgt
    1261    gctgtcagat accctgtttc tggagtcaca tcagtgagga gggatgtggg taagaggagc
    1321    agagggcagg ggtgctgtgg acatgtgggt ggagaaggga gggtggccag cactagtaaa
    1381    ggaggaatag tgcttgctgg ccacaaggaa aaggaggagg tgtctggggt gagggagtta
    1441    gggagagaga agcaggcaga taagttggag caggggttgg tcaaggccac ctctgcctct
    1501    agtccccaag gcctctctct gcctgaaatg ttacacatta aacaggattt tacagcaaaa
    1561    aaaaaaaaaa aaaaaaaaaa aaaaaaaa Human Cx 26, β2
LOCUS       NM_004004 2263 bp mRNA linear PRI 28 Oct. 2004
DEFINITION  *Homo sapiens* gap junction protein, beta 2, 26 kDa (connexin 26)
            (GJB2), mRNA.
                                                            (SEQ ID NO: 22)
       1    cggagcccct cggcgcgcc cggcccagga cccgcctagg agcgcaggag cccagcgca
      61    gagaccccaa cgccgagacc cccgccccgg ccccgccgcg cttcctcccg acgcagagca
     121    aaccgcccag agtagaagat ggattggggc acgctgcaga cgatcctggg gggtgtgaac
     181    aaacactcca ccagcattgg aaagatctgg ctcaccgtcc tcttcatttt tcgcattatg
     241    atcctcgttg tggctgcaaa ggaggtgtgg ggagatgagc aggccgactt tgtctgcaac
     301    accctgcagc caggctgcaa gaacgtgtgc tacgatcact acttccccat ctcccacatc
     361    cggctatggg ccctgcagct gatcttcgtg tccacgccag cgctcctagt ggccatgcac
     421    gtggcctacc ggagacatga aaagaagagg aagttcatca agggggagat aaagagtgaa

```
 481        tttaaggaca tcgaggagat caaaacccag aaggtccgca tcgaaggctc cctgtggtgg 541        acctcacaca gcagcatctt cttccgggtc atcttcgaag ccgccttcat gtacgtcttc 601        tatgtcatgt acgacggctt ctccatgcag cggctggtga agtgcaacgc ctggccttgt 661        cccaacactg tggactgctt tgtgtcccgg cccacggaga agactgtctt cacagtgttc 721        atgattgcag tgtctggaat ttgcatcctg ctgaatgtca ctgaattgtg ttatttgcta 781        attagatatt gttctgggaa gtcaaaaaag ccagtttaac gcattgccca gttgttagat 841        taagaaatag acagcatgag agggatgagg caacccgtgc tcagctgtca aggctcagtc 901        gccagcattt cccaacacaa agattctgac cttaaatgca accatttgaa accoctgtag 961        gcctcaggtg aaactccaga tgccacaatg gagctctgct cccctaaagc ctcaaaacaa 1021        aggcctaatt ctatgcctgt cttaattttc tttcacttaa gttagttcca ctgagacccc 1081        aggctgttag gggttattgg tgtaaggtac tttcatattt taaacagagg atatcggcat 1141        ttgtttcttt ctctgaggac aagagaaaaa agccaggttc cacagaggac acagagaagg 1201        tttgggtgtc ctcctggggt tcttttttgcc aactttcccc acgttaaagg tgaacattgg 1261        ttctttcatt tgctttggaa gttttaatct ctaacagtgg acaaagttac cagtgcctta 1321        aactctgtta cacttttttgg aagtgaaaac tttgtagtat gataggttat tttgatgtaa 1381        agatgttctg gataccatta tatgttcccc ctgtttcaga ggctcagatt gtaatatgta 1441        aatggtatgt cattcgctac tatgatttaa tttgaaatat ggtcttttgg ttatgaatac 1501        tttgcagcac agctgagagg ctgtctgttg tattcattgt ggtcatagca cctaacaaca 1561        ttgtagcctc aatcgagtga gacagactga aagttcctag tgatggctta tgatagcaaa 1621        tggcctcatg tcaaatattt agatgtaatt ttgtgtaaga aatacagact ggatgtacca 1681        ccaactacta cctgtaatga caggcctgtc caacacatct ccctttttcca tgactgtggt 1741        agccagcatc ggaaagaacg ctgatttaaa gaggtcgctt gggaattttta ttgacacagt 1801        accatttaat ggggaggaca aaatgggggca ggggaggggag aagtttctgt cgttaaaaac 1861        agatttggaa agactggact ctaaattctg ttgattaaag atgagctttg tctacttcaa 1921        aagtttgttt gcttacccct tcagcctcca attttttaag tgaaaatata actaataaca 1981        tgtgaaaaga atagaagcta aggtttagat aaatattgag cagatctata ggaagattga 2041        acctgaatat tgccattatg cttgacatgg tttccaaaaa atggtactcc acatacttca 2101        gtgagggtaa gtatttcct gttgtcaaga atagcattgt aaaagcattt tgtaataata 2161        aagaatagct ttaatgatat gcttgtaact aaaataattt tgtaatgtat caaatacatt 2221        taaaacatta aaatataatc tctataataa aaaaaaaaa aaa
```

Human Cx 31, β3
LOCUS       NM_024009 2220 bp mRNA linear PRI 28 Oct. 2004
DEFINITION  Homo sapiens gap junction protein, beta 3, 31 kDa (connexin 31)
            (GJB3), transcript variant 1, mRNA.

(SEQ ID NO: 23)

```
   1        gaacttcttt cctggcacag gactcactgt gccccttccc gctgtgggta caaggtctgc 61        cccccacccc agctctccaa agccaccgg cctccctgga ggccgaggtc gacggcccgt 121        cgcaccggga ggggggggctc ccaggggtgc cccacgcacg gtcaaggtcc cgcgccaagc 181        ggggaccggg ctgggccgga agcgggcacg gtactcgcgg caaactagcg tgggcgagtc 241        ctgattgcag tcggacctgc cgccgcggca cttaacagtt tgcagagtgc ttcccgcccc 301        tgatctcatt ggagccttcg gacagcccag cccatggcca ccgatgcccc catttcacgc 361        ctgaggaagc ggaggctcag acggccacc agccctccg gaggctggcc cgggagcgcc 421        tggcagcgtc gggtctagga gccggctccc tcctgctccc tcctccgcgc cgcccggggt
```

```
 481        gtgcccgccg tctgtgtgca ccactgctga gcccagctcc ggcgccctcg cctctgctgt 541        gggcccoggg gacgcggggt caggccaccg cgttggccag gccgctgcag gtaggcacgg 601        cccccaccag gcgccatgga ctggaagaca ctccaggccc tactgagcgg tgtgaacaag 661        tactccacag cgttcgggcg catctggctg tccgtggtgt tcgtcttccg ggtgctggta 721        tacgtggtgg ctgcagagcg cgtgtggggg gatgagcaga aggactttga ctgcaacacc 781        aagcagcccg gctgcaccaa cgtctgctac gacaactact cccccatctc caacatccgc 841        ctctgggccc tgcagctcat cttcgtcaca tgcccctcgc tgctggtcat cctgcacgtg 901        gcctaccgtg aggagcggga gcgccggcac cgccagaaac acggggacca gtgcgccaag 961        ctgtacgaca acgcaggcaa gaagcacgga ggcctgtggt ggacctacct gttcagcctc 1021        atcttcaagc tcatcattga gttcctcttc ctctacctgc tgcacactct ctggcatggc 1081        ttcaatatgc cgcgcctggt gcagtgtgcc aacgtggccc cctgcccaa catcgtggac 1141        tgctacattg cccgacctac cgagaagaaa atcttcacct acttcatggt gggcgcctcc 1201        gccgtctgca tcgtactcac catctgtgag ctctgctacc tcatctgcca cagggtcctg 1261        cgaggcctgc acaaggacaa gcctcgaggg ggttgcagcc cctcgtcctc cgccagccga 1321        gcttccacct gccgctgcca ccacaagctg gtggaggctg gggaggtgga tccagaccca 1381        ggcaataaca agctgcaggc ttcagcaccc aacctgaccc ccatctgacc acagggcagg 1441        ggtggggcaa catgcgggct gccaatggga catgcagggc ggtgtggcag gtggagaggt 1501        cctacagggg ctgagtgacc ccactctgag ttcactaagt tatgcaactt tcgttttggc 1561        agatattttt tgacactggg aactgggctg tctagccggg tataggtaac ccacaggccc 1621        agtgccagcc ctcaaaggac atagactttg aaacaagcga attaactatc tacgctgcct 1681        gcaaggggcc acttaggcag ctgctagcag ggcttcaacc aggaagggat caacccagga 1741        agggatgatc aggagaggct tccctgagga cataatgtgt aagagaggtg agaagtgctc 1801        ccaagcagac acaacagcag cacagaggtc tggaggccac acaaaaagtg atgctcgccc 1861        tgggctagcc tcagcagacc taaggcatct ctactccctc cagaggagcc gcccagattc 1921        ctgcagtgga gaggaggtct tccagcagca gcaggtctgg agggctgaga atgaacctga 1981        ctagaggttc tggagatacc cagaggtccc ccaggtcatc acttggctca gtggaagccc 2041        tctttcccca aatcctactc cctcagcctc aggcagtggt gctcccatct tcctccccac 2101        aactgtgctc aggctggtgc cagcctttca gaccctgctc ccagggactt gggtggatgc 2161        gctgatagaa catcctcaag acagtttcct tgaaatcaat aaatactgtg ttttataaaa
```

Human Cx30.3, β4
LOCUS       NM_153212 1243 bp mRNA linear PRI 27 Oct. 2004
DEFINITION  Homo sapiens gap junction protein, beta 4 (connexin 30.3) (GJB4),
            mRNA.

(SEQ ID NO: 24)

```
   1        caaggctccc aaggcctgag tgggcaggta gcacccaggt atagaccttc cacgtgcagc 61        acccaggaca cagccagcat gaactgggca tttctgcagg gcctgctgag tggcgtgaac 121        aagtactcca cagtgctgag ccgcatctgg ctgtctgtgg tgttcatctt tcgtgtgctg 181        gtgtacgtgg tggcagcgga ggaggtgtgg gacgatgagc agaaggactt tgtctgcaac 241        accaagcagc ccggctgccc caacgtctgc tatgacgagt tcttcccccgt gtcccacgtg 301        cgcctctggg ccctacagct catcctggtc acgtgcccct cactgctcgt ggtcatgcac 361        gtggcctacc gcgaggaacg cgagcgcaag caccacctga acacgggcc caatgccccg 421        tccctgtacg acaacctgag caagaagcgg ggcggactgt ggtggacgta cttgctgagc 481        ctcatcttca aggccgccgt ggatgctggc ttcctctata tcttccaccg cctctacaag
```

-continued

```
 541        gattatgaca tgccccgcgt ggtggcctgc tccgtggagc cttgccccca cactgtggac 601        tgttacatct cccggcccac ggagaagaag gtcttcacct acttcatggt gaccacagct 661        gccatctgca tcctgctcaa cctcagtgaa gtcttctacc tggtgggcaa gaggtgcatg 721        gagatcttcg gccccaggca ccggcggcct cggtgccggg aatgcctacc cgatacgtgc 781        ccaccatatg tcctctccca gggagggcac cctgaggatg ggaactctgt cctaatgaag 841        gctgggtcgg ccccagtgga tgcaggtggg tatccataac ctgcgagatc agcagataag 901        atcaacaggt ccccccaca tgaggccacc caggaaaaaa ggcagggca gtggcatcct 961        tgccgtagca gggtggtgag gagggtggct gtgggggctc aggaagctcg cccaggggcc 1021        aatgtgggag gttgggggta gtttggtccc tgggtcctga gcctcagggg agggaggttg 1081        atagctactg gggattttgt atatggcaac agtatatgtc aaacctctta ttaaatatga 1141        ttttcccagt aaaaaaaaaa aaaaaaaaaa aaaaaaaaaa aaaaaaaaaa aaaaaaaaaa 1201        aaaaaaaaaa aaaaaaaaaa aaaaaaaaaa aaaaaaaaaa aaa
```

Human Cx31.1, β5
LOCUS       NM_005268 1299 bp mRNA linear PRI 23 Aug. 2004
DEFINITION  Homo sapiens gap junction protein, beta 5 (connexin 31.1) (GJB5),
            mRNA.
(SEQ ID NO: 25)

```
   1        atgaaattca agctgcttgc tgagtcctat tgccggctgc tgggagccag agagccctg 61        aggagtagtc actcagtagc agctgacgcg tgggtccacc atgaactgga gtatctttga 121        gggactcctg agtggggtca acaagtactc cacagccttt ggcgcatct ggctgtctct 181        ggtcttcatc ttccgcgtgc tggtgtacct ggtgacggcc gagcgtgtgt ggagtgatga 241        ccacaaggac ttcgactgca atactcgcca gccggctgc tccaacgtct gctttgatga 301        gttcttccct gtgtcccatg tgccctctg ggccctgcag cttatcctgg tgacatgccc 361        ctcactgctc gtggtcatgc acgtggccta ccgggaggtt caggagaaga ggcaccgaga 421        agcccatggg gagaacagtg ggcgcctcta cctgaacccc ggcaagaagc ggggtgggct 481        ctggtggaca tatgtctgca gcctagtgtt caaggcgagc gtggacatcg cctttctcta 541        tgtgttccac tcattctacc ccaaatatat cctccctcct gtggtcaagt gccacgcaga 601        tccatgtccc aatatagtgg actgcttcat ctccaagccc tcagagaaga acatttcac 661        cctcttcatg gtggccacag ctgccatctg catcctgctc aacctcgtgg agctcatcta 721        cctggtgagc aagagatgcc acgagtgcct ggcagcaagg aaagctcaag ccatgtgcac 781        aggtcatcac ccccacggta ccacctcttc ctgcaaacaa gacgacctcc tttcgggtga 841        cctcatcttt ctgggctcag acagtcatcc tcctctctta ccagaccgcc ccgagacca 901        tgtgaagaaa accatcttgt gagggctgc ctggactggt ctggcaggtt gggcctggat 961        ggggaggctc tagcatctct cataggtgca acctgagagt gggggagcta agccatgagg 1021        taggggcagg caagagagag gattcagacg ctctgggagc cagttcctag tcctcaactc 1081        cagccacctg ccccagctcg acggcactgg gccagttccc cctctgctct gcagctcggt 1141        ttccttttct agaatggaaa tagtgagggc caatgcccag ggttggaggg aggagggcgt 1201        tcatagaaga acacacatgc gggcaccttc atcgtgtgtg cccactgtc agaacttaat 1261        aaaagtcaac tcatttgctg aaaaaaaaaa aaaaaaaaa
```

Human Cx 30, β6
LOCUS       BC038934 1805 bp mRNA linear PRI 30 Jun. 2004
DEFINITION  Homo sapiens gap junction protein, beta 6 (connexin 30), mRNA (cDNA
            clone MGC: 45195 IMAGE: 5196769), complete cds.
(SEQ ID NO: 26)

```
   1        ctgggaagac gctggtcagt tcacctgccc cactggttgt ttttaaaca aattctgata 61        caggcgacat cctcactgac cgagcaaaga ttgacattcg tatcatcact gtgcaccatt
```

-continued

```
 121        ggcttctagg cactccagtg gggtaggaga aggaggtctg aaaccctcgc agagggatct
 181        tgccctcatt ctttgggtct gaaacactgg cagtcgttgg aaacaggact cagggataaa
 241        ccagcgcaat ggattggggg acgctgcaca ctttcatcgg ggtgtcaac aaacactcca
 301        ccagcatcgg gaaggtgtgg atcacagtca tctttatttt ccgagtcatg atcctcgtgg
 361        tggctgccca ggaagtgtgg ggtgacgagc aagaggactt cgtctgcaac acactgcaac
 421        cgggatgcaa aaatgtgtgc tatgaccact ttttcccggt gtcccacatc cggctgtggg
 481        ccctccagct gatcttcgtc tccaccccag cgctgctggt ggccatgcat gtggcctact
 541        acaggcacga aaccactcgc aagttcaggc gaggagagaa gaggaatgat ttcaaagaca
 601        tagaggacat taaaaagcag aaggttcgga tagaggggtc gctgtggtgg acgtacacca
 661        gcagcatctt tttccgaatc atctttgaag cagcctttat gtatgtgttt tacttccttt
 721        acaatgggta ccacctgccc tgggtgttga aatgtgggat tgaccccgc cccaaccttg
 781        ttgactgctt tatttctagg ccaacagaga agaccgtgtt taccattttt atgatttctg
 841        cgtctgtgat ttgcatgctg cttaacgtgg cagagttgtg ctacctgctg ctgaaagtgt
 901        gttttaggag atcaaagaga gcacagacgc aaaaaaatca ccccaatcat gccctaaagg
 961        agagtaagca gaatgaaatg aatgagctga tttcagatag tggtcaaaat gcaatcacag
1021        gtttcccaag ctaaacattt caaggtaaaa tgtagctgcg tcataaggag acttctgtct
1081        tctccagaag gcaataccaa cctgaaagtt ccttctgtag cctgaagagt ttgtaaatga
1141        ctttcataat aaatagacac ttgagttaac tttttgtagg atacttgctc cattcataca
1201        caacgtaatc aaatatgtgg tccatctctg aaaacaagag actgcttgac aaaggagcat
1261        tgcagtcact ttgacaggtt cctttttaagt ggactctctg acaaagtggg tactttctga
1321        aaatttatat aactgttgtt gataaggaac atttatccag gaattgatac ttttattagg
1381        aaaagatatt tttataggct tggatgtttt tagttctgac tttgaattta tataaagtat
1441        ttttataatg actggtcttc cttacctgga aaaacatgcg atgttagttt tagaattaca
1501        ccacaagtat ctaaatttgg aacttacaaa gggtctatct tgtaaatatt gttttgcatt
1561        gtctgttggc aaatttgtga actgtcatga tacgcttaag gtggaaagtt ttcattgcac
1621        aatatatttt tactgctttc tgaatgtaga cggaacagtg tggaagcaga aggctttttt
1681        aactcatccg tttgccaatc attgcaaaca actgaaatgt ggatgtgatt gcctcaataa
1741        agctcgtccc cattgcttaa gccttcaaaa aaaaaaaaaa aaaaaaaaaa aaaaaaaaa
1801        aaaaa
```

Human Cx31.9, c1
LOCUS       NM_152219 2094 bp mRNA linear PRI 23 Aug. 2004
DEFINITION  *Homo sapiens* gap junction protein, chi 1, 31.9 kDa (connexin 31.9)
            (GJC1), mRNA.
(SEQ ID NO: 27)

```
   1        aaatgaaaga gggagcagga ggcgccggtc ccagccacct cccaaggtcc ctggctcagc
  61        tctgacaccc cagtcccggc cccagggtga gtggggttgg gtggcggttt agggcacca
 121        ggggcgtgtg gggaccctgtg taagtgtggg gtggggagga tctcaggaga tgtggaggct
 181        ggaggcacag gaggccaggg aggagggaga agcctggtgc cgcactccca ccacgctggg
 241        gtaggagggc aggacacctc cgacaaagg accctgtgag agttatgaaa gcggagttgc
 301        ctctgtacca gccccccacc ctgagaggag ttcactgcag taaaaatggt gagagaaatg
 361        gtgggccaag aaaggagtgg tctcgctgcc tctgccactc ccactcctcc catgggcacc
 421        aaattgggtc tagcgtctcg ggttcgaggc tccactcttc ccacagcatc cttgacagct
 481        aagggcaccg ctgggtttcc gcttccgaaa ccaggcaagt cagggctgg tccagctgat
```

-continued

```
 541    ctccaaggtc cttcctaaga atctgggatc tggaggatcc cagggtcgaa cggagacggc
 601    tcaggggtg cggctaaaat gcaaatgggg gatcctcccc agcacccatc ggtcccaaag
 661    agaaggtaac ccatagctga gcgtcgcctg ctcccctcgg gccctcccgt ggccctccgt
 721    ttcatactgg tctcatcgct aaacccgggc ctctcctacc tcacgactca ccctgaagtc
 781    agagaaggtc caacggaccc caccccgata ggcttggaag gggcaggggt ccctgacttg
 841    ccccatcccc tgactcccg ccccgcgtcc ccagcgccat ggggagtgg cgttcctgg
 901    gctcgctgct ggacgccgtg cagctgcagt cgccgctcgt gggccgcctc tggctggtgg
 961    tcatgctgat cttccgcatc ctggtgctgg ccacggtggg cggcgccgtg ttcgaggacg
1021    agcaagagga gttcgtgtgc aacacgctgc agccgggctg tcgccagacc tgctacgacc
1081    gcgccttccc ggtctcccac taccgcttct ggctcttcca catcctgctg ctctcggcgc
1141    ccccggtgct gttcgtcgtc tactccatgc accgggcagg caaggaggcg ggcggcgctg
1201    aggcggcggc gcagtgcgcc cccggactgc ccgaggccca gtgcgcgccg tgcgccctgc
1261    gcgcccgccg cgcgcgccgc tgctacctgc tgagcgtggc gctgcgcctg ctggccgagc
1321    tgaccttcct gggcggccag gcgctgctct acggcttccg cgtggcccg cacttcgcgt
1381    gcgccggtcc gccctgcccg cacacggtcg actgcttcgt gagccggccc accgagaaga
1441    ccgtcttcgt gctcttctat ttcgcggtgg ggctgctgtc ggcgctgctc agcgtagccg
1501    agctggggcca cctgctctgg aagggccgcc cgcgcgccgg ggagcgtgac aaccgctgca
1561    accgtgcaca cgaagaggcg cagaagctgc tcccgccgcc gccgccgcca cctattgttg
1621    tcacttggga agaaaacaga caccttcaag gagagggctc ccctggtagc ccccacccca
1681    agacagagct ggatgcccct cgcttccgta gggaaagcac ttctcctgca ggatggcatt
1741    gctctctccc cttccatggc acgtagtatg tgctcagtaa atatgtgttg atgagaaac
1801    tgaaggtgtc cccaggccta caccactgcc atgcccgaac actatccatg ctatggtggg
1861    caccatctct ctgatgacag ttctgtgtcc acaacccaga ccctccaca caaacccaga
1921    tggggctgtg ccgctgtttt ccagatgtat tcattcaaca atatttgta gggtacctac
1981    tgtgtgtcag aagatgttca agatcagcat catccgatgg aaatagcata tgagccatgt
2041    atgtagtttc aagtttttca ttagccgcat taaaaaagta aaggaaaca aatg
```

Human Cx 29/31.3, e1  
LOCUS       AF503615 840 bp mRNA linear PRI 7 Aug. 2002  
DEFINITION  *Homo sapiens* connexin 31.3 mRNA, complete cds.  
(SEQ ID NO: 28)

```
   1    atgtgtggca ggttcctgcg gcggctgctg gcggaggaga gccggcgctc caccccgtg
  61    gggcgcctct tgcttcccgt gctcctggga ttccgccttg tgctgctggc tgccagtggg
 121    cctggagtct atggtgatga gcagagtgaa ttcgtgtgtc acacccagca gccgggctgc
 181    aaggctgcct gcttcgatgc cttccacccc ctctccccgc tgcgtttctg ggtcttccag
 241    gtcatcttgg tggctgtacc cagcgccctc tatatgggtt tcactctgta tcacgtgatc
 301    tggcactggg aattatcagg aaaggggaag gaggaggaga ccctgatcca gggacgggag
 361    ggcaacacag atgtcccagg ggctggaagc ctcaggctgc tctgggctta tgtggctcag
 421    ctgggggctc ggcttgtcct ggaggggca gccctgggt tgcagtacca cctgtatggg
 481    ttccagatgc ccagctcctt tgcatgtcgc cgagaacctt gccttggtag tataacctgc
 541    aatctgtccc gcccctctga aagaccatt ttcctaaaga ccatgtttgg agtcagcggt
 601    ttctgtctct tgtttacttt tttggagctt gtgcttctgg gtttggggag atggtggagg
 661    acctggaagc acaaatcttc ctcttctaaa tacttcctaa cttcagagag caccagaaga
```

```
721    cacaagaaag caaccgatag cctcccagtg gtggaaacca agagcaatt tcaagaagca 781    gttccaggaa gaagcttagc ccaggaaaaa caaagaccag ttggacccag agatgcctga
```

Human Cx 25
LOCUS       HSA414563 672 bp DNA linear PRI 30 Nov. 2001
DEFINITION  Homo sapiens CX25 gene for connexin25.
(SEQ ID NO: 29)

```
  1    atgagttgga tgttcctcag agatctcctg agtggagtaa ataaatactc cactgggact 61    ggatggattt ggctggctgt cgtgtttgtc ttccgtttgc tggtctacat ggtggcagca 121    gagcacatgt ggaaagatga gcagaaagag tttgagtgca acagtagaca gcccggttgc 181    aaaaatgtgt gttttgatga cttcttcccc atttcccaag tcagactttg ggccttacaa 241    ctgataatgg tctccacacc ttcacttctg gtggttttac atgtagccta tcatgagggt 301    agagagaaaa ggcacagaaa gaaactctat gtcagcccag gtacaatgga tgggggccta 361    tggtacgctt atcttatcag cctcattgtt aaaactggtt ttgaaattgg cttccttgtt 421    ttattttata agctatatga tggctttagt gttccctacc ttataaagtg tgatttgaag 481    ccttgtccca acactgtgga ctgcttcatc tccaaaccca ctgagaagac gatcttcatc 541    ctcttcttgg tcatcaccte atgcttgtgt attgtgttga atttcattga actgagtttt 601    ttggttctca agtgctttat taagtgctgt ctccaaaaat atttaaaaaa acctcaagtc 661    ctcagtgtgt ga
```

Human Cx40.1
LOCUS       HSA414564 1113 bp mRNA linear PRI 30 Nov. 2001
DEFINITION  Homo sapiens mRNA for connexin40.1 (CX40.1 gene).
(SEQ ID NO: 30)

```
   1    atggaaggcg tggacttgct agggtttctc atcatcacat taaactgcaa cgtgaccatg 61    gtaggaaagc tctggttcgt cctcacgatg ctgctgcgga tgctggtgat tgtcttggcg 121    gggcgacccg tctaccagga cgagcaggag aggtttgtct gcaacacgct gcagccggga 181    tgcgccaatg tttgctacga cgtcttctcc cccgtgtctc acctgcggtt ctggctgatc 241    cagggcgtgt gcgtcctcct ccccctccgcc gtcttcagcg tctatgtcct gcaccgagga 301    gccacgctcg ccgcgctggg ccccgccgc tgccccgacc ccgggagcc ggcctccggg 361    cagagacgct gcccgcggcc attcggggag cgcggcggcc tccaggtgcc cgacttttcg 421    gccggctaca tcatccacct cctcctccgg accctgctgg aggcagcctt cggggccttg 481    cactactttc tctttggatt cctggccccg aagaagttcc cttgcacgcg ccctccgtgc 541    acgggcgtgg tggactgcta cgtgtcgcgg cccacagaga gtccctgct gatgctgttc 601    ctctgggcgg tcagcgcgct gtcttttctg ctgggcctcg ccgacctggt ctgcagcctg 661    cggcggcgga tgcgcaggag gccgggaccc ccacaagcc cctccatccg gaagcagagc 721    ggagcctcag gccacgcgga gggacgccgg actgacgagg agggtgggcg ggaggaagag 781    ggggcaccgg cgcccccggg tgcacgcgcc ggaggggagg gggctggcag ccccaggcgt 841    acatccaggg tgtcagggca cacgaagatt ccggatgagg atgagagtga ggtgacatcc 901    tccgccagcg aaaagctggg cagacagccc cggggcaggc ccaccgaga ggccgcccag 961    gaccccaggg gctcaggatc cgaggagcag ccctcagcag ccccagccg cctggccgcg 1021    cccccttcct gcagcagcct gcagccccct gacccgcctg ccagctccag tggtgctccc 1081    cacctgagag ccaggaagtc tgagtgggtg tga
```

Human Cx 62
LOCUS       HSA414565 1632 bp DNA linear PRI 30 Nov. 2001
DEFINITION  Homo sapiens CX62 gene for connexin62.
(SEQ ID NO: 31)

```
  1    atgggggact ggaacttatt gggtggcatc ctagaggaag ttcactccca ctcaaccata 61    gtggggaaaa tctggctgac catcctcttc atcttccgaa tgctggtact tgtgtggct
```

-continued

```
 121        gctgaggatg tctgggatga tgaacagtca gcatttgcct gcaacacccg gcagccaggt
 181        tgcaacaata tctgttatga tgatgcattc cctatctctt tgatcaggtt ctgggtttta
 241        cagatcatct ttgtgtcttc tccttctttg gtctatatgg gccatgcact ttataggctc
 301        agggcctttg agaaagacag gcagaggaaa aagtcacacc ttagagccca gatggagaat
 361        ccagatcttg acttggagga gcagcaaaga atagataggg aactgaggag gttagaggag
 421        cagaagagga tccataaagt ccctctgaaa ggatgtctgc tgcgtactta tgtcttacac
 481        atcttgacca gatctgtgct ggaagtagga ttcatgatag gccaatatat tctctatggg
 541        tttcaaatgc acccctttta caaatgcact caacctcctt gccccaatgc ggtggattgc
 601        tttgtatcca ggcccactga gaagacaatt ttcatgcttt ttatgcacag cattgcagcc
 661        atttccttgt tactaatat actggaaata tttcatctag gcatcagaaa aattatgagg
 721        acactttata agaaatccag cagtgagggc attgaggatg aaacaggccc tccattccat
 781        ttgaagaaat attctgtggc ccagcagtgt atgatttgct cttcattgcc tgaaagaatc
 841        tctccacttc aagctaacaa tcaacagcaa gtcattcgag ttaatgtgcc aaagtctaaa
 901        accatgtggc aaatcccaca gccaaggcaa cttgaagtag acccttccaa tgggaaaaag
 961        gactggtctg agaaggatca gcatagcgga cagctccatg ttcacagccc gtgtccctgg
1021        gctggcagtg ctggaaatca gcacctggga cagcaatcag accattcctc atttggcctg
1081        cagaatacaa tgtctcagtc ctggctaggt acaactacgg ctcctagaaa ctgtccatcc
1141        tttgcagtag gaacctggga gcagtcccag gacccagaac cctcaggtga gcctctcaca
1201        gatcttcata gtcactgcag agacagtgaa ggcagcatga gagagagtgg ggtctggata
1261        gacagatctc gcccaggcag tcgcaaggcc agctttctgt ccagattgtt gtctgaaaag
1321        cgacatctgc acagtgactc aggaagctct ggttctcgga atagctcctg cttggatttt
1381        cctcactggg aaaacagccc ctcacctctg ccttcagtca ctgggcacag aacatcaatg
1441        gtaagacagg cagccctacc gatcatggaa ctatcacaag agctgttcca ttctggatgc
1501        tttcttttc ctttctttct tcctggggtg tgtatgtatg tttgtgttga cagagaggca
1561        gatggagggg gagattattt atggagagat aaaattattc attcgataca ttcagttaaa
1621        ttcaattcat aa
```

Various aspects of the invention will now be described with reference to the following experimental section which will be understood to be provided by way of illustration only and not to constitute a limitation on the scope of the invention.

The following Examples are offered by way of illustration and not by way of limitation.

Example 1: In Vivo Analysis

Materials and Methods
Laser Treatment

Female Wistar rats (d32-34) were raised under conditions consistent with the ARVO Resolution on the Use of Animals in Research. Animals were anaesthetised by administrating a 1:1 mixture of Hypnorm™ (10 mg/ml, Jansen Pharmaceutica, Belgium) and Hypnovel® (5 mg/ml, Roche products Ltd, New Zealand) at a dose of 0.083 ml/100 g body weight in the peritoneum of the animal.

Excimer laser treatment was performed through the intact epithelium using a Technolas 217 Z excimer laser (Bausch & Lomb Surgical, USA). The eye was centered at the middle of the pupil and ablation was performed with the following parameters: treatment area was of 2.5 mm diameter and of 70 μm depth. This resulted in the removal of a small thickness of the anterior stroma and of the whole epithelium. Excimer laser treatment was preferentially used to produce reproducible lesions and investigate the effects of connexin43 AS ODNs on corneal remodeling and engineering after trauma.

Following surgery, all animals were placed in individual cages and closely monitored for any discomfort. Post-surgical in vivo evaluation was achieved using a slit lamp biomicroscope and/or a slit scanning in vivo confocal microscope.

Slit Scanning In Vivo Confocal Microscopy

Prior to, and following corneal laser treatment, each animal was observed clinically using a Confoscan 2 (Fortune Technologies America, USA) slit scanning in vivo confocal microscope. The Confoscan 2 is a variant of slit scanning technology with the distinct advantage of direct digitization of the images at the time of acquisition. Animals were anaesthetized and each of them was placed onto a specially designed platform that was adjusted at the level of the in vivo confocal microscope objective lens in front of the acquisition head.

The slit scanning in vivo confocal microscope allows optical dissection of the living cornea at different levels through the whole corneal thickness. The examination starts from the endothelium and the number of the antero-posterior sections depends upon the customized settings. The slit scanning technology utilizes an objective lens that moves back and forward along the axis perpendicular to the examined area. In brief, the hardware consists of a halogen lamp (100 W/12 V), two slits, two tube lenses, a front objective lens, and a highly sensitive digital (CCD) camera. Prior to scanning, a drop of Viscotears (CIBAVision Ophthalmics) is placed on the tip of the objective lens as an immersion substance. During scanning, the eye of the animal is held wide open and orientated so that the corneal plane is always perpendicular to the optical axis of the magnification lens (40×, N.A 0.75). The image acquisition time is approximately 14 seconds. The gel, not the objective lens contacts the eye at all times. For the rat cornea, up to 250 sequential digital images were obtained per examination, and were directly saved to a hard disk drive. Acquisition parameters were adjusted during the preliminary experiments and were kept constant for all subsequent experiments. They were as follows: the light intensity was decreased to half the intensity generally used for human patients, four passes (one pass is considered as being a full back and forward movement) were used, and a 400 μm working distance was selected. For the rat cornea, centration is facilitated by clear visualization of the pupil, which provides very good topographical repeatability.

In Vivo Confocal Images

All images acquired with the slit scanning in vivo confocal microscope were stored onto the hard disc drive and subsequently analyzed by NAVIS proprietary software (Confoscan 2, Nidek Co Ltd).

Stromal dynamics were evaluated following stereological principles. Cell counts were recorded at the anterior and posterior stromal positions. The main stereological component was provided by the in vivo confocal microscope itself as it functions as an optical dissector (a probe that samples with equal probability particles in space). Indeed, the in vivo confocal microscope provides thin optical slices of specified volume, with each being a dissected tissue sample. As a result, counting stromal cells consists of choosing a pair of frames (consecutive pictures recorded by the in vivo confocal microscope), one frame having particles (stromal cells) in focus, and the co-frame showing a defocused but recognizable image of the same particles (optical shadows). The number of cells (n) is recorded from the clearest frame in a defined area A (μm$^2$). The distance d (μm) between the two frames is also recorded. The number of cells per unit volume (V) therefore equals to: V=Number of cells (n)/d (μm)×A (μm$^2$).

Ex Vivo Confocal Images

Appropriate corneal sections were immunohistochemically stained with different markers for different purposes. Staining with the nuclear stain Hoechst 33 258 was used to estimate the number of epithelial and stromal cells at the central or the peripheral cornea. For this purpose using AnalySIS® 3. 2 software (Soft Imaging System, USA), the area of interest was first freehand drawn onto the TIFF file image of the appropriate region of the cornea and the value of the area was automatically given by the software. Using the manual count option, cells were then counted within that area and expressed per unit area.

Antisense Compound Application

30% Pluronic acid gel (BASF Corp) in phosphate buffered saline (molecular grade water) was used to deliver unmodified α1 connexin (connexin43) specific antisense ODNs to the subconjunctiva of anaesthetized rats following photorefractive keratectomy. In a pre-trial using an FITC tag, this formulation was shown to remain in the anterior chamber of the eye for up to 24 hours (not shown).

The antisense molecule used in these experiments was DB1 ((GTA ATT GCG GCA GGA GGA ATT GTT TCT GTC) (SEQ ID NO: 65). Addition of an FITC tag to DB1 ODN, viewed using confocal laser scanning microscopy, demonstrated intracellular penetration of the probe.

The ODN was applied at a 2 μM final concentration.

Monitoring Tissue Engineering or Remodeling Effects

After antisense application, the corneas were examined using a slit scanning in vivo confocal microscope at 2 h, 12 h, 24 h, 48 h, 72 hr, 1 week and 2 weeks post laser surgery. Control rats received laser surgery only.

Table 1 summarizes the number of corneas investigated at each time point.

TABLE 1

Number of control (C) and AS (ODN) treated corneas used for the in vivo follow-up using slit scanning in vivo confocal microscopy.

| | Within 2 hr surgery | 12 hr post-surgery | 24 hr post-surgery | 48 hr post-surgery | 72 hr post-surgery | 1 week post-surgery | 2 weeks post-surgery |
|---|---|---|---|---|---|---|---|
| Number of eyes (n) | 18 C 18 ODN | 10 C 10 ODN | 18 C 18 ODN | 10 C 6 ODN | 6 C 6 ODN | 4 C 4 ODN | 5 C 5 ODN |

ODN = AS ODN treated eyes (single administration after laser surgery)

Each cell layer of the cornea was analyzed and the cell type, number and appearance compared between the control and ODN treated groups.

Re-Epithelialization:

Treatment with anti-connexin43 ODNs promoted epithelial recovery. In 90% of AS ODN treated corneas, sliding epithelial cells were observed within 12 hours after PRK laser surgery, compared to none in controls (FIG. 1B). At this stage, only static endothelial cells were present in 30% control corneas (FIG. 1A) By 24 hours epithelial cells were seen in all controls and antisense treated corneas but 72% of treated versus 61% of controls showed actively sliding cells. This indicates that re-epithelialization is proceeding faster in the connexin43 specific AS ODN treated corneas than in controls.

Stromal Cell Densities:

Using a paired samples t-test with repeat measures to compare cell densities in the anterior and posterior stroma within each group as a function of time and a Mann Whitney non parametric statistical test to compare stromal cell counts between control and ODN treated corneas at the selected time points, the only statistically significant results were found at 24 hr post-laser surgery (Table 2). At this time point, in the control and ODN treated groups stromal cell density in the anterior stroma has increased considerably compared to the pre-surgery values (p value <0.05). In the posterior stroma of control corneas, stromal cell density has also increased compared to the pre-surgery value (p value <0.05) whilst in the posterior stroma of ODN treated corneas, stromal cell density is not statistically significantly different from the pre-surgery value (p value >0.05). When comparing stromal cell density between the two groups at the anterior and posterior stroma, the ODN treated corneas always showed lower stromal cell densities than the control corneas (p-value <0.05). This supports the idea that a smaller number of cells are involved in stromal re-modeling or engineering in the ODN treated corneas compared to the control corneas. This is the first report showing that application of anti-connexin43 ODNs reduces hypercellularity at the site of surgery. Ex vivo histochemical analysis (Example II) shows that this hypercellularity is associated with myofibroblasts which induce unwanted stromal matrix remodeling and scarring.

TABLE 2

Stromal cell counts in control and AS ODN treated corneas prior to and 24 hr following photorefractive keratectomy. Cell densities are given as means followed by standard deviations.

| Treatment | Time points | Anterior stromal cell count (#cells/mm$^3$) | Posterior stromal cell count (#cells/mm$^3$) |
|---|---|---|---|
| Control | Pre-surgery | 36469 ± 11122 (n = 17) | 33909 ± 8753 (n = 17) |
| ODN | Pre-surgery | 36769 ± 10932 (n = 17) | 34382 ± 8667 (n = 14) |
| Control | 24 hr post-surgery | 144643 ± 60989 (n = 17) | 46901 ± 26964 (n = 17) |
| ODN | 24 hr post-surgery | 93468 ± 53548 (n = 17) | 33510 ± 11350 (n = 14) |

Example II—Ex Vivo Analysis

Materials and Methods
Histology: Tissue Collection and Fixation

Appropriate numbers of animals (Wistar rats) were terminated at selected time points following photorefractive keratectomy and DB1 anti-connexin43 ODNs were administered to anaesthetized rats as described in experiment 1 above and corneal sections were prepared for histological analysis. Control rats had received laser surgery only. Whole eyes and control tissues were rinsed in Oxoid PBS prior to embedding in Tissue-Tek® OCT (Sakura Finetek, USA) and freezing in liquid nitrogen. When necessary (for the use of some antibodies), frozen tissues were later fixed in cold (−20° C.) acetone for 5 min after being cryocut.
Tissue Cutting The procedure for cryosectionning was as follows: frozen blocks of unfixed tissue were removed from −80° C. storage and placed in the Leica CM 3050S cryostat for about 20 min to equilibrate to the same temperature as the cryostat (i.e. −20° C.). When equilibration of the tissue was achieved, the specimen was mounted onto a specimen disc with Tissue Tek® OCT. Sections of 12 μm (for H/E staining) or 25 μm thick (for immunolabeling) were cut and placed on Superfrost® Plus slides (Menzel-Gleser, Germany). Immediately following cryocutting, tissue blocks were placed back to −80° C. storage and slides supporting cryosections were either used immediately or stored at −80° C. Sectioning occurred parallel to the optical axis of the eye.

Haematoxylin/Eosin (H/E) Staining and Nuclear Staining

Figure 2:
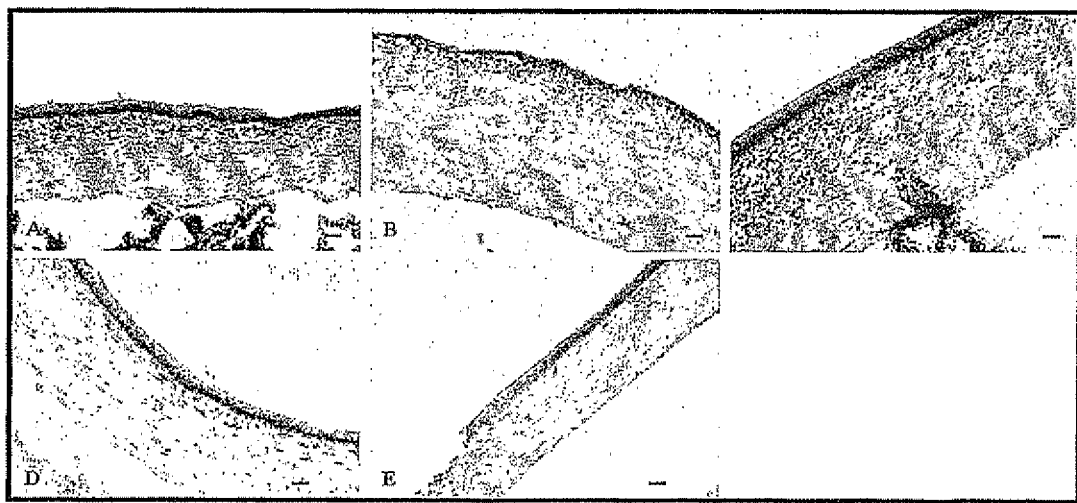
FIG. 2 shows histological examination of corneal remodeling in control (2A, 2B, 2C) and antisense oligodeoxynucleotide treated rat corneas (2D, 2E) 24 hours after excimer laser photoablation.

Slides were placed in glass racks to facilitate immersion in a series of different staining reagents. Racks were agitated when placing them into reagents to break surface tension and to drain them between each solution change. Prior to Gill's II Haematoxylin/Eosin staining, slides that were stored at −80° C. were first warmed up to room temperature for 1-2 min, then either fixed in cold acetone first and/or immediately hydrated with a quick dip in tap water. Slides were stained in Gill's II Haematoxylin for 2 min, after which excess stain was rinsed off in tap water. Stain differentiation was achieved by dipping in Scott's tap water substitute (STWS) for 4 sec. A rinse in running tap water for 1 min was then performed before staining in 1% eosin for 30 consecutive dips. Finally, sections were quickly rinsed in tap water, dehydrated through 95%, 100% EtOH, cleared in xylene, and mounted with DPX mounting medium (Sigma). For nuclear counter staining (in parallel with H/E or immunohistochemical analysis) Hoechst 33 258 (Sigma) was used. Measurement of cornea thickness was carried out on H/E stained sections.
Immunohistochemistry Sections were immunolabeled for connexin43 using a site-specific monoclonal antibody, for myofibroblasts using an antibody recognizing alpha smooth muscle actin, for basal lamina deposition with an anti-laminin-1 antibody. In addition anti-vimentin antibodies were used to differentiate stromal keratocytes from myofibroblasts and a Ki-67 antibody was used to show cell proliferation.
Ex Vivo Histological Analysis Results showed that lesions made by excimer photoablation had closed by 24 hr post-surgery (FIG. 2). The typical invasion of the stroma by mononucleated/multinucleated and/or round, ovoid cells at the periphery and at the center of the cornea was observed in both groups, most pronounced at 24 hr post-surgery, but with the antisense ODN treated group showing a significantly smaller number of these cells than the control group (FIG. 2A,B,C). This parallels the findings from the in vivo confocal photomicrographs shown in Example 1. The epithelium thickness was variable in control corneas as seen in FIG. 2 at the site of laser induced lesion (Figure A, B), and in the stoma beneath the ablated area (Figure A,B) and in the peripheral stroma (Figure C) there was an extensive invasion by round cells (hypercellularity) in control corneas. Also observed was a pronounced stromal edema in Figure B and Figure C. In the antisense ODN treated corneas the epithelium was of even thickness (Figure D,E) and in the central region (Figure D) and in the peripheral stroma (Figure E) there was little sign of stromal edema. Moreover, in the stroma there were few round cells present. Scales bars in FIG. 2 represent 20 microns.

Changes in stromal thickness following treatment with connexin43 ODNs after laser treatment are shown in Table 3, which compares changes in stromal thickness between control and ODN treated corneas. Stromal thicknesses were measured from appropriate histological stained sections. Statistical analysis of the data obtained for the ODN treated group using a paired samples t-test showed that at all three time points investigated (24 hr, 48 hr and 72 hr post-surgery) central stromal thickness is statistically significantly thinner than pre-surgery value (p values <0.05) and peripheral stromal thickness is not significantly different from pre-surgery values. In contrast, control corneas show significant stromal swelling (edema) (FIG. 2 A, B, C) in both central and peripheral cornea (where the stroma doubles in thickness compared to pre-surgery values).

TABLE 3

Changes in stromal thickness following excimer laser surgery in control and AS treated corneas.

| Treatment | Time points | mean central stromal thickness (μm) | mean peripheral stromal thickness (μm) |
|---|---|---|---|
| Normal (no surgery) | Pre-surgery | 250 (n = 6)* | 110 (n = 10) |
| Control | 24 hr post-surgery | 318 (n = 6) | 290 (n = 6) |
| ODN treated | | 190 (n = 5) | 132 (n = 5) |
| Control | 48 hr post-surgery | 307 (n = 6) | 206 (n = 5) |
| ODN treated | | 158 (n = 5) | 105 (n = 5) |
| Control | 72 hr post-surgery | 292 (n = 6) | 201 (n = 6) |
| ODN treated | | 142 (n = 5) | 99 (n = 5) |

Cornea which is not subjected to surgery had a central stromal thickness of 250 μm, but excimer laser surgery was used to remove 70 μm of corneal tissue (including the epithelium and part of the stroma). The normal corneal epithelium is 50 μm thick (on average) and therefore 20 μm of stromal tissue was removed by laser surgery. Therefore, to statistically compare the central stromal thickness at 24 hr, 48 hr and 72 hr post-wounding to the pre-surgery central stromal thickness, an adjusted thickness loss and a central pre-surgery stromal thickness of 250−20=230 μm was used.

Figure 3:
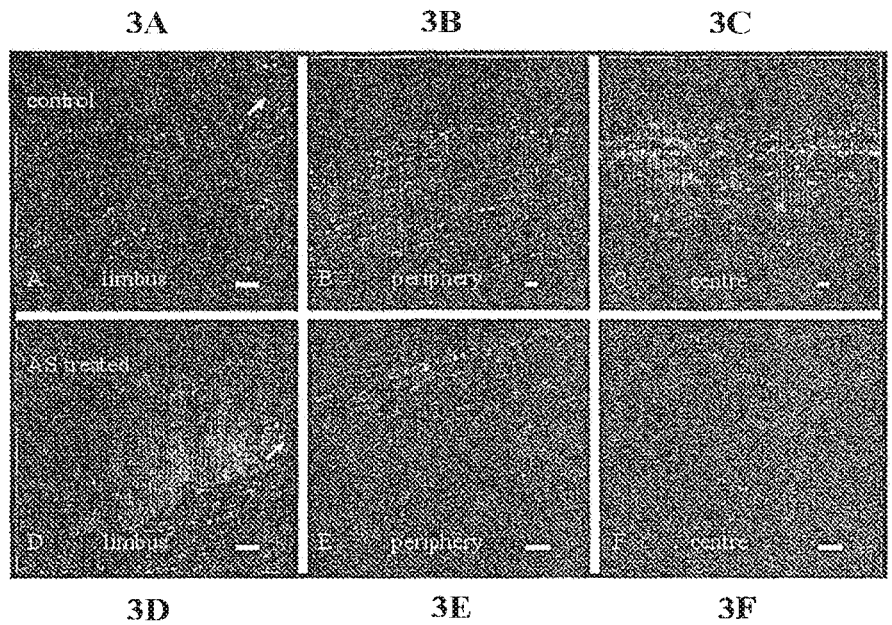
FIG. 3 provides micrograph images showing expression of connexin 43 protein in control (3A, 3B, 3C) and antisense oligodeoxynucleotide treated corneas (3D, 3E, 3F) at 24 hours after excimer laser ablation. The results demonstrate that connexin43 protein levels are reduced following treatment with anti-connexin43 ODNs and results in a smaller degree of cell recruitment in the stroma.

Reduction in Connexin43 Expression is Associated with Reduced Stromal Invasion and Reduced Epithelial Hyperplasia Microscopial observations showed a reduced level of connexin43 present in ODN treated corneas compared to control corneas. FIG. 3 shows combined micrograph images. Top row shows control corneas, the bottom row shows antisense ODN treated corneas. The typical invasion of the stroma by round cells was seen in both groups within 24 hours at the limbal, peripheral and central areas. However, a smaller density of round cells was exhibited in ODN treated corneas. At the limbus in both groups anti-connexin43 was evenly distributed throughout the stroma (3A, D) but the treated groups had less label in the periphery (3E) compared to controls (3B). By this stage connexin43 levels had returned to normal in the epithelium of both groups but control groups showed a scar like stroma (3C) or hyperplasia (see FIG. 4 below) whereas in antisense treated corneas a normal epithelium with normal levels of connexin43 was seen (3F). Scale bars A, D, E, F represent 10 microns; B and C represent 20 microns. In these figures connexin43 appears as white punctate labeling with cell nuclei appearing grey. The results shown in FIG. 3 suggest that connexin43 protein levels are reduced following treatment with anti-connexin43 ODNs and results in a smaller degree of cell recruitment in the stroma. In addition, only 7% of ODN treated corneas (0% at 24 hr post-surgery, 0% at 48 hr post-surgery, 20% at 72 hr post-surgery) show signs of epithelial hyperplasia compared to 31% control corneas (25% at 24 hr post-surgery, 67% at 48 hr post-surgery, 0% at 72 hr post-surgery). This was assessed on H/E stained and Ki-67 labeled sections.

Myofibroblast Labeling

Figure 4:
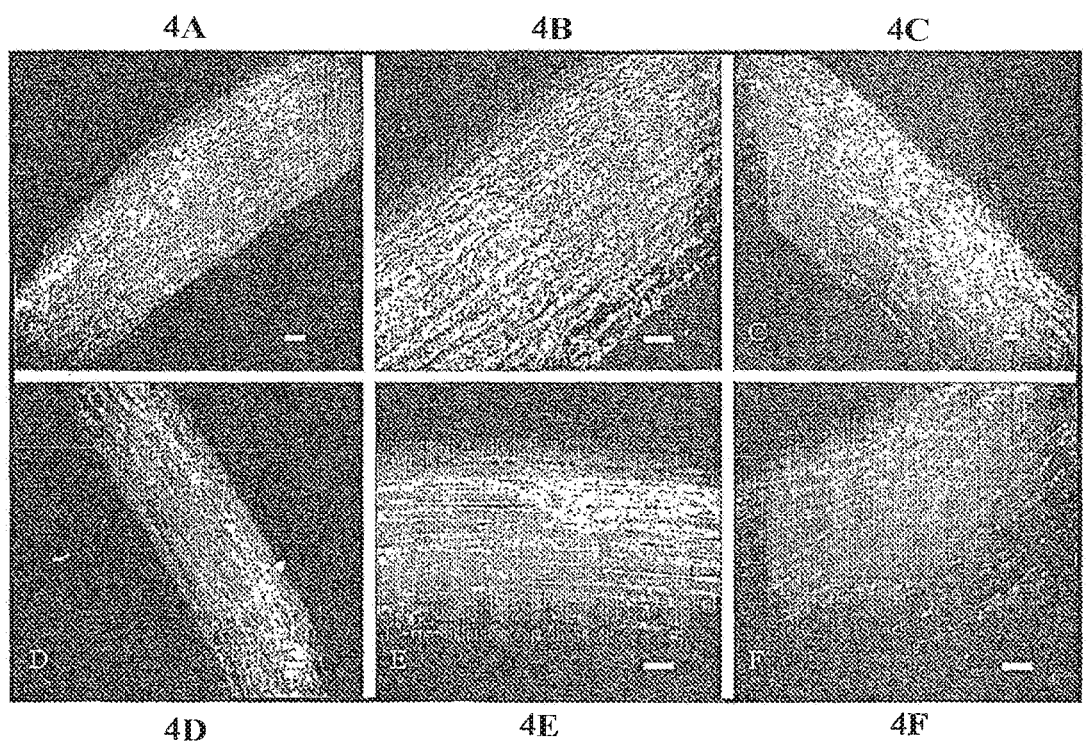
FIG. 4 shows myofibroblast labeling 1 week after surgery using alpha smooth muscle actin antibodies.

Labeling with vimentin antibodies indicated that the increased cell numbers in the stroma of control corneas compared with AS ODN treated corneas were not of undifferentiated keratocyte origin and labeling was therefore carried out with alpha-smooth muscle actin antibodies. This labeling showed that control corneas had a higher number of myofibroblasts beneath the site of surgery, but also in the surrounding peripheral stroma. This increase in myofibroblast numbers and area affected was evident at 24 hours and persisted over 48 and 72 hours through to at least one week after surgery (Table 4). FIG. 4 shows myofibroblast labeling (anti-alpha smooth muscle actin) at 1 week post-laser surgery. FIGS. 4 A, B, and C are controls; and FIGS. 4 D, E, and F are antisense treated corneas. By one week post-wounding, in the control corneas, low to moderate numbers of myofibroblasts are present in the anterior half of the peripheral stroma (4A), moderate to dense levels are present in the mid-peripheral stromal regions (4 B), and moderate levels are seen in the anterior half of the stroma in central regions (4C). In contrast, in the treated corneas, very low numbers of myofibroblasts are present in peripheral (4D) or mid peripheral (4E) stroma and moderate to low numbers in central stroma (4F). In some cases in the central stroma, myofibroblasts are concentrated in the area just under the epithelium (not shown). Thus, the increased cell numbers seen in Example 1 (hyerpcellularity) and FIG. 2 above appears to be due to myofibroblast differentiation and invasion. Myofibroblasts are known to be responsible for scar tissue deposition in the stoma, with reduced crystalline deposition and increased secretion of wound collagen Ill (Ahmadi A. J. and Jakobiec F. A.; 2002; Int Ophthalmol Clin. Summer; 42(3):13-22.).

TABLE 4

Summary of alpha smooth muscle actin labeling for myofibroblast in control and antisense ODN treated corneas.

| Time | Locations | Control corneas | AS treated corneas |
|---|---|---|---|
| 24 hr post-surgery | Periphery | 80% D in whole st<br>20% M in whole st | 100% M in anterior 1/3 st |
| | Mid-periphery | 100% D in whole st | 100% M in anterior 1/3 st |
| | Centre | 100% L in anterior 3/4 st | 80% L in anterior 1/3 st<br>20% L below epi |
| 48 hr post-surgery | Periphery | 83% M in whole st<br>17% L in whole | 40% M in half anterior st<br>60% L in half anterior st |
| | Mid-periphery | 50% D in whole st<br>50% M in whole st | 100% D in half anterior st |
| | Centre | 17% L under epi<br>(hyperplasia)<br>50% D in whole st<br>33% M in whole st | 20% absent<br>80% M in anterior 3/4 st |

TABLE 4-continued

Summary of alpha smooth muscle actin labeling for myofibroblast in control and antisense ODN treated corneas.

| Time | Locations | Control corneas | AS treated corneas |
|---|---|---|---|
| 72 hr post-surgery | Periphery | 33% L in anterior half st 67% M in anterior half st | 40% L in anterior half st 60% M in anterior half st |
| | Mid-periphery | 33% L in whole st 67% D in whole st | 20% L in anterior half st 80% M in anterior half st |
| | Centre | 17% absent 50% D in whole st 33% M in whole st | 20% absent 40% L in anterior half st 40% M in anterior 3/4 st |
| 1 week post-surgery | Periphery | 60% M in half anterior st 40% L in half anterior st | 100% L in anterior 1/3 st |
| | Mid-periphery | 60% D in whole st 40% M in whole st | 100% L in anterior half st |
| | Centre | 60% M in anterior half st 40% L in anterior half st | 60% M in anterior half st 20% L in anterior half st 20% M under epi |

Numbers of myofibroblasts are quantified as dense (D), moderate (M), low (L) or absent. Percentages refer to proportions of animals affected at the specified levels. st=stroma, epi=epithelium. Significant differences between control and antisense treated corneas are highlighted in bold.

Basal Lamina Deposition

Figure 5:
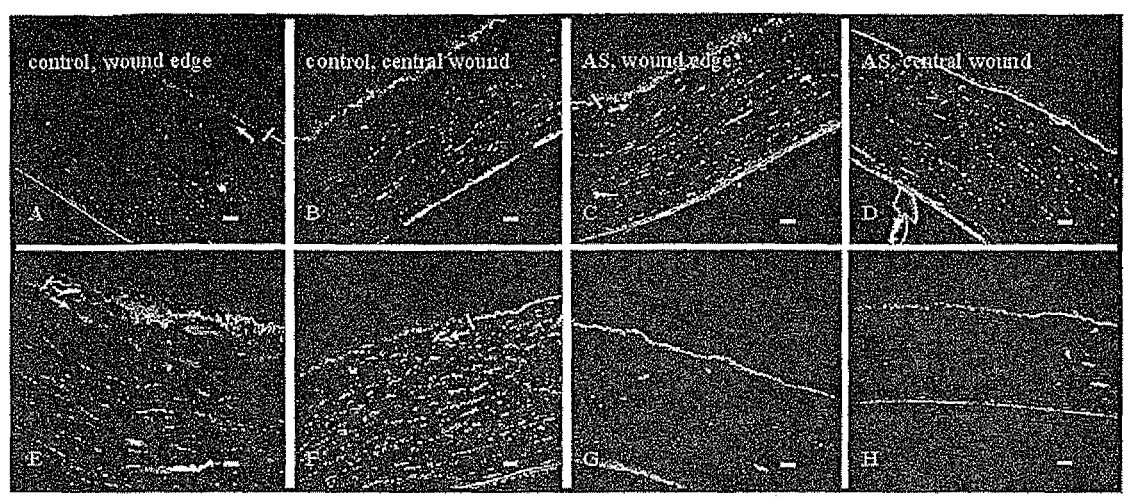
FIG. 5 shows laminin-1 labeling of control (5A, 5B) and connexin 43 antisense oligodeoxynucleotide treated corneas 24 hours (5A-5D) and 48 hours (5E-5H) after photorefractive keratectomy. At 24 hours controls had little and/or uneven laminin deposition at the edge of the ablated area (5A) and more centrally (5B) whereas antisense treated corneas showed a more regular deposition of laminin at both of these regions (5C, 5D). At 48 hours controls still do not have a continuous laminin deposition (5E—edge of the ablated area.

Following photorefractive keratectomy the basal lamina reforms along with the regrowing epithelium. Labeling with antibodies to laminin-1 shows that the reforming basal lamina is discontinuous and with an irregular epithelial-stromal attachment (FIG. 5). At 24 hours controls had little and/or uneven laminin deposition at the edge of the ablated area (FIG. 5A) and more centrally (FIG. 5B) whereas antisense treated corneas showed a more regular deposition of laminin at both of these regions (FIG. 5C, FIG. 5D). At 48 hours controls still do not have a continuous laminin deposition (FIG. 5E—edge of the ablated area; FIG. 5F—central) and it was very uneven (FIG. 5E). In contrast antisense ODN treated corneas had a continuous and relatively even basal lamina at the wound edge (FIG. 5G) and centrally (FIG. 5H). All scale bars in FIG. 5 represent 20 microns. Connexin43 antisense treated corneas formed a denser, more continuous basal lamina within 24 hours with less irregularity.

Figure 6:
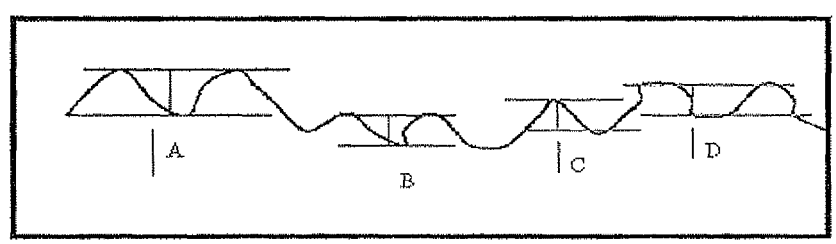
FIG. 6 shows a schematic diagram of laminin-1 irregularity quantification.

The laminin irregularity was quantified as shown in FIG. 6. The black solid line in FIG. 6 represents laminin-1 deposition. For each region the variance was measured as the difference between the top of a hill and the bottom of a valley (FIG. 6 A, B, C, D). Control corneas had a mean variance of 6.98 microns compared with 4.74 microns in antisense ODN treated corneas. The difference between the two groups was statistically significant ($p<0.0001$).

Example III—Ex Vivo Tissue Engineering

Corneas were placed into an ex vivo organ culture model and specific connexin modulated using antisense ODNs. Two connexins were targeted in these experiments, connexin43 and connexin31.1. Connexin43 downregulation is used to demonstrate that connexins can be regulated in vitro, and connexin31.1 was targeted because this connexin is expressed in the outer epithelial layers of the cornea in cells about to be shed from the cornea. The aim was to engineer a thickening of epithelial tissue by reducing connexin31.1 expression.

Materials and Methods 30-34 day old Wistar rats were euthanized with Nembutal or carbon dioxide and whole rat eyes dissected. The ocular surface was dissected, disinfected with 0.1 mg/ml penicillin-streptomycin for 5 minutes and rinsed in sterile PBS. The whole eye was then transferred onto a sterile holder in a 60 mm culture dish with the cornea facing up. The eyes were mounted with the corneal epithelium exposed at the air-medium interface and cultured at 34° C. in a humidified 5% $CO_2$ incubator in serum free medium (Opti-MEM, Invitrogen) for up to 48 hours. 100 μl of medium was added drop wise to the surface every eight to twelve hours to moisten the epithelium. Medium levels were maintained to the level of limbal conjunctiva.

Antisense oligomers were mixed with 30% (w/w) Pluronic F127 gel (Sigma) on ice to a final 2 μM concentration and 10 μl applied onto the corneas. Each treatment had a sample size of 3 to 4 corneas per experiment. Preliminary experiments showed that double treatments of our positive control, DB1, for 8 hours had little effect on connexin43 protein expression in our corneal culture. Corneas were therefore cultured for 24 hours and connexin specific oligomers applied every 8 hours.

Immunohistochemical labeling was carried out as in Experiment 2 above using antibodies to connexins 43, 26 (control) and 31.1. Tissue was also stained with H/E as above. Nuclei were counterstained with 0.2 μM propidium iodide. Images were collected on a Leica TCS 4D or TCS SP2 confocal laser scanning microscope with voltage and offset settings maintained within experimental groups to allow quantification of connexin levels. For quantification four optical slices through 3 microns were processed into a single extended focus optical image using the center of mass topographical projection option on the TCS 4D. Connexin label was quantified using NIH Image (Scion Corp. USA) after thresholding at 90-100 pixel intensity on the 256 grey scale image.

Figure 7:
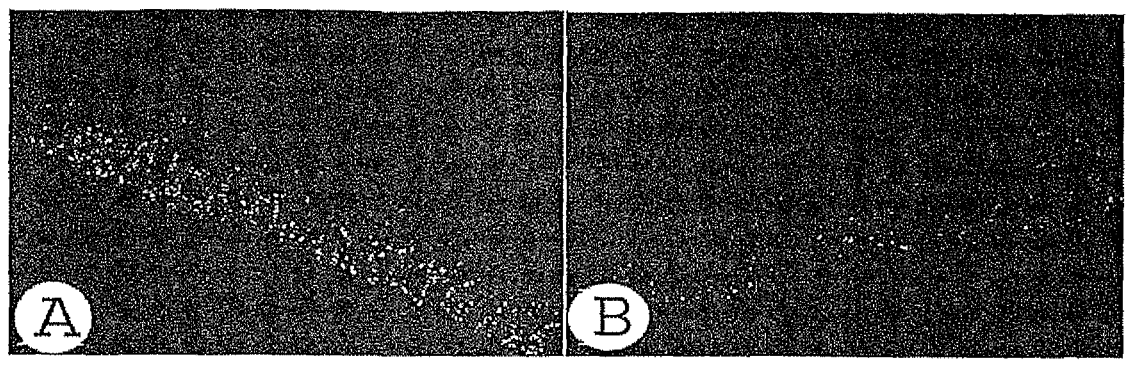
FIG. 7 shows immunohistochemical labeling for connexins 26 and 43 in control cultures (7A) and following three treatments with anti-connexin 43 oligodeoxynucleotides over a 24 hour period (7B), and after connexin31.1 specific antisense treatment (7C, 7D).
Figure 7:
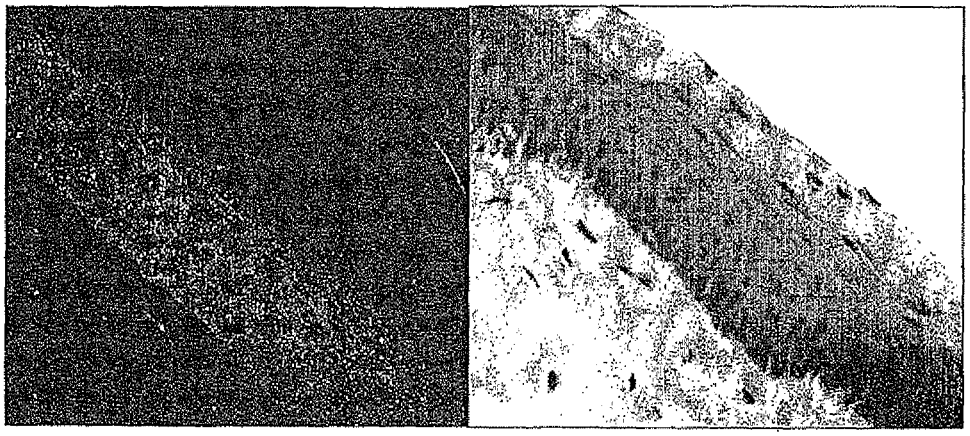

In corneas that have not undergone surgery, in vitro connexin turnover rates were relatively low compared to tissue remodeling processes in the excimer laser ablated corneas described in Examples 1 and 2 herein above. Nonetheless, after three treatments with antisense ODNs connexin levels were reduced by over 50% compared with controls (FIG. 7 A, B shows connexin43 reduction in AS ODN treated corneas compared with controls). Connexin26 levels remained constant when the connexin43 specific antisense ODNs were applied (indicating that the reduction in connexin levels was specific, not a side effect of the treatment. In these images connexin43 appears as heavier spots in the basal two layers of the epithelium, connexin26 as finer punctate labeling predominantly in layers 2-6. Connexin31.1 antisense ODNs reduced levels of connexin31.1 but preliminary results also showed that the epithelial thickness (number of layers) increased within 24 hours (FIG. 7 C, D). This increase in thickness was seen using H/E staining (FIG. 7D) and in the immunohistochemically (FIG. 7C) labeled sections.

The results described in this work form a basis for the use of connexin specific antisense ODNs in tissue-engineering, including specifically after excimer laser surgery of the cornea, or for in vitro organ culture for tissue engineering and transplantation. The experimental results provided herein demonstrate that a single treatment with connexin43 specific antisense ODNs following excimer laser photorefractive keratectomy has many beneficial uses, some of which are described hereinbelow.

Administration of connexin specific antisense ODNs promote epithelial cell movement. At 12 hr post-surgery 90% antisense treated corneas but no control corneas show the presence of sliding epithelial cells at the site of a laser induced lesion. Epithelial cells were present in 30% of control corneas but were static/non-sliding. Regulation of direct cell-cell communication by connexins can therefore be used to engineer changes in epithelial cell patterning.

Administration of connexin specific antisense ODNs promote controls hypercellularity associated with myofibroblast differentiation at the site of a laser induced lesion in the 24 hr to 48 hr post-surgery period. During this period, more control corneas (63%) than antisense ODN treated corneas (39%) show intense hypercellularity in the whole stroma. Regulation of direct cell-cell communication can therefore be used to modulate cell differentiation leading to modification of extracellular matrix.

Administration of connexin specific antisense ODNs controls stromal remodeling reducing haze at the site of a laser induced lesion in the 24 hr to 72 hr post-surgery period. In this period, more control corneas (64%) than antisense treated corneas (39%) show intense haze in the whole stroma.

Administration of connexin specific antisense ODNs inhibits stromal edema during the early stages of re-modelling. Regulation of direct cell-cell communication therefore improves outcomes from laser surgery.

Administration of connexin specific antisense ODNs reduces cell proliferation in the early stages of re-modelling. Regulation of direct cell-cell communication can therefore be used to regulate cell proliferation during tissue remodeling.

Administration of connexin specific antisense ODNs reduces epithelial hyperplasia by 78% (assessed from 24 hr to 72 hr post-surgery) enabling engineering of an even epithelium.

Administration of connexin specific antisense ODNs reduces myofibroblast activation up to 1 week post-surgery (and earlier loss of keratocytes). Regulation of direct cell-cell communication enables more precise control of tissue damage during surgical remodeling, providing improved predictability of outcome and fewer visual defects.

Administration of connexin specific antisense ODNs results in a more regular and denser epithelial-stromal adhesion matrix during tissue re-modelling. Regulation of direct cell-cell communication can therefore be used to engineer tissue basal laminae.

In addition, the ex vivo corneal culture model used herein indicates that regulation of direct cell-cell communication can be used to engineer tissue in vitro, for example increasing epithelial thickness using connexin31.1 antisense ODNs. This treatment also has implications in vivo, for example in the engineering a thicker cornea for the relief of corneal diseases such as keratoconus (a thinning of the epithelium).

The results show that active molecules which interfere with cell-cell communication can be used in tissue engineering and remodeling. Specifically, it is shown that antisense deoxynucleotides targeted at connexin proteins can be used in corneal re-modeling especially following corrective laser surgery, as well as for in vivo and in vitro tissue engineering.

The antisense compounds and methods described herein therefore have significant potential for improving the outcome of surgical interventions and ameliorating disease processes in the eye, and for tissue engineering.

Example IV

Ex Vivo Culture Model

Application of antisense oligodeoxynucleotides specific to the gap junction protein Connexin43 following brain or spinal cord injury in adult animal models blocks lesion spread, and reduces the inflammatory response and subsequent scar formation. We have taken our antisense approach even further and developed an ex vivo culture model for spinal cord segments and intact cords in order to elaborate repair strategies for established lesions.

Figure 8:
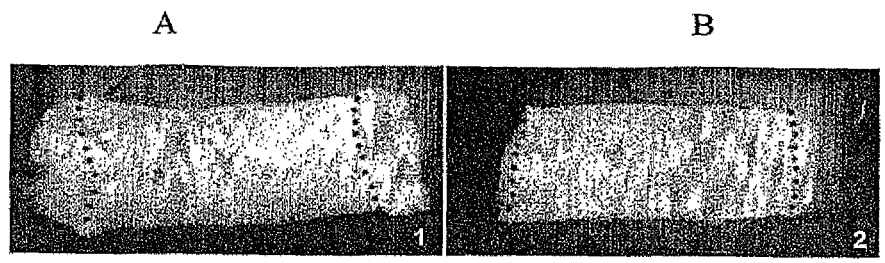
FIG. 8 shows spinal cord segments from P7 rat pups 24 hours after placing into culture. The control segment (1) is swollen (arrows) with tissue extruding from cut ends. Dotted lines mark the original excisions. Histological examination shows that cells are vacuolated and edemic. By day 5 these segments have activated microglia throughout and few surviving neurons. In contrast, the antisense treated segment (2) has significantly reduced swelling compared to controls (p<0.001) with minimal cellular edema and vacuolation. Even after 20 days in culture, neurons in the grey matter remain viable with activated microglia restricted to the outer edges.
Figure 9:
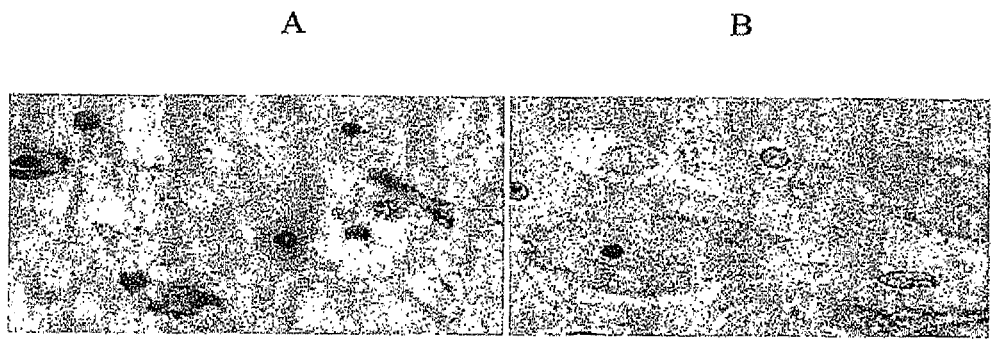
FIG. 9 shows neurons from a control treated segment (9A) and a Connexin43 antisense treated segment (9B). Neurons in a control segment are vacuolated and edemitous and the surrounding tissue is disrupted, but neurons in the treated segment appear healthy and viable.

Spinal cords are excised from P7-P14 rat pups and divided into caudal, thoracic and rostral segments. Antisense oligodeoxynucleotides were applied in a Pluronic gel to the cut ends of the spinal cord segments during placement in culture, this results in a reduction of Connexin43 protein levels for 24-48 hours, significantly improving viability of the tissue. The most immediate and notable observation is that swelling does not occur (FIG. 8 A-B, showing cord segments 24 hours after placing into culture). This treatment blocks the spread from the spinal cord cuts ends. Increased neuron survival in the grey matter of treated samples are clearly evident in the toluidine blue-stained resin sections (FIG. 9A). In sharp contrast, edema and vacuolation of neurons is seen throughout control tissue (untreated, gel only or gel with random oligodeoxynucleotides) in FIG. 9B.

Figure 10:
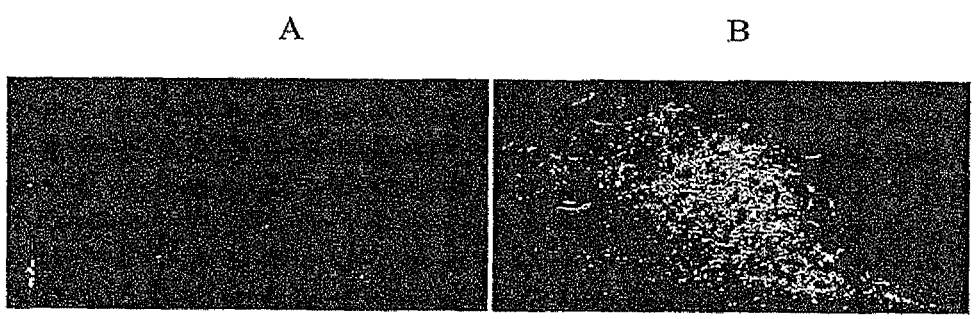
FIG. 10 illustrates MAP-2 immunolabeling near the ends of cultured spinal cord segments five days after placing into culture. Control segments have few viable neurons and little MAP-2 labelling (16% show any MAP-2 label) (10A) while 66% of treated segments have areas of MAP-2 expression at the cuts ends exposed to the medium and/or adjacent to remaining white matter material.

Subsequent labelling and immunohistochemical studies up to day 20 show that neurons in the treated cord segments (Neuronal-N labelling) survive for this period whereas few remain viable after as little as 3 days in the control segments. Isolectin-B4 labelling shows extensive activated (macrophagic phenotype) microglial invasion of control segments within five days in culture. In treated samples, activated microglial cells are restricted to the outer edges (where the white matter axon tracts were previously, and at the very cut ends). Notably, MAP-2 labelling, a marker for neuronal processes, indicates significant potential for regrowth in treated cord segments compared to control segments, which show no MAP-2 labelling at all (FIG. 10A-B).

Example V

Grafting of Peripheral Nerves Across Spinal Cord Lesions

For peripheral nerve grafting, we will retreat the tissue with Connexin43 specific antisense oligodeoxynucleotides at the time of grafting to prevent lesion spread from the graft site and microglial activation which leads to isolation of the graft from the host tissue neural population, restricting neuronal repair.

Peripheral Nerve Grafts:

Spinal cord segments are placed onto culture inserts (Millipore Millicell) in 35 mm dishes and the level of the culture medium raised until a miniscus forms over the segments. Connexin43 specific antisense oligodeoxynucleotides (30mers, 1 µM concentration) in a 30% Pluronic gel are placed immediately over the cord tissue. The gel sets as it warms to physiological temperatures and provides sustained release of the antisense oligomers. This treatment will reduce connexin43 protein levels for between 24 and 48 hours, with maximum reduction at 6-8 hours post-treatment. Such cord segments, stabilized in culture, and then re-exposed to incision trauma, shows the same symptoms as surgical intervention in vivo, including lesions expansion and tissue swelling into the cut area. This effect can be prevented by treatment with Connexin43 specific antisense oligomers at the time of the incision; and accordingly, the cut edges remain sharply defined with no obvious signs of edema or tissue swelling.

The segments are placed end to end but separated by a gap of 1-5 mm. After a one to three day stabilization period in culture, a graft of a sciatic nerve from a P7-P14 rat pup is placed across the gap. Previous studies have indicated that both sciatic nerve (or its saphenous branch)(Yick, L. W. et al., 1999, *Exp Neurol.* 159: 131-138; Aguayo, A. J. et al., 1981, *J. Exp. Biol.* 95: 231-240) or intercostal nerve (Cheng, H., et al., 1996, *Science,* 273: 510-513) grafting has considerable potential to induce axon elongation and the survival of neurons.

Immediately after grafting, re-treatment will commence with the Connexin43 antisense oligomers accompanied by neuronal behavior assessment over the subsequent days. Since the culture period after grafting are relatively short (up to 15 days) compared with in vivo studies (15 days to 7 months after surgery) a variety of markers to assess repair response as detailed below (Measuring outcomes) are used. Experiments are conducted with and without the addition of exogenous growth factors (such as acidic FGF or NGF) which might play a role in inducing neuronal proliferation and/or migration.

Example VI

Insertion of Schwann-Cell-Seeded Implants Between Segments Placed End to End

For implants between treated segments, Schwann cells have been selected as they have been shown to be strong promotors of axonal regeneration (Xu, X. M. et al., 1999, *J. Neurosci.* 11: 1723-1740; Keirstead, H. S. et al., 1999, *Exp. Neurol.* 159: 225-236).

Implanted cells can provide a permissive environment for central nervous system axon regeneration and have proven to be effective for inducing regrowth of axons. Schwann-cell-seeded mini-channel implants or matrigel placed between cord segments placed end to end are to be used for this application. The principle here is that for spinal repair interventions, one would ultimately wish to excise scar tissue and fill the space with implant material. The methods used are described by Morrissey et al. and Xu et al. (Morrissey, T. K. et al., 1991, *J. Neurosci.* 11: 2433-2442; Xu, X. M. et al., 1995, *J. Comp. Neurol.* 351: 145-160). Essentially, sciatic nerves are obtained from adult rats, the epineurium and connective tissue are then removed and 1 mm long explants are placed into culture with Dulbecco's Modified Eagle's Medium (DMEM-Gibco, USA). Outgrowth of migratory cells are predominantly fibroblasts and the explants are moved to a new dish as these reach confluency. This is repeated over three to five passages until the cells that emerge are primarily Schwann cells. These are dissociated and grown up for seeding into copolymer or matrigel guidance channels (Schmidt, C. E. and Baier Leach, J., 2003, *Ann. Rev. Biomed. Eng.* 5: 293-347). Once implant material is prepared, cultured segments will have their ends recut to mimic scar excision, and placed end to end with implant material wedged between. Immediately after grafting, samples are re-treated with the Connexin43 antisense oligomers and the neuron behavior is monitored over subsequent days.

Measuring Outcomes

Time course experiments are carried out for both peripheral grafts and implants to establish whether there is immediate, late or continuous response to the graft tissues. Several markers are used to assess neuronal response and repair potential. These include: Neuronal (antibodies to Neuronal-N), neurofilament (antibodies to MAP-2 and SMI-31) and cytoplasmic markers (CMFDA) and membrane dyes (Di-I or Axon grease-Molecular Probes, Oregon, USA). Increased neural sprouting, increased axon migration distance (bridge length to distance migrated ratio) and increased numbers of axons growing toward or across the graft are specifically monitored. Cell specific markers (GFAP for astrocytes, Isolectin-B4 for microglial cells, and S-100 for Schwann cells). Glial cell distribution and density, and levels of myelination are assessed. Anti-CGRP (a peripheral nerve marker) are used to distinguish between axons of peripheral nerve origin as opposed to those regenerating from the cord segments. GAP-43 (growth associated protein) antibodies are used to identify neuronal growth cones. Toluidine blue stained semithin sections and electron microscopy of graft cross sections are used for morphological analysis.

Secondary antibodies are conjugated with Alexa dye. For double or triple labeling, we use Zenon probes (Molecular Probes, Oregon, USA) where appropriate. All antibody and dye labels are analysed using The University of Auckland's Biomedical Imaging Research Unit Leica TCS 4D and SP2 confocal laser scanning microscopes. Electron microscopy is performed on a Hitachi H-7000 electron microscope. Image analysis programmes (AnalySIS or NIH Image J) are used to quantify differences between control and treated grafts.

Example 7—Antisense Oligodeoxynucleotide Design

Materials

Materials used herein include art-recognized antibodies and plasmids; such as, for example, plasmids for rat connexin 43 (T7291,) and connexin 26; plasmids for mouse connexin 43 and connexin 26 (Invivogen, USA), mouse anti rat connexin 43 and rabbit anti rat connexin 26 from Zymed (51-2800); and goat anti mouse Alexa 488 and goat anti rabbit Alexa 568 secondary antibodies from Molecular Probes, Eugene Oreg. Nuclei were stained using Hoechst 33258 dye (Sigma). All deoxyribozymes and oligodeoxynucleotides were purchased from Sigma Genosys, Australia, as desalted oligomers. TaqMan labelled oligomers were purchased from Applied Biosystems, USA. All oligodeoxynucleotides were purchased as unmodified phosphodiester oligodeoxynucleotides.

Deoxyribozyme Design

The deoxyribozyme design and testing was similar to that described in previous studies (Santoro, S. W. and Joyce, G. F. *Proc. Natl Acad. Sci. USA*, (1997), 94, 4262-4266 and Cairns, M. J. et al., (1999) Nat. Biotech 17, 480-486). In brief, all AU and GU sites in the mRNA sequence of the target connexin were selected with 8 or 9 nucleotides on each side of the A or G. The deoxyribozymes are the complement of this sense coding sequence with the "A" or "G" replaced with the "10-23" catalytic core "ggctagctacaacga". Control deoxyribozymes had a defective catalytic core of "ggctaActacaacga" with a single point mutation (g→A) Santoro, S. W. and Joyce, G. F. Biochem 37, 13330-13342). We also designed GC and AC specific deoxyribozymes to cover gaps left by AU and GU deoxyribozymes not meeting the three requirements below. Each deoxyribozyme was named according to the position of "A" or "G" nucleotides from the start ATG codon. Those deoxyribozymes selected for in vitro assay had to fulfill three requirements:

1. Thermo stability: the chosen deoxyribozymes should not form stable secondary structures, either hairpin looping or homodimers. Any deoxyribozyme with a hairpin or homodimer melting temperature greater than 37° C. was discarded as presumptively unable to bind to the target sequence at physiological temperatures.

2. Affinity: The total AG values of both binding arms should not be greater than −30 Kcal. Each individual binding arm is between −10 to −15 kcal. This is a compromise between the specificity of binding/miss priming (due to higher CG content) and an effective binding/turnover rate requirement for deoxyribozymes. The binding arm length either side of the cleavage site is adjusted to find the ideal AG value and step (1) repeated to check.

3. Specificity: All target binding sequences were BLASTn searched with Gene Bank to check for specificity (http://www.ncbi.nlm.nih.gov/BLAST/). Deoxyribozymes with homology to other connexin genes or other known rodent genes were discarded.

In Vitro Testing of Deoxyribozymes

The mouse connexin43 and connexin26 cDNAs were excised from the pORF vector (Invivogen) with NcoI and NheI and subcloned into pGEM-T (Promega) prior to in vitro transcription. Both the full-length 2.4 kb rat connexin43 cDNA and the full coding 1.4 kb rat connexin43 cDNA including 200 nucleotides of 5'-untranslated regions were used for in vitro transcription. Full length mRNA was transcribed from linearized plasmid DNA using a Promega Riboprobe Kit. The resulting mRNA was purified with a PCR spin column (Qiagen). Concentration was determined by spectrophotometer reading of OD at 260 nm. Deoxyribozymes (40 µM final concentration) and mRNA (0.01 to 0.05 µg/µl total mRNA) were then separately pre-equilibrated with a 2× cleavage buffer (100 mM Tris 7.5; 20 mM $MgCl_2$; 300 mM NaCl; 0.02% SDS) for 5-10 minutes at 37° C. mRNA and deoxyribozyme mix were then incubated for one hour at 37° C., following which, 10× Bluejuice (Invitrogen) was added to stop the cleavage reaction and the mixture kept on ice. The reaction mixture was then loaded onto a pre-run 4% polyacrylamide gel (19:1 acryl: bis ratio, BioRad) in 1×TBE buffer and 7M Urea and run for up to 2 hours. Gels were stained with a 1:10 000 dilution of SYBR green II (Mol Probes, USA) in TBE buffer and imaged using a BioRad Chemi Doc system.

Design of Antisense Oligomers

Antisense sequences were chosen based on the twenty-nucleotide sequences of the deoxyribozyme binding arms that were successful in cleaving the mRNA in vitro. Selected sequences were chosen for use in the design of 30-mer oligos (Brysch, W. (1999). Antisense Technology in the Ventral Nervous System, ed. H. A. Robertson; Oxford University Press 21-41) and (Walton S., et al., (2002) Biophysical Journal 82, 366-377). In brief, sequence related side effects such as partial sequence homology of 8-10 CG base pairings to unrelated genes, GGGG and CpG motifs were avoided. Antisense sequences with the 3'-end ending with a Thymidine or more than three C or Gs in the last five nucleotides are also avoided if possible to prevent miss priming. Oligomers that form stable secondary structures such as homodimers, palindrome motifs or secondary hairpin structures will impede oligomers binding to the target mRNA. Control oligomers, including sense, scrambled, reverse and mismatch oligomers were also designed to assess possible chemistry related side effects due to cross hybridization, non specific protein binding, and toxicity.

Corneal Organ Culture and Treatment with Antisense Oligonucleotides 30-34 day old Wistar rats were euthanized with carbon dioxide and whole rat eyes dissected. The ocular surface was dissected, disinfected with 0.1 mg/ml penicillin-streptomycin for 5 minutes and rinsed in sterile PBS. The whole eye was then transferred onto a sterile holder in a 60 mm culture dish with the cornea facing up. The eyes were mounted with the corneal epithelium exposed at the air-medium interface and cultured at 34° C. in a humidified 5% $CO_2$ incubator in serum free medium (Opti-MEM, Invitrogen) for up to 48 hours. 100 µl of medium was added drop wise to the surface every eight to twelve hours to moisten the epithelium. Medium levels were maintained to the level of the limbal conjunctiva.

Antisense oligomers were mixed with 30% (w/w) Pluronic F127 gel (Sigma) on ice to a final 2 µM concentration and 10 µl applied onto the corneas as previously described. (See Becker, D. L., et al.; (1999b) *Dev. Genet.* 24:33-42; Green, C. R., et al.; (2001), Methods Mol Biol 154, 175-185). Each treatment had a sample size of 3 to 4 corneas per experiment. Preliminary experiments showed that double treatments of our positive control, DB1, for 8 hours had little effect on connexin43 protein expression in our corneal culture. Corneas were therefore cultured for 24 hours and connexin43 specific oligomers applied every 8 hours. However, we found that endogenous connexin26 expression is affected if the culture was maintained for 24 hours. Hence, we reduced the culture period for connexin26 specific oligomers treated corneas to 12 hours, with application of antisense oligomers every 4 hours. Medium was changed ten minutes prior to every repeat application of antisense or control oligomers. At defined times, corneas were rinsed with PBS, immersed in OCT (Tissue Tek, Japan) and snap-frozen in liquid nitrogen. 25 µm cryosections were subsequently cut with a Leica cryostat (CM3050s) and mounted on SuperFrost Plus slides (Menzel, Germany). For both Cx43 and Cx26 mRNA analysis corneas were collected 8 hours after a single antisense treatment.

RNA Isolation and Real-Time PCR

Total RNA was extracted from isolated rat corneas using TRIzol reagent (GIBCO, Invitrogen, USA) according to the manufacturer's protocols. The quality of RNA samples was assessed by electrophoresis through ethidium bromide stained agarose gels and the 18S and 28S rRNA bands visualized under UV illumination. The extraction yield was quantified spectrophotometrically at 260 nm. For real-time PCR, cDNA was prepared from 5 ug of total RNA by using oligo dT and superscript II Rnase H-reverse transcriptase (Life Technologies, Invitrogen, USA) in a final reaction volume of 20 μl. Quantitative PCR reaction was carried out in 96-well optical reaction plates using a cDNA equivalent of 100 ng total RNA for each sample in a volume of 50 μl using the TaqMan Universal PCR Master Mix (Applied Biosystems, USA) according to the manufacturer's instructions. PCR was developed on the ABI PRISM 7700 Sequence Detection system instrument (Applied Biosystems, USA). The thermal cycling conditions comprised an initial denaturation step at 95° C. for 10 minutes and 50 cycles of two-step PCR, including 15 seconds of denaturation at 95° C. and 1 minute of annealing-elongation at 60° C., using the standard protocol of the manufacturer. All experiments were repeated in triplicate. The monitoring of negative control for each target showed an absence of carryover.

Amplification of 18S rRNA was performed as an internal reference against which other RNA values can be normalized. If the efficiencies of the target and 18S rRNA amplifications were approximately equal, then the formula $2^{-\Delta\Delta Ct}$ was used to calculate relative levels of mRNA without the need for a standard curve. If the efficiency of amplification of the target and 18SrRNA were significantly different, a relative standard curve method was used to calculate absolute quantities of mRNA and 18S rRNA for each experiment from the measured Ct, and then the relative mRNA levels of the target gene compared with control quantified after normalization to 18S rRNA.

All calculations were performed by using PRISM 3.02 software (GraphPad, San Diego). Statistical difference between groups was determined by using the Student's t test. Comparisons among several groups were performed by ANOVA, and significance was calculated by using Dunnett's multiple comparison test.

Assessment of Antisense Oligomers Efficiency on Blocking Translation

Cy3 and TaqMan (Fam, Tamra) labelled oligomers were used to assess penetration and stability. Cy3-labelled oligomers (Sigma Genosys) and TaqMan (FAM, TAMRA) labeled oligomers (Applied Biosystems) were applied with Pluronic gel to measure both the stability and the penetration of oligomers into the corneal epithelium. The treated corneas were fixed in 4% paraformaldehyde for 20 minutes, mounted in 1% agar and viewed under a 40× water immersion lens as whole mount. The depth of oligomer penetration was measured using the Z-scan option on a Leica SP2 confocal microscope and plots of intensity versus z-distance measured. The breakdown of TaqMan oligomers was measured using the Lamdba scan option on the confocal. Fluorescence resonance energy transfer (or FRET) between the FAM (donor) and TAMRA (receptor) molecule occurs in intact 30mer oligomers. When the oligomer is broken down FAM and TAMRA are no longer in close proximity and FRET no longer occurs.

Immunofluorescent Labelling

Immunolabelling of connexins on corneal sections were performed as previously described. In brief, sections were blocked in 10% goat serum and incubated with primary antibody at 1:250 (mouse anti rat connexin43) or 1:500 (rabbit anti rat connexin26) at 4° C. overnight. The sections were then washed with PBS, incubated with 1:400 dilution of Alexa 488 labeled secondary antibody at room temperature for 2 hours and then fixed in 4% paraformaldehyde and counterstained with 0.2 μM Propidium Iodide or a 1:50 dilution of Hoechst 33258 for 10 min. Sections were mounted in Citifluor antifade medium (Agarscientific UK). All images were collected using either a Leica TCS-4D or Leica SP2 confocal laser scanning microscope and stored as TIF files. All images were collected using consistent voltage (520-540 V) and offset (−2) settings. The voltage and offset were set using the glow-over-under display option to maximize the gray scale for images of control tissue. The same settings were then used for all samples within the same experiment.

For quantification, four optical slices through three micrometers were processed into a single extended focus optical image by using the center of mass topographic projection option on the TCS-4D. Spots of connexin label were counted using NIH image (Scion Corp.) after thresholding at 90 to 100 pixel intensity on the 256 grey scale image. The area of corneal epithelium was also measured and a connexin density per unit area was calculated. An average of four extended focus images were used to calculate the absolute connexin density of each cornea. This number was then normalized with the medium connexin density of either sense control treated or gel treated corneas. We have represented the data as percentage knock down when comparing different treatments.

Deoxyribozymes Selectively Cleave mRNA In Vitro

Figure 11:
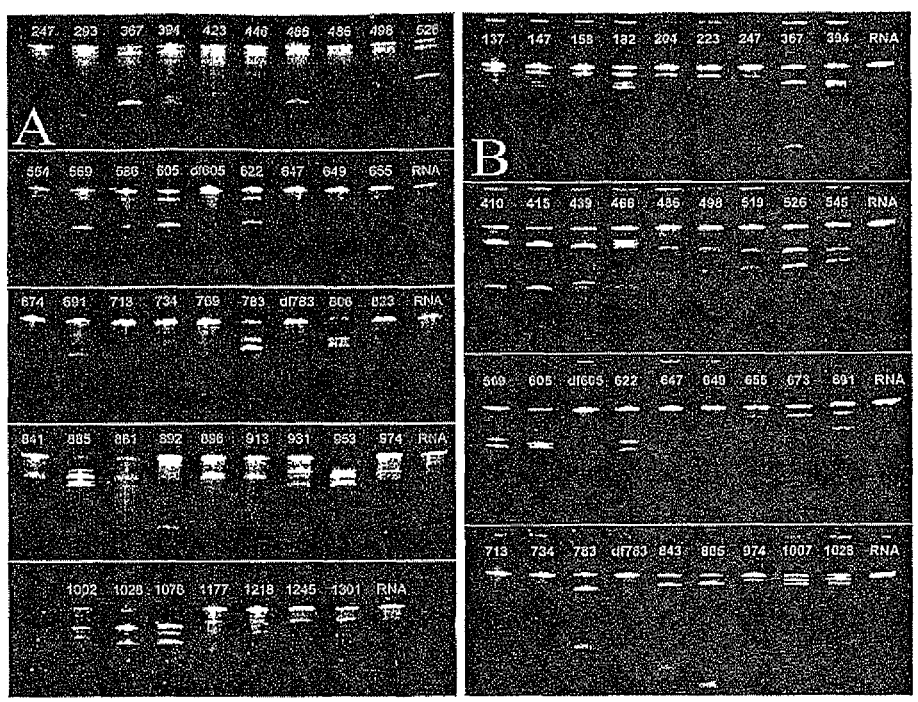
FIG. 11 illustrates that deoxyribozymes selectively cleave specific regions of target connexin-43 mRNA in vitro. A 2.4 kb rat connexin-43 mRNA (11A) and 1.2 kb mouse connexin-43 mRNA (11B) were transcribed in vitro from plasmid and incubated with various deoxyribozymes for 1 hour. Region 896-953 of rat mRNA (11A) was inconclusive because no deoxyribozymes were designed for corresponding region in mouse. Deoxyribozymes cleavage of region 367-466 in mouse mRNA (11B), does not match results from rat connexin-43 mRNA, probably due to the presence of 200 base pair of 5' untranslated region in rat mRNA. Defective control deoxyribozymes with single point mutation, df605 and df783, showed that such cleavages were specific. Some non-specific miss priming by deoxyribozymes against mouse mRNA were also observed by mouse dz1007 and dz1028. Overall, deoxyribozymes targeting the 526-622, 783-885, and 1007-1076 base regions showed significantly cleavage in both rat and mouse mRNA species.

Sixty six deoxyribozymes were designed specifically against rodent connexin43 mRNA (Table 5). Twenty two of these deoxyribozymes were designed to recognize both mouse and rat connexin43 mRNA. We also purchased two defective deoxyribozymes with a single point mutation in the "10-23" catalytic core as negative controls. The deoxyribozyme cleavage results were similar for the rat connexin43 mRNA 1.1 Kb in length (not shown) and the rat connexin43 mRNA 2.4 Kb in length (FIG. 11A). Both rat (FIG. 11A) and mouse (FIG. 11B) connexin43 mRNA appear to have similar regions accessible to the deoxyribozymes. The results indicate four regions on the rodent connexin43 mRNA that are exposed and available for deoxyribozyme cleavage. These regions are around 367-466, 526-622, 783-885, and 1007-1076 bases from the start ATG codon. The two defective deoxyribozymes, a1df605 and a1df783, showed no cleavage of rodent connexin43 mRNA. Deoxyribozymes designed against the 200 base pair 5' untranslated region of rat connexin43 mRNA also did not show any cleavage activity.

TABLE 5

Summary of deoxyribozyme (dz) and antisense (as) oligodeoxynucleotide sequences showing various degrees of in vitro and in vivo activity against rat connexin43.

| | Name | ODN Sequence 5' to 3' | in vitro | in vivo protein | In vivo mRNA |
|---|---|---|---|---|---|
| SEQ ID NO: 32 | r43dz14 | CCAAGGCA ggctagctacaacga TCCAGTCA | − | | |
| SEQ ID NO: 33 | a1dz605 | CCGTGGGA ggctagctacaacga GTGAGAGG | + | | |

TABLE 5-continued

Summary of deoxyribozyme (dz) and
antisense (as) oligodeoxynucleotide sequences
showing various degrees of in vitro and in
vivo activity against rat connexin43.

| | Name | ODN Sequence 5' to 3' | in vitro | in vivo protein | In vivo mRNA |
|---|---|---|---|---|---|
| SEQ ID NO: 34 | a1df605 | CCGTGGGA ggctaActacaacga GTGAGAGG | - | | |
| SEQ ID NO: 35 | r43dz769 | AGTCTTTTG ggctagctacaacga TGGGCTCA | - | | |
| SEQ ID NO: 36 | a1dz783 | TTTGGAGA ggctagctacaacga CCGCAGTC | ++ | | |
| SEQ ID NO: 37 | a1df783 | TTTGGAGA ggctaActacaacga CCGCAGTC | - | | |
| SEQ ID NO: 38 | r43dz885DB1 | ACGAGGAA ggctagctacaacga TGTTTCTG | +++ | | |
| SEQ ID NO: 39 | r43dz892 | TTGCGGC ggctagctacaacga CGAGGAAT | - | | |
| SEQ ID NO: 40 | r43dz953 | CCATGCGA ggctagctacaacga TTTGCTCT | +++ | | |
| SEQ ID NO: 41 | r43dz1076 | TTGGTCCA ggctagctacaacga GATGGCTA | +++ | | |
| SEQ ID NO: 42 | DB1 | GTA ATT GCG GCA GGA GGA ATT GTT TCT GTC | | + | ++ |
| SEQ ID NO: 43 | DB1s | GACAGAAACAATTCCTCCTGCCGCAATTAC | | - | - |
| SEQ ID NO: 44 | r43as14 | CCAAGGCACTCCAGTCAC | | - | |
| SEQ ID NO: 45 | a1as605 | TCCGTGGGACGTGAGAGGA | | ++ | ++ |
| SEQ ID NO: 46 | r43as769 | AGTCTTTTGATGGGCTCA | | up | up |
| SEQ ID NO: 47 | a1as783 | TTTTGGAGATCCGCAGTCT | | + | ++ |
| SEQ ID NO: 48 | r43as885 | CACGAGGAATTGTTTCTGT | | + | |
| SEQ ID NO: 49 | r43as892 | TTTGCGGCACGAGGAATT | | - | |
| SEQ ID NO: 50 | a1as953 | CCCATGCGATTTGCTCTG | | + | |
| SEQ ID NO: 51 | a1as1076 | GTTGGTCCACGATGGCTAA | | + | |

Table 5 shows those ribozyme and antisense sequences selected on the basis of in vitro ribozyme cleavage studies for in vivo analysis (mRNA and/or protein levels) or where defective ribozyme controls (SEQ ID NO:56 and SEQ ID NO:59) are compared with normal ribozymes.

Figure 15:
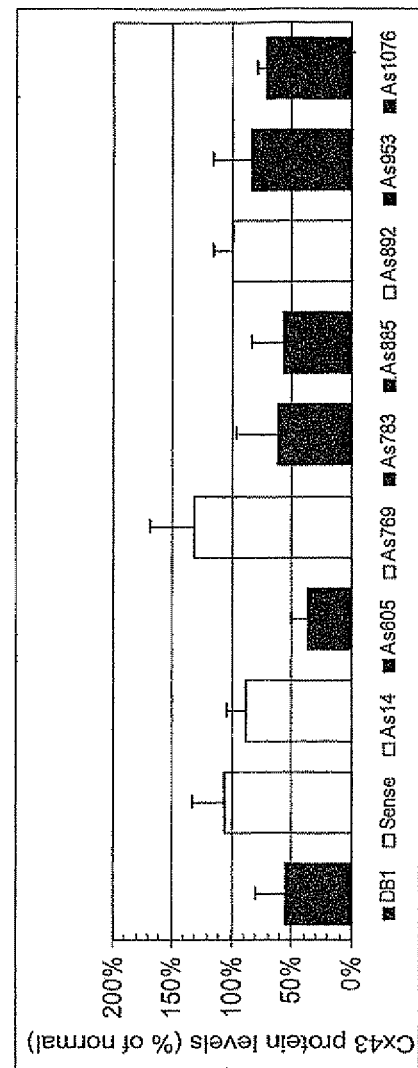
FIG. 15 shows that connexin43 antisense oligomers selectively reduce connexin-43 proteins expression in rat corneas. Each spot represents a single cornea with different treatments. The solid spot (black colored, DB1, as605, as783, as885, as953 and as1076) showed an average of 36% to 85% reduction in connexin-43 expression when compared to white coloured spots (DB1 sense, as14, as769 and as892). All antisense oligomers predicted by deoxyribozyme tertiary prediction assay to have little or no effect, showed an average of 85% to 134% of normal connexin-43 expression. All experiments were normalised with the medium connexin-43 density treated with DB1 sense and as a result two negative oligomers (as769 and as892) showed greater connexin-43 density than DB1 sense control treatment.

The oligomer names have the prefix r43 where they are specific only to rat connexin43 only; the prefix a1 denotes specificity against both mouse and rat. All oligomer sequences are unmodified phosphodiester oligodeoxynucleotides. "ggctagctacaacga" represents the "10-23" catalytic core of the deoxyribozymes and "ggctaActacaacga" is the defective mutant control. DB1 is a 30-mer version of as885 (marked in lower case) and DB1s is the sense control of DB1 sequence. In vitro effects were measured as percentage mRNA cleavage by individual deoxyribozymes. In vivo effects were measured by immunolabeling of connexin43 in corneal sections (refer to FIG. 15) or Real-Time PCR assessment of surviving mRNA levels (refer to FIG. 16). +++ means >75%, ++ means between 50% to 75%, + means between 25% to 50%, and - means between 0% to 25% in vitro cleavage of mRNA or in vivo reduction of protein and mRNA expressions. up means an increase in connexin43 protein expression when compared to DB1 sense or gel only control treatment.

Figure 12:
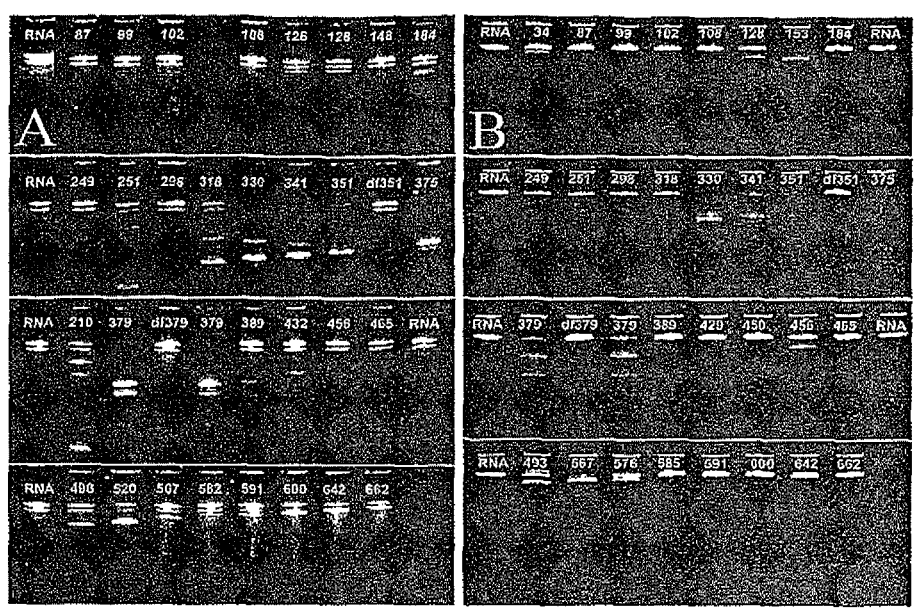
FIG. 12 illustrates that deoxyribozymes selectively cleave specific regions of target connexin-26 mRNA in vitro. A 0.7 kb rat (12A) and mouse (12B) connexin-43 mRNA was transcribed in vitro from plasmid and incubated with various deoxyribozymes for 1 hour. The cleavage results show that rodent connexin26 mRNA has at least two regions that are targeted by deoxyribozymes, in the 318-379 and 493-567 base regions. Defective control deoxyribozymes with single point mutation, df351 and df379, showed that such cleavages were specific.

We also tested forty four deoxyribozymes designed specifically against rodent connexin26 mRNA (Table 6), of which 17 deoxyribozymes match both mouse and rat connexin26 mRNA. The rat connexin26 mRNA appeared as a double band on the gel owing to the presence of two T7 RNA polymerase promotors on the cloning plasmid. The cleavage results show that connexin26 mRNA has at least two regions accessible to deoxyribozymes, in the 318-379 and 493-567 base regions (FIG. 12A, 12B). These figures show that most consistently cleaving deoxyribozyme is the cx26dz330, which cleaves both species of mRNA within one hour. The two defective deoxyribozymes (b2df351 and b2df379) showed no cleavage of rodent connexin26 mRNA. The deoxyribozymes cx26dz341, dz351, dz375, dz379 consistently cleave rat connexin26 mRNA at a higher rate compared to mouse connexin26 mRNA. On the other hand, mcx26dz153 and dz567 appear to be superior connexin26 deoxyribozymes in mouse when compared to rat.

The rat cornea organ culture was therefore selected as the model system to test the effectiveness of the antisense oligodeoxynucleotides designs derived from the in vitro model. We cultured rat corneas for 24 hours and found that the endothelium remains intact. However culture times longer than 48 hours appeared to affect the opacity of the corneas and were therefore not used. Cy3 labelled oligomers were used to determine the extent of penetration of the oligomer into the cultured cornea. Confocal optical slices down through the intact cornea show that fluorescent signal

TABLE 6

Deoxyribozyme (dz) and antisense (as) oligodeoxynucleotide sequences showing various degrees of in vitro and in vivo activity against rodent connexin26.

| | Name | ODN Sequence 5' to 3' | in vitro | in vivo protein | In vivo mRNA |
|---|---|---|---|---|---|
| SEQ ID NO: 52 | m26dz153 | GTTGCAGA ggctagctacaacga AAAATCGG | +++ | | |
| SEQ ID NO: 53 | b2dz330 | GTTCTTTA ggctagctacaacga CTCTCCCT | +++ | | |
| SEQ ID NO: 54 | b2dz341 | GTCCTTAAA ggctagctacaacga TCGTTCTTT | +++ | | |
| SEQ ID NO: 55 | b2dz351 | TCTCTTCGA ggctagctacaacga GTCCTTAAA | +++ | | |
| SEQ ID NO: 56 | b2df351 | TCTCTTCGA ggctaActacaacga GTCCTTAAA | - | | |
| SEQ ID NO: 57 | b2dz375 | GATACGGA ggctagctacaacga CTTCTGGG | +++ | | |
| SEQ ID NO: 58 | b2dz379 | CTTCGATA ggctagctacaacga GGACCTTC | +++ | | |
| SEQ ID NO: 59 | b2df379 | CTTCGATA ggctaActacaacga GGACCTTC | - | | |
| SEQ ID NO: 60 | m26dz567 | GGTGAAGA ggctagctacaacga AGTCTTTTCT | +++ | | |
| SEQ ID NO: 61 | b2as330n | CCTTAAACTCGTTCTTTATCTCTCCCTTCA | | - | ++ |
| SEQ ID NO: 62 | b2rv330n | ACTTCCCTCTCTATTTCTTGCTCAAATTCC | | - | - |
| SEQ ID NO: 63 | r26as375n | TACGGACCTTCTGGGTTTTGATCTCTTCGA | | - | + |
| SEQ ID NO: 64 | r26rv375n | AGCTTCTCTAGTTTTGGGTCTTCCAGGCAT | | - | |

Table 6 shows those ribozyme and antisense sequences that consistently cleaved the mRNA in vitro, were selected on the basis of in vitro ribozyme cleavage studies for in vivo analysis (mRNA and/or protein levels), or where used as defective ribozyme controls. The oligomer names have the prefix m26 or r26 where they are specific only to mouse or rat connexin26 mRNA respectively, and the prefix b2 denotes specificity against both species. All oligomer sequences are unmodified phosphodiester oligodeoxynucleotides. "ggctagctacaacga" represents the "10-23" catalytic core of the deoxyribozymes and "ggctaActacaacga" is the defective mutant control. A reverse control (rv) was also used to control for any non-specific effects of antisense oligomers. In vivo effects were measured by immunolabeling of connexin26 in corneal sections and Real-Time PCR of the target mRNA expression (refer to FIG. 17). +++ means >75%, ++ means between 50% to 75%, + means between 25% to 50%, and - means between 0% to 25% in vitro cleavage of mRNA or in vivo reduction of protein and mRNA expressions.

Fluorescently Labeled ODN in Pluronic Gel can Penetrate the Corneal Epithelium

Figure 13:
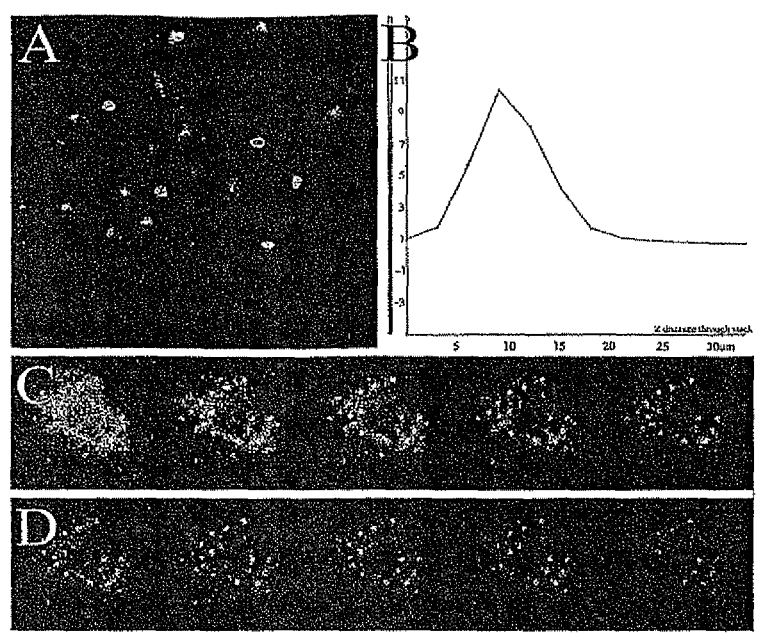
FIG. 13 shows antisense oligomer penetration and stability in cultured corneas for up to one hour. Cy3 labelled oligomers show punctate nuclear and cytoplasmic labelling one hour after delivery with Pluronic gel (13A). The rate of visible Cy3 penetration was 10-15 µm after one hour in corneal epithelium (13B). Taqman labelled oligomer probes was used to measure the stability of antisense oligomers inside epithelial cells using Lambda scan with each panel showing a 5 nm light emission spectrum towards the red colour (13B). Intact Taqman probe shows Fluorescence Resonance Energy Transfer with the red fluorescence light of TAMRA represented on gray-scale (13D) while breakdown products are represented as green fluorescence as expected from FAM (also shown on gray-scale (13C)). The effective antisense oligomer concentration in cells could be lower than that can be detected by fluorescence technique.

Rat corneas maintain expression of both connexin43 and connexin26 in organ culture and are easily accessible to the delivery of antisense oligomers by 30% Pluronic F-127 gel. is present with CY3 labeled oligomers at FIG. 13A shows fluorescent signal 10 µm deep in the cultured cornea 1 hour after initial treatment. TaqMan probes conjugated to oligodeoxynucleotides were used to measure and demonstrate the delivery of intact oligodeoxynucleotide with 30% Pluronic gel into corneal epithelium. A significant proportion of oligomer remained intact one hour after treatment (FIG. 13B, 13C). The punctuate signal of intact oligomers (FRET occurring in FIG. 13C) can be seen as the red (represented on gray-scale) wavelength while signal from degraded oligomers (no FRET) appears in the green (represented on gray-scale) emission spectrum (FIG. 13B).

Deoxyribozyme Assay Predicts ODNs that can Knockdown Connexin43 Protein in Corneal Epithelium.

Figure 14:
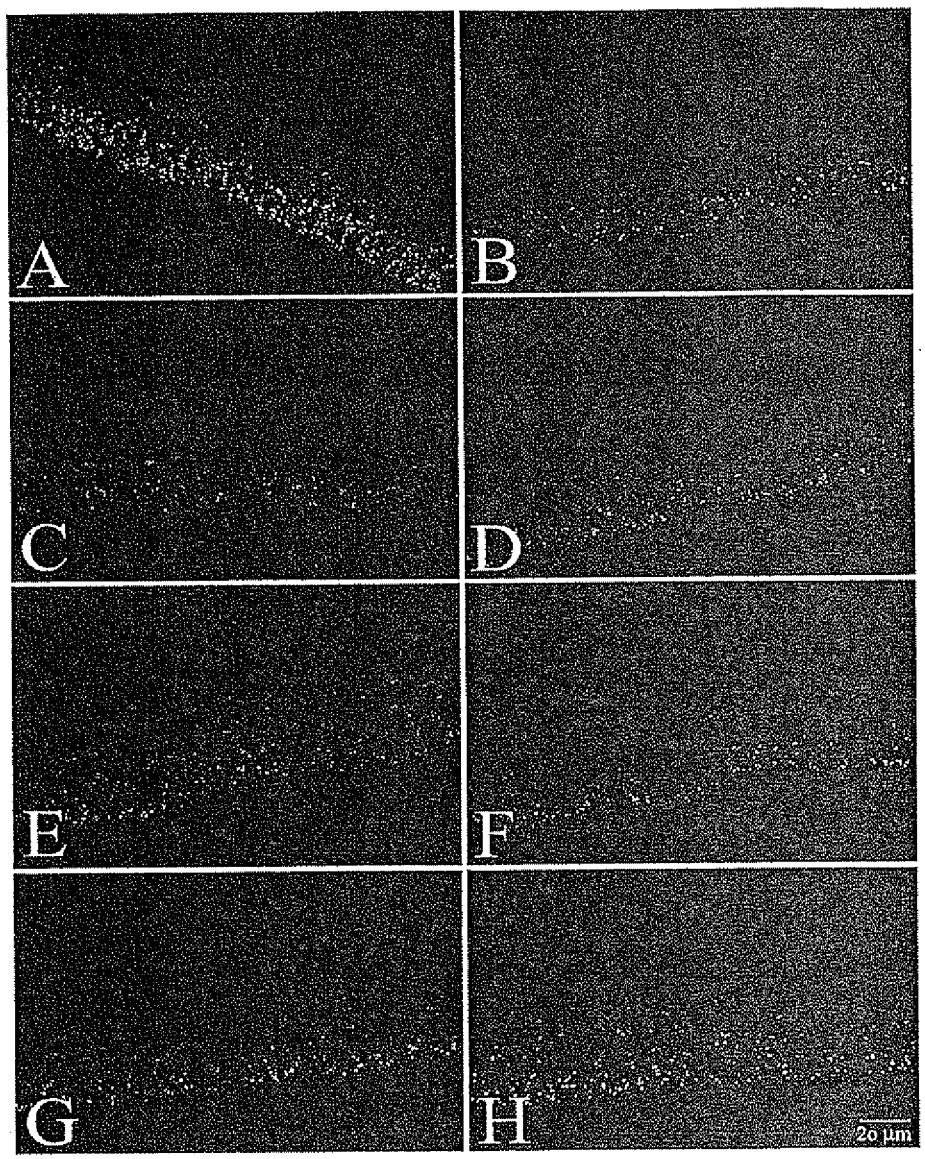
FIG. 14 illustrates the effects of different antisense oligomers on connexin-43 (light, gray-scale) and connexin-26 (dark, gray-scale) protein expression were shown by in vitro deoxyribozyme mRNA cleavage.

In a preliminary experiment, we treated rat corneas with a single application of our positive control, DB1, and found no significant changes in connexin43 protein expression after 8 hours. Clear protein knockdown at 24 hours was seen after three applications at eight hourly intervals. Based in part on results from the deoxyribozyme cleavage assay we tested certain antisense oligomers in vivo (DB1, r43as605, r43as783, r43as885, r43as953 and r43as1076), as well as antisense oligomers that were predicted to be non-functional (r43as14, r43as769 and r43as892), and a negative control (DB1 sense). We found knockdown of connexin43 protein levels after 24 hours of treatment compared to controls (FIG. 14A) with all of the antisense oligomers that we had determined should be positive (FIG. 14C, 14E, 14G). All three of those predicted to be negative, and the negative control oligomer, did not affect connexin43 expression (FIG. 14B, 14D, 4F, 4H). DB1, a 30-mer version of as885, showed a similar percentage knock down to the shorter as885 (just under 50% knockdown). One of the better antisense oligomers identified in this experiment appeared to be as605 with a 64% reduction in protein level. A summary of these results quantified is presented in FIG. 15.

To test the technique for other connexins, further oligodeoxynucleotides were designed and tested for connexin26. Two 30-mer antisense oligodeoxynucleotides designated as r26as330N and 375N, together with their appropriate reverse control oligodeoxynucleotides were designed against connexin26 based on regions within the cleavage areas of b2dz330 and b2dz375. We found that these antisense oligodeoxynucleotides (as330N and as375N) did not, however, lead to a significant difference in protein expression levels within the 12 hour time period for these experiments when antisense oligomers treated cultures were compared with the reverse control treated corneas.

Antisense ODNS Lead to Reduction in Connexin43 and Connexin 26 mRNA

Figure 16:
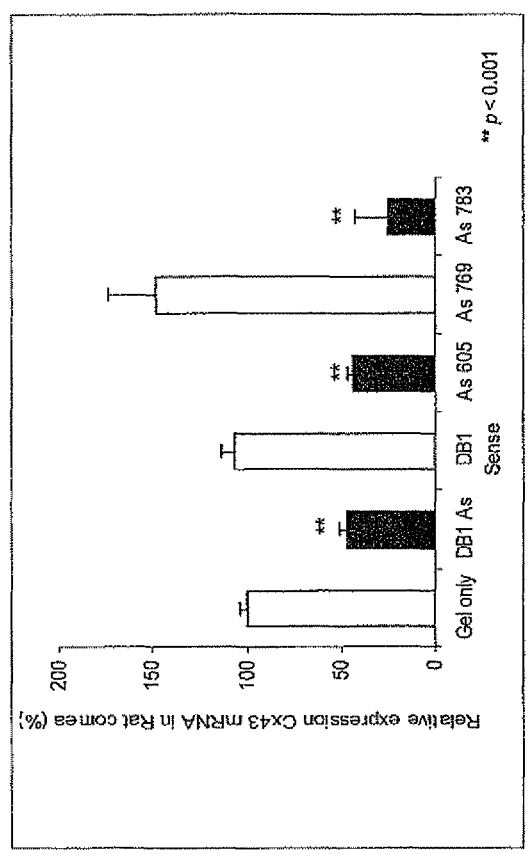
FIG. 16 illustrates a comparison of connexin43 mRNA levels in rat cornea treated with antisense or sense oligomers assessed using Real-Time PCR. The level is expressed as a percentage of Pluronic gel only treated cornea. Three antisense ligodexoynucleotides predicted by in vitro assay to be functional, DB1As, As605 and As783 (black bars), reduced connexin43 mRNA expression to 46.8%, 44% and 25% of normal (gel only open bar) levels respectively (** $p<0.001$). No reduction was seen for the DB1 sense control oligomer (106%) (open bar DB1 sense). As769, which did not show any cleavage of Cx43 cRNA in the in vitro deoxyribozyme tertiary prediction assay, served as a negative control (148%) (open bar As769).

Real time PCR was used to determine the effect of antisense oligodeoxynucleotides on mRNA levels. It confirmed that antisense oligodeoxynucleotides that knock down connexin43 protein expression (as605, as885, DB1) also have lower connexin43 mRNA levels compared to control corneas within 8 hours after treatment (FIG. 16). The percentage reduction in relative levels of connexin43 mRNA correlated well with the level of reduction of connexin43 protein. The negative antisense oligomer (as769) and negative controls (DB1 sense, gel only) exhibited unchanged levels of connexin43 mRNA compared to control corneas.

Figure 17:
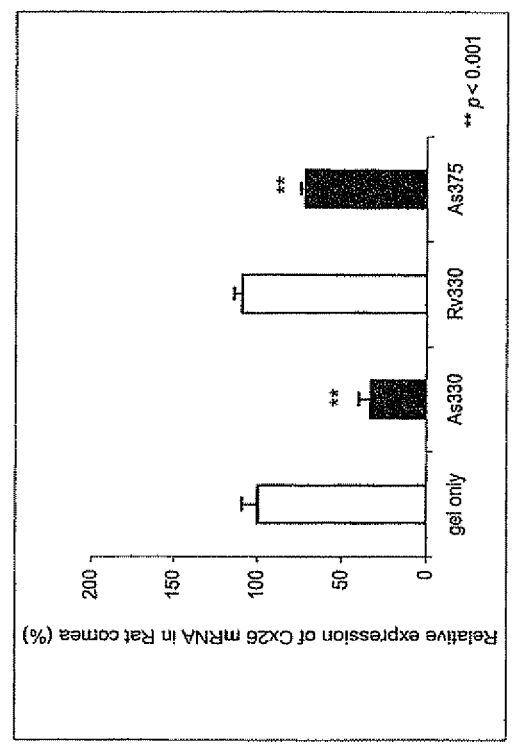
FIG. 17 illustrates a comparison of connexin26 mRNA levels in rat cornea treated with antisense or sense (control) oligomers and assessed using Real-Time PCR. The level is expressed as percentage of pluronic gel only treated cornea (gel only open bar). As330 and As375 reduced Cx26 mRNA expression to 33% and 71% respectively (** $p<0.001$) (black bars). No reduction was seen for Rv330 sense oligomer (109%) (Rv330 open bar).

Connexin26 mRNA expression was also significantly reduced by as330N and as375N within 8 hours of antisense treatment (FIG. 17). The reverse sequence control for as330N and a gel only control exhibited no effect on mRNA levels.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method for treating a subject for corneal trauma, comprising topically administering to the eye of said subject a composition comprising a pluronic F127 gel, a buffer, and a connexin 43-downregulating amount of a connexin 43 antisense compound, wherein said connexin 43 antisense compound is 5' GTA ATT GCG GCA AGA AGA ATT GTT TCT GTC 3' (SEQ ID NO: 1).

2. The method of claim 1, wherein said trauma is a penetrating eye trauma.

3. A method of claim 2 wherein the eye trauma is chemical trauma.

4. A method of claim 2 wherein the eye trauma is mechanical trauma.

5. A method of claim 1 wherein the eye trauma results in corneal epithelial damage.

6. A method of claim 1 wherein the connexin 43 antisense compound is administered to a subject having an amniotic membrane graft.

7. A method of claim 1 wherein said composition comprises 30% (w/w) pluronic F127 gel in a buffer.

8. A method of claim 1 wherein the pluronic gel comprises up to 15% pluronic F127, up to 20% pluronic F127, up to 25% pluronic F127 or up to 30% pluronic F127 in a buffer.

9. A method of claim 1 wherein the composition further comprises a preservative.

10. A method of claim 1 wherein the composition is administered once.

11. A method of claim 1 wherein the composition is administered more than once.

12. A method of claim 1 wherein the subject is a human.

13. The method of claim 1, wherein the composition administered is in an amount from 0.001 to 100 mg/kg per day.

14. The method of claim 1, wherein the composition administered is in an amount from 0.01 to 100 mg/kg per day.

15. The method of claim 1, wherein the composition administered is in an amount from 1 to 40 mg/kg per day.

16. The method of any of claim 1, or 13-15, wherein the composition is administered in single or divided dosages.

* * * * *

SEQUENCE LISTING

<160> NUMBER OF SEQ ID NOS: 67

<210> SEQ ID NO 1
<211> LENGTH: 30
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 1
gtaattgcgg caagaagaat tgtttctgtc                                       30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtaattgcgg caggaggaat tgtttctgtc                                       30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggcaagagac accaaagaca ctaccagcat                                       30

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcctgagcaa tacctaacga acaaata                                          27

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
catctccttg gtgctcaacc                                                  20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ctgaagtcga cttggcttgg                                                  20

<210> SEQ ID NO 7
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 7
ctcagatagt ggccagaatg c                                              21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttgtccaggt gactccaagg                                                20

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cgtccgagcc cagaaagatg aggtc                                          25

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
agaggcgcac gtgagacac                                                 19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgaagacaat gaagatgtt                                                 19

<210> SEQ ID NO 12
<211> LENGTH: 3088
<212> TYPE: DNA
<213> ORGANISM: Homo sapiens

<400> SEQUENCE: 12
acaaaaaagc ttttacgagg tatcagcact tttctttcat taggggaag gcgtgaggaa      60 agtaccaaac agcagcggag ttttaaactt taaatagaca ggtctgagtg cctgaacttg    120 cctttcatt ttacttcatc ctccaaggag ttcaatcact ggcgtgact tcactacttt     180 taagcaaaag agtggtgccc aggcaacatg ggtgactgga gcgccttagg caaactcctt    240
gacaaggttc aagcctactc aactgctgga gggaaggtgt ggctgtcagt acttttcatt    300
ttccgaatcc tgctgctggg gacagcggtt gagtcagcct ggggagatga gcagtctgcc    360
```

| | |
|---|---|
| tttcgttgta acactcagca acctggttgt gaaaatgtct gctatgacaa gtctttccca | 420 |
| atctctcatg tgcgcttctg ggtcctgcag atcatatttg tgtctgtacc cacactcttg | 480 |
| tacctggctc atgtgttcta tgtgatgcga aaggaagaga aactgaacaa gaaagaggaa | 540 |
| gaactcaagg ttgcccaaac tgatggtgtc aatgtggaca tgcacttgaa gcagattgag | 600 |
| ataaagaagt tcaagtacgg tattgaagag catggtaagg tgaaaatgcg aggggggttg | 660 |
| ctgcgaacct acatcatcag tatcctcttc aagtctatct ttgaggtggc cttcttgctg | 720 |
| atccagtggt acatctatgg attcagcttg agtgctgttt acacttgcaa aagagatccc | 780 |
| tgcccacatc aggtggactg tttcctctct cgccccacgg agaaaaccat cttcatcatc | 840 |
| ttcatgctgg tggtgtcctt ggtgtccctg gccttgaata tcattgaact cttctatgtt | 900 |
| ttcttcaagg gcgttaagga tcgggttaag ggaaagagcg acccttacca tgcgaccagt | 960 |
| ggtgcgctga gccctgccaa agactgtggg tctcaaaaat atgcttattt caatggctgc | 1020 |
| tcctcaccaa ccgctcccct ctcgcctatg tctcctcctg ggtacaagct ggttactggc | 1080 |
| gacagaaaca attcttcttg ccgcaattac aacaagcaag caagtgagca aaactgggct | 1140 |
| aattacagtg cagaacaaaa tcgaatgggg caggcgggaa gcaccatctc taactcccat | 1200 |
| gcacagcctt ttgatttccc cgatgataac cagaattcta aaaaactagc tgctggacat | 1260 |
| gaattacagc cactagccat tgtggaccag cgaccttcaa gcagagccag cagtcgtgcc | 1320 |
| agcagcagac ctcggcctga tgacctggag atctagatac aggcttgaaa gcatcaagat | 1380 |
| tccactcaat tgtggagaag aaaaaaggtg ctgtagaaag tgcaccaggt gttaattttg | 1440 |
| atccggtgga ggtggtactc aacagcctta ttcatgaggc ttagaaaaca caagacatt | 1500 |
| agaataccta ggttcactgg gggtgtatgg ggtagatggg tggagaggga ggggataaga | 1560 |
| gaggtgcatg ttggtattta aagtagtgga ttcaaagaac ttagattata ataagagtt | 1620 |
| ccattaggtg atacatagat aagggctttt tctccccgca acacccccta gaatggttc | 1680 |
| tgtgtatgtg aatgagcggg tggtaattgt ggctaaatat ttttgtttta ccaagaaact | 1740 |
| gaaataattc tggccaggaa taaatacttc ctgaacatct taggtctttt caacaagaaa | 1800 |
| aagacagagg attgtcctta agtccctgct aaaacattcc attgttaaaa tttgcacttt | 1860 |
| gaaggtaagc tttctaggcc tgaccctcca ggtgtcaatg gacttgtgct actatatttt | 1920 |
| tttattcttg gtatcagttt aaaattcaga caaggcccac agaataagat tttccatgca | 1980 |
| tttgcaaata cgtatattct ttttccatcc acttgcacaa tatcattacc atcactttt | 2040 |
| catcattcct cagctactac tcacattcat ttaatggttt ctgtaaacat ttttaagaca | 2100 |
| gttgggatgt cacttaacat tttttttttt tgagctaaag tcagggaatc aagccatgct | 2160 |
| taatatttaa caatcactta tatgtgtgtc gaagagtttg ttttgtttgt catgtattgg | 2220 |
| tacaagcaga tacagtataa actcacaaac acagatttga aaataatgca catatggtgt | 2280 |
| tcaaatttga acctttctca tggatttttg tggtgtgggc caatatggtg tttacattat | 2340 |
| ataattcctg ctgtggcaag taaagcacac ttttttttc tcctaaaatg tttttccctg | 2400 |
| tgtatcctat tatggatact ggttttgtta attatgattc tttatttct ctcctttttt | 2460 |
| taggatatag cagtaatgct attactgaaa tgaatttcct ttttctgaaa tgtaatcatt | 2520 |
| gatgcttgaa tgatagaatt ttagtactgt aaacaggctt tagtcattaa tgtgagagac | 2580 |
| ttagaaaaaa tgcttagagt ggactattaa atgtgcctaa atgaatttg cagtaactgg | 2640 |
| tattcttggg ttttcctact taatacacag taattcagaa cttgtattct attatgagtt | 2700 |
| tagcagtctt ttggagtgac cagcaacttt gatgtttgca ctaagatttt atttggaatg | 2760 |

| | |
|---|---|
| caagagaggt tgaaagagga ttcagtagta cacatacaac taatttattt gaactatatg | 2820 |
| ttgaagacat ctaccagttt ctccaaatgc cttttttaaa actcatcaca gaagattggt | 2880 |
| gaaaatgctg agtatgacac ttttcttctt gcatgcatgt cagctacata aacagttttg | 2940 |
| tacaatgaaa attactaatt tgtttgacat tccatgttaa actacggtca tgttcagctt | 3000 |
| cattgcatgt aatgtagacc tagtccatca gatcatgtgt tctggagagt gttctttatt | 3060 |
| caataaagtt ttaatttagt ataaacat | 3088 |

<210> SEQ ID NO 13
<211> LENGTH: 1308
<212> TYPE: DNA
<213> ORGANISM: Homo sapiens

<400> SEQUENCE: 13

| | |
|---|---|
| atgggcgact ggagctttct gggaagactc ttagaaaatg cacaggagca ctccacggtc | 60 |
| atcggcaagg tttggctgac cgtgctgttc atcttccgca tcttggtgct gggggccgcg | 120 |
| gcggaggacg tgtggggcga tgagcagtca gacttcacct gcaacaccca gcagccgggc | 180 |
| tgcgagaacg tctgctacga cagggccttc cccatctccc acatccgctt ctgggcgctg | 240 |
| cagatcatct tcgtgtccac gcccacccte atctacctgg ccacgtgct gcacatcgtg | 300 |
| cgcatggaag agaagaagaa agagagggag gaggaggagc agctgaagag agagagcccc | 360 |
| agccccaagg agccaccgca ggacaatccc tcgtcgcggg acgaccgcgg cagggtgcgc | 420 |
| atggccgggg cgctgctgcg gacctacgtc ttcaacatca tcttcaagac gctgttcgag | 480 |
| gtgggcttca tcgccggcca gtactttctg tacggcttcg agctgaagcc gctctaccgc | 540 |
| tgcgaccgct ggcccgtgcc caacacggtg gactgcttca tctccaggcc cacggagaag | 600 |
| accatcttca tcatcttcat gctggcggtg gcctgcgcgt ccctgctgct caacatgctg | 660 |
| gagatctacc acctgggctg gaagaagctc aagcagggcg tgaccagccg cctcggcccg | 720 |
| gacgcctccg aggccccgct ggggacagcc gatccccgc cctgcccccc agctcccgg | 780 |
| ccgcccgccg ttgccatcgg gttcccaccc tactatgcgc acaccgctgc gcccctggga | 840 |
| caggcccgcg ccgtgggcta ccccggggcc ccgccaccag ccgcggactt caaactgcta | 900 |
| gccctgaccg aggcgcgcgg aaagggccag tccgccaagc tctacaacgg ccaccaccac | 960 |
| ctgctgatga ctgagcagaa ctgggccaac caggcggccg agcggcagcc cccggcgctc | 1020 |
| aaggcttacc cggcagcgtc cacgcctgca gcccccagcc ccgtcggcag cagctccccg | 1080 |
| ccactcgcgc acgaggctga ggcggcgcg gcgcccctgc tgctggatgg gagcggcagc | 1140 |
| agtctggagg ggagcgccct ggcagggacc cccgaggagg aggagcaggc cgtgaccacc | 1200 |
| gcggcccaga tgcaccagcc gcccttgccc ctcggagacc caggtcgggc cagcaaggcc | 1260 |
| agcagggcca gcagcgggcg ggccagaccg gaggacttgg ccatctag | 1308 |

<210> SEQ ID NO 14
<211> LENGTH: 1601
<212> TYPE: DNA
<213> ORGANISM: Homo sapiens

<400> SEQUENCE: 14

| | |
|---|---|
| ctccggccat cgtccccacc tccacctggg ccgcccgcga ggcagcggac ggaggccggg | 60 |
| agccatgggt gactgggct tcctggagaa gttgctggac caggtccgag agcactcgac | 120 |
| cgtggtgggt aagatctggc tgacggtgct cttcatcttc cgcatcctca tcctgggcct | 180 |
| ggccggcgag tcagtgtggg gtgacgagca gtcagatttc gagtgtaaca cggcccagcc | 240 |

| | |
|---|---|
| aggctgcacc aacgtctgct atgaccaggc cttccccatc tcccacatcc gctactgggt | 300 |
| gctgcagttc ctcttcgtca gcacacccac cctggtctac ctgggccatg tcatttacct | 360 |
| gtctcggcga aagagcggc tggcgcagaa ggaggggag ctgcgggcac tgccggccaa | 420 |
| ggacccacag gtggagcggg cgctggccgg catagagctt cagatggcca agatctcggt | 480 |
| ggcagaagat ggtcgcctgc gcattccgcg agcactgatg ggcacctatg tcgccagtgt | 540 |
| gctctgcaag agtgtgctag aggcaggctt cctctatggc cagtggcgcc tgtacggctg | 600 |
| gaccatggag cccgtgtttg tgtgccagcg agcaccctgc ccctacctcg tggactgctt | 660 |
| tgtctctcgc cccacggaga agaccatctt catcatcttc atgttggtgg ttggactcat | 720 |
| ctccctggtg cttaacctgc tggagttggt gcacctgctg tgtcgctgcc tcagccgggg | 780 |
| gatgagggca cggcaaggcc aagacgcacc cccgacccag ggcacctcct cagacccta | 840 |
| cacggaccag ggtcttcttc tacctccccg tggccagggg ccctcatccc caccatgccc | 900 |
| cacctacaat gggctctcat ccagtgagca gaactgggcc aacctgacca cagaggagag | 960 |
| gctggcgtct tccaggcccc ctctcttcct ggacccaccc cctcagaatg ccaaaaaacc | 1020 |
| cccaagtcgt cccagcagct ctgcttctaa gaagcagtat gtatagaggc ctgtggctta | 1080 |
| tgtcacccaa cagaggggtc ctgagaagtc tggctgcctg ggatgccccc tgcccctcc | 1140 |
| tggaaggctc tgcagagatg actgggctgg ggaagcagat gcttgctggc catggagcct | 1200 |
| cattgcaagt tgttcttgaa cacctgaggc cttcctgtgg cccaccaggc actacggctt | 1260 |
| cctctccaga tgtgctttgc ctgagcacag acagtcagca tggaatgctc ttggccaagg | 1320 |
| gtactggggc cctctggcct tttgcagctg atccagagga acccagagcc aacttacccc | 1380 |
| aacctcaccc tatggaacag tcacctgtgc gcaggttgtc ctcaaaccct ctcctcacag | 1440 |
| gaaaaggcgg attgaggctg ctgggtcagc cttgatcgca cagacagagc ttgtgccgga | 1500 |
| tttggccctg tcaaggggac tggtgccttg ttttcatcac tccttcctag ttctactgtt | 1560 |
| caagcttctg aaataaacag gacttgatca caaaaaaaaa a | 1601 |

<210> SEQ ID NO 15
<211> LENGTH: 2574
<212> TYPE: DNA
<213> ORGANISM: Homo sapiens

<400> SEQUENCE: 15

| | |
|---|---|
| gcaaaaagcg tgggcagttg agaagaagc agccagagtg tgaagaagcc cacggaagga | 60 |
| aagtccaggg aggaggaaaa gaagcagaag ttttggcatc tgttccctgg ctgtgccaag | 120 |
| atgggcgatt ggagcttcct gggaaatttc ctggaggaag tacacaagca ctcgaccgtg | 180 |
| gtaggcaagg tctggctcac tgtcctcttc atattccgta tgctcgtgct gggcacagct | 240 |
| gctgagtctt cctgggggga tgagcaggct gatttccggt gtgatacgat tcagcctggc | 300 |
| tgccagaatg tctgctacga ccaggctttc cccatctccc acattcgcta ctgggtgctg | 360 |
| cagatcatct tcgtctccac gccctctctg gtgtacatgg ccacgccat gcacactgtg | 420 |
| cgcatgcagg agaagcgcaa gctacgggag gccgagaggg ccaaagaggt ccggggctct | 480 |
| ggctcttacg agtacccggt ggcagagaag gcagaactgt cctgctggga ggaagggaat | 540 |
| ggaaggattg ccctccaggg cactctgctc aacacctatg tgtgcagcat cctgatccgc | 600 |
| accaccatgg aggtggggct tcattgtggc cagtacttca tctacggaat cttcctgacc | 660 |
| accctgcatg tctgccgcag gagtcccgt ccccacccgg tcaactgtta cgtatcccgg | 720 |
| cccacagaga agaatgtctt cattgtcttt atgctggctg tggctgcact gtccctcctc | 780 |

| | |
|---|---|
| cttagcctgg ctgaactcta ccacctgggc tggaagaaga tcagacagcg atttgtcaaa | 840 |
| ccgcggcagc acatggctaa gtgccagctt tctggcccct ctgtgggcat agtccagagc | 900 |
| tgcacaccac cccccgactt taatcagtgc ctggagaatg ccctgggggg aaaattcttc | 960 |
| aatcccttca gcaataatat ggcctcccaa caaaacacag acaacctggt caccgagcaa | 1020 |
| gtacgaggtc aggagcagac tcctggggaa ggtttcatcc aggttcgtta tggccagaag | 1080 |
| cctgaggtgc ccaatggagt ctcaccaggt caccgccttc cccatggcta tcatagtgac | 1140 |
| aagcgacgtc ttagtaaggc cagcagcaag gcaaggtcag atgacctatc agtgtgaccc | 1200 |
| tcctttatgg gaggatcagg accagtgggg aacaaaggag gctcagagaa gaaagacgtg | 1260 |
| tcccttctga actgatgctt tctcactgtc atcactgctt ggctcctttg agccccgggt | 1320 |
| ctcaatgacg ttgctcatta attctagaaa ctataaccag gctctgggga tagtaagaga | 1380 |
| ggtgacaacc cacccagact gcagttccct ccccacccctc tacccagtat acgaagcctt | 1440 |
| tcagattact catgaaacag ggtagaggga agaagggaa gcatggcaaa agctggcctg | 1500 |
| gaagggatag ccagagggat agaatgactc tctctctaca taccagcagc ataccaaatg | 1560 |
| cgttctctaa gttcctacct ccttgacctg atcaccctcc ctcctccaag gaagagctca | 1620 |
| aagttcccag ccaatagaca gcatgaatca aggaacttgc attatatgtg ctcttgaatc | 1680 |
| tgttgtctcc atggaccatt cctcggagta gtggtgagat ggccttgggt tgcccttggc | 1740 |
| ttctcctccc tctactcagc cttaaaaagg gcttcttgga actttaccag cagcctcagc | 1800 |
| tttacaaatg ccttggtatg tacctctggc aaatgcccca ccttggtgat gttgcaacct | 1860 |
| ttccttctgc tagggtgtac acctagcctg tgcaggtgtc agccctgcta gggagtcact | 1920 |
| gtacacacaa actctactgg aattcctgcc aacatctgtc accctgcagc tcctttacag | 1980 |
| ttcaatccaa tgatagaaac catcccttcc ctttctccct tggctgttca cccagccatt | 2040 |
| ccctgaaggc cttaccaaca ggaatatcca agaagctgtt gtccctctc gaaccctgac | 2100 |
| cagatcatca gccactgagg ccagtggaat ttccccaggc cttgttaaaa caaagaaagc | 2160 |
| attgtacctc tcagattccc cttgtggaaa aaaaaattct gctgtgaaga tgaaaataaa | 2220 |
| aatggagaga aaacactgga aaactatttt cccctcctat ttacttcctt tgctgactgc | 2280 |
| caacttagtg ccaagaggag gtgtgatgac agctatggag gcccccagat ctctctctcc | 2340 |
| tggaggcttt agcaggggca aggaaatagt aggggaatct ccagctctct tggcagggcc | 2400 |
| tttatttaaa gagcgcagag attcctatgt ctccctagtg cccctaatga gactgccaag | 2460 |
| tgggggctgt agaaaagcct tgccttcccc agggattggc ctggtctctg tattcactgg | 2520 |
| atccataatg ggttgctgtt gttttggatg aaggtaaacg atgcttggaa ttgg | 2574 |

<210> SEQ ID NO 16
<211> LENGTH: 1191
<212> TYPE: DNA
<213> ORGANISM: Homo sapiens

<400> SEQUENCE: 16

| | |
|---|---|
| atgagttgga gctttctgac tcgcctgcta gaggagattc acaaccattc cacatttgtg | 60 |
| gggaagatct ggctcactgt tctgattgtc ttccggatcg tccttacagc tgtaggagga | 120 |
| gaatccatct attacgatga gcaaagcaaa tttgtgtgca acacagaaca gccgggctgt | 180 |
| gagaatgtct gttatgatgc gtttgcacct ctctcccatg tacgcttctg ggtgttccag | 240 |
| atcatcctgg tggcaactcc ctctgtgatg tacctgggct atgctatcca caagattgcc | 300 |
| aaaatggagc acggtgaagc agacaagaag gcagctcgga gcaagccta tgcaatgcgc | 360 |

| | |
|---|---|
| tggaaacaac accgggctct ggaagaaacg gaggaggaca acgaagagga tcctatgatg | 420 |
| tatccagaga tggagttaga aagtgataag gaaaataaag agcagagcca acccaaacct | 480 |
| aagcatgatg gccgacgacg gattcgggaa gatgggctca tgaaaatcta tgtgctgcag | 540 |
| ttgctggcaa ggaccgtgtt tgaggtgggt tttctgatag ggcagtattt tctgtatggc | 600 |
| ttccaagtcc acccgtttta tgtgtgcagc agacttcctt gtcctcataa gatagactgc | 660 |
| tttatttcta gacccactga aaagaccatc ttccttctga taatgtatgg tgttacaggc | 720 |
| cttttgcctct tgcttaacat ttgggagatg cttcatttag ggtttgggac cattcgagac | 780 |
| tcactaaaca gtaaaaggag ggaacttgag gatccgggtg cttataatta tcctttcact | 840 |
| tggaatacac catctgctcc ccctggctat aacattgctg tcaaaccaga tcaaatccag | 900 |
| tacaccgaac tgtccaatgc taagatcgcc tacaagcaaa acaaggccaa cacagcccag | 960 |
| gaacagcagt atggcagcca tgaggagaac ctcccagctg acctggaggc tctgcagcgg | 1020 |
| gagatcagga tggctcagga acgcttggat ctggcagttc aggcctacag tcaccaaaac | 1080 |
| aaccctcatg gtccccggga gaagaaggcc aaagtggggt ccaaagctgg gtccaacaaa | 1140 |
| agcactgcca gtagcaaatc aggggatggg aagaactctg tctggattta a | 1191 |

<210> SEQ ID NO 17
<211> LENGTH: 1362
<212> TYPE: DNA
<213> ORGANISM: Homo sapiens

<400> SEQUENCE: 17

| | |
|---|---|
| agcgccaaga gagaaagagc acatatttct ccgtgggaca ctccttgtat tggtgggtga | 60 |
| gaaatgggcg actggagttt cctggggaac atcttggagg aggtgaatga gcactccacc | 120 |
| gtcatcggca gagtctggct caccgtgctt ttcatcttcc ggatcctcat ccttggcacg | 180 |
| gccgcagagt tcgtgtgggg ggatgagcaa tccgacttcg tgtgcaacac ccagcagcct | 240 |
| ggctgcgaga acgtctgcta cgacgaggcc tttcccatct cccacattcg cctctgggtg | 300 |
| ctgcagatca tcttcgtctc cacccccgtcc ctgatgtacg tggggcacgc ggtgcactac | 360 |
| gtccgcatgg aggagaagcg caaaagccgc gacgaggagc tgggccagca ggcggggact | 420 |
| aacggcggcc cggaccaggg cagcgtcaag aagagcagcg gcagcaaagg cactaagaag | 480 |
| ttccggctgg aggggacccct gctgaggacc tacatctgcc acatcatctt caagaccctc | 540 |
| tttgaagtgg gcttcatcgt gggccactac ttcctgtacg ggttccggat cctgcctctg | 600 |
| taccgctgca gccggtggcc ctgccccaat gtggtggact gcttcgtgtc ccggcccacg | 660 |
| gagaaaacca tcttcatcct gttcatgttg tctgtggcct ctgtgtccct attcctcaac | 720 |
| gtgatggagt tgagccacct gggcctgaag gggatccggt ctgccttgaa gaggcctgta | 780 |
| gagcagcccc tgggggagat tcctgagaaa tccctccact ccattgctgt ctcctccatc | 840 |
| cagaaagcca agggctatca gcttctagaa gaagagaaaa tcgtttccca ctatttcccc | 900 |
| ttgaccgagg ttgggatggt ggagaccagc ccactgcctg ccaagccttt caatcagttc | 960 |
| gaggagaaga tcagcacagg acccctgggg gacttgtccc ggggctacca agagacactg | 1020 |
| ccttcctacg ctcaggtggg ggcacaagaa gtggagggcg aggggccgcc tgcagaggag | 1080 |
| ggagccgaac ccgaggtggg agaagaagaag gaggaagcag agaggctgac cacgagggag | 1140 |
| caggagaagg tggccgtgcc agaggggag aaagtagaga cccccggagt ggataaggag | 1200 |
| ggtgaaaaag aagagccgca gtcggagaag gtgtcaaagc aagggctgcc agctgagaag | 1260 |

| acaccttcac tctgtccaga gctgacaaca gatgatgcca gacccctgag caggctaagc | 1320 |
| aaagccagca gccgagccag gtcagacgat ctaaccgtat ga | 1362 |

<210> SEQ ID NO 18
<211> LENGTH: 966
<212> TYPE: DNA
<213> ORGANISM: Homo sapiens

<400> SEQUENCE: 18

| atgggggaat ggaccatctt ggagaggctg ctagaagccg cggtgcagca gcactccact | 60 |
| atgatcggaa ggatcctgtt gactgtggtg gtgatcttcc ggatcctcat tgtggccatt | 120 |
| gtggggaga cggtgtacga tgatgagcag accatgtttg tgtgcaacac cctgcagccc | 180 |
| ggctgtaacc aggcctgcta tgaccgggcc ttccccatct cccacatacg ttactgggtc | 240 |
| ttccagatca taatggtgtg taccccagt ctttgcttca tcacctactc tgtgcaccag | 300 |
| tccgccaagc agcgagaacg ccgctactct acagtcttcc tagccctgga cagagacccc | 360 |
| cctgagtcca taggaggtcc tggaggaact gggggtgggg gcagtggtgg gggcaaacga | 420 |
| gaagataaga agttgcaaaa tgctattgtg aatgggtgc tgcagaacac agagaacacc | 480 |
| agtaaggaga cagagccaga ttgtttagag gttaaggagc tgactccaca cccatcaggt | 540 |
| ctacgcactg catcaaaatc caagctcaga aggcaggaag gcatctcccg cttctacatt | 600 |
| atccaagtgg tgttccgaaa tgccctggaa attgggttcc tggttggcca atattttctc | 660 |
| tatggctta gtgtcccagg gttgtatgag tgtaaccgct accctgcat caaggaggtg | 720 |
| gaatgttatg tgtcccggcc aactgagaag actgtctttc tagtgttcat gtttgctgta | 780 |
| agtggcatct gtgttgtgct caacctggct gaactcaacc acctgggatg cgcaagatc | 840 |
| aagctggctg tgcgaggggc tcaggccaag agaaagtcaa tctatgagat tcgtaacaag | 900 |
| gacctgccaa gggtcagtgt tcccaatttt ggcaggactc agtccagtga ctctgcctat | 960 |
| gtgtga | 966 |

<210> SEQ ID NO 19
<211> LENGTH: 1901
<212> TYPE: DNA
<213> ORGANISM: Homo sapiens

<400> SEQUENCE: 19

| cagggagttg tggttgcaac actgtactcc agcctgggca acagagggag actctgtctc | 60 |
| aacaaacaaa caaacaaaga aaaaacccca cagctatcta gggaaaaagt aaagcaacca | 120 |
| gcatatagaa gtgacatatt gttatatttt caccataggt ttgctttaag aaatagtgct | 180 |
| cccttcagaa tggaagaatt tatctgcctc ttatttgatg tggatcagag ctaagatggc | 240 |
| tgactaaaata aacatggggg actggaatct ccttggagat actctggagg aagttcacat | 300 |
| ccactccacc atgattggaa agatctggct caccatcctg ttcatatttc gaatgcttgt | 360 |
| tctgggtgta gcagctgaag atgtctggaa tgatgagcag tctggcttca tctgcaaatac | 420 |
| agaacaacca ggctgcagaa atgtatgcta cgaccaggcc tttcctatct ccctcattag | 480 |
| atactgggtt ctgcaggtga tatttgtgtc ttcaccatcc ctggtctaca tgggccatgc | 540 |
| attgtaccga ctgagagttc ttgaggaaga gaggcaaagg atgaaagctc agttaagagt | 600 |
| agaactggag gaggtagagt ttgaaatgcc tagggatcgg aggagattgg agcaagagct | 660 |
| ttgtcagctg gagaaaagga aactaaataa agctccactc agaggaacct tgctttgcac | 720 |
| ttatgtgata cacattttca ctcgctctgt ggttgaagtt ggattcatga ttggacagta | 780 |

-continued

| | |
|---|---|
| ccttttatat ggatttcact tagagccgct atttaagtgc catggccacc cgtgtccaaa | 840 |
| tataatcgac tgttttgtct caagaccaac agaaaagaca atattcctat tatttatgca | 900 |
| atctatagcc actatttcac ttttcttaaa cattcttgaa attttccacc taggttttaa | 960 |
| aaagattaaa agagggcttt ggggaaaata caagttgaag aaggaacata atgaattcca | 1020 |
| tgcaaacaag gcaaaacaaa atgtagccaa ataccagagc acatctgcaa attcactgaa | 1080 |
| gcgactccct tctgcccctg attataatct gttagtggaa aagcaaacac acactgcagt | 1140 |
| gtaccctagt ttaaattcat cttctgtatt ccagccaaat cctgacaatc atagtgtaaa | 1200 |
| tgatgagaaa tgcattttgg atgaacagga aactgtactt tctaatgaga tttccacact | 1260 |
| tagtactagt tgtagtcatt ttcaacacat cagttcaaac aataacaaag acactcataa | 1320 |
| aatatttgga aaagaactta atggtaacca gttaatggaa aaagagaaa ctgaaggcaa | 1380 |
| agacagcaaa aggaactact actctagagg tcaccgttct attccaggtg ttgctataga | 1440 |
| tggagagaac aacatgaggc agtcacccca aacagttttc tccttgccag ctaactgcga | 1500 |
| ttggaaaccg cggtggctta gagctacatg gggttcctct acagaacatg aaaaccgggg | 1560 |
| gtcacctcct aaaggtaacc tcaagggcca gttcagaaag ggcacagtca gaacccttcc | 1620 |
| tccttcacaa ggagattctc aatcacttga cattccaaac actgctgatt ctttgggagg | 1680 |
| gctgtccttt gagccagggt tggtcagaac ctgtaataat cctgtttgtc ctccaaatca | 1740 |
| cgtagtgtcc ctaacgaaca atctcattgg taggcgggtt cccacagatc ttcagatcta | 1800 |
| aacagcggtt ggcttttaga cattatatat attatcagag aagtagccta gtggtcgtgg | 1860 |
| ggcacagaaa aaatagatag gggcagctct aaagaccagc t | 1901 |

<210> SEQ ID NO 20
<211> LENGTH: 1311
<212> TYPE: DNA
<213> ORGANISM: Homo sapiens

<400> SEQUENCE: 20

| | |
|---|---|
| atgagctgga gcttcctgac gcggctgctg gaggagatcc acaaccactc caccttcgtg | 60 |
| ggcaaggtgt ggctcacggt gctggtggtc ttccgcatcg tgctgacggc tgtgggcggc | 120 |
| gaggccatct actcggacga gcaggccaag ttcacttgca acacgcggca gccaggctgc | 180 |
| gacaacgtct gctatgacgc cttcgcgccc tgtcgcacg tgcgcttctg ggtcttccag | 240 |
| attgtggtca tctccacgcc ctcggtcatg tacctgggct acgccgtgca ccgcctggcc | 300 |
| cgtgcgtctg agcaggagcg gcgccgcgcc tccgccgcc gccggggcc acgccgcgcg | 360 |
| ccccgagcgc acctgccgcc cccgcacgcc ggctggcctg agcccgccga cctgggcgag | 420 |
| gaggagccca tgctgggcct gggcgaggag gaggaggagg aggagacggg ggcagccgag | 480 |
| ggcgccggcg aggaagcgga ggaggcaggc gcggaggagg cgtgcactaa ggcggtcggc | 540 |
| gctgacggca aggcggcagg gaccccgggc ccgaccgggc aacacgatgg gcggaggcgc | 600 |
| atccagcggg agggcctgat gcgcgtgtac gtggcccagc tggtgccag gcagctttc | 660 |
| gaggtggcct tcctggtggg ccagtacctg ctgtacggct tcgaggtgcg accgttcttt | 720 |
| ccctgcagcc gccagcctg cccgcacgtg gtggactgct cgtgtcgcg ccctactgaa | 780 |
| aagacggtct tcctgctggt tatgtacgtg gtcagctgcc tgtgcctgct gctcaacctc | 840 |
| tgtgagatgg cccacctggg cttgggcagc gcgcaggacg cggtgcgcgg ccgccgcggc | 900 |
| ccccggcct ccgcccccgc cccgcgccg cggccccgc cctgcgcctt ccctgcggcg | 960 |
| gccgctggct tggcctgccc gcccgactac agcctggtgg tgcgggcggc cgagcgcgct | 1020 |

```
cgggcgcatg accagaacct ggcaaacctg gccctgcagg cgctgcgcga cggggcagcg    1080
gctggggacc gcgaccggga cagttcgccg tgcgtcggcc tccctgcggc ctccggggg     1140 ccccccagag caggcgcccc cgcgtcccgg acgggcagtg ctacctctgc gggcactgtc    1200
ggggagcagg gccggcccgg cacccacgag cggccaggag ccaagcccag ggctggctcc    1260
gagaagggca gtgccagcag cagggacggg aagaccaccg tgtggatctg a             1311
```

<210> SEQ ID NO 21
<211> LENGTH: 1588
<212> TYPE: DNA
<213> ORGANISM: Homo sapiens

<400> SEQUENCE: 21

```
agacattctc tgggaaaggg cagcagcagc caggtgtggc agtgacaggg aggtgtgaat      60
gaggcaggat gaactggaca ggtttgtaca ccttgctcag tggcgtgaac cggcattcta     120
ctgccattgg ccgagtatgg ctctcggtca tcttcatctt cagaatcatg gtgctggtgg     180
tggctgcaga gagtgtgtgg ggtgatgaga aatcttcctt catctgcaac acactccagc     240
ctggctgcaa cagcgtttgc tatgaccaat tcttccccat ctcccatgtg cggctgtggt     300
ccctgcagct catcctagtt tccacccag ctctcctcgt ggccatgcac gtggctcacc      360
agcaacacat agagaagaaa atgctacggc ttgagggcca tggggacccc ctacacctgg     420
aggaggtgaa gaggcacaag gtccacatct cagggacact gtggtggacc tatgtcatca     480
gcgtggtgtt ccggctgttg tttgaggccg tcttcatgta tgtcttttat ctgctctacc     540
ctggctatgc catggtgcgg ctggtcaagt gcgacgtcta cccctgcccc aacacagtgg     600
actgcttcgt gtcccgcccc accgagaaaa ccgtcttcac cgtcttcatg ctagctgcct     660
ctggcatctg catcatcctc aatgtggccg aggtggtgta cctcatcatc cgggcctgtg     720
cccgccgagc ccagcgccgc tccaatccac cttcccgcaa gggctcgggc ttcggccacc     780
gcctctcacc tgaatacaag cagaatgaga tcaacaagct gctgagtgag caggatggct     840
ccctgaaaga catactgcgc cgcagccctg gcaccggggc tgggctggct gaaaagagcg     900
accgctgctc ggcctgctga tgccacatac caggcaacct cccatcccac ccccgaccct     960
gccctgggcg agcccctcct tctccctgc cggtgcacag gcctctgcct gctggggatt     1020
actcgatcaa aaccttcctt ccctggctac ttccttcct cccggggcct tccttttgag     1080
gagctggagg ggtggggagc tagaggccac ctatgccagt gctcaaggtt actgggagtg     1140
tgggctgccc ttgttgcctg caccctcc tcttccctct ccctctctct gggaccactg       1200
ggtacaagag atgggatgct ccgacagcgt ctccaattat gaaactaatc ttaaccctgt     1260
gctgtcagat accctgtttc tggagtcaca tcagtgagga gggatgtggg taagaggagc     1320
agagggcagg ggtgctgtgg acatgtgggt ggagaaggga gggtggccag cactagtaaa     1380
ggaggaatag tgcttgctgg ccacaaggaa aaggaggagg tgtctgggt gagggagtta      1440 gggagagaga agcaggcaga taagttggag caggggttgg tcaaggccac ctctgcctct     1500
agtccccaag gcctctctct gcctgaaatg ttacacatta aacaggattt tacagcaaaa     1560
aaaaaaaaaa aaaaaaaaa aaaaaaaa                                         1588
```

<210> SEQ ID NO 22
<211> LENGTH: 2263
<212> TYPE: DNA
<213> ORGANISM: Homo sapiens

```
<400> SEQUENCE: 22 cggagccct  cggcggcgcc  cggcccagga  cccgcctagg  agcgcaggag  ccccagcgca    60
gagaccccaa  cgccgagacc  cccgccccgg  ccccgccgcg  cttcctcccg  acgcagagca   120
aaccgcccag  agtagaagat  ggattggggc  acgctgcaga  cgatcctggg  gggtgtgaac   180
aaacactcca  ccagcattgg  aaagatctgg  ctcaccgtcc  tcttcatttt  tcgcattatg   240
atcctcgttg  tggctgcaaa  ggaggtgtgg  ggagatgagc  aggccgactt  tgtctgcaac   300
accctgcagc  caggctgcaa  gaacgtgtgc  tacgatcact  acttccccat  ctcccacatc   360
cggctatggg  ccctgcagct  gatcttcgtg  tccacgccag  cgctcctagt  ggccatgcac   420
gtggcctacc  ggagacatga  agaagagg    aagttcatca  aggggagat   aaagagtgaa   480 tttaaggaca  tcgaggagat  caaaacccag  aaggtccgca  tcgaaggctc  cctgtggtgg   540
acctacacaa  gcagcatctt  cttccgggtc  atcttcgaag  ccgccttcat  gtacgtcttc   600
tatgtcatgt  acgacggctt  ctccatgcag  cggctggtga  agtgcaacgc  ctggccttgt   660
cccaacactg  tggactgctt  tgtgtcccgg  cccacggaga  agactgtctt  cacagtgttc   720
atgattgcag  tgtctggaat  ttgcatcctg  ctgaatgtca  ctgaattgtg  ttatttgcta   780
attagatatt  gttctgggaa  gtcaaaaaag  ccagtttaac  gcattgccca  gttgttagat   840
taagaaatag  acagcatgag  agggatgagg  caacccgtgc  tcagctgtca  aggctcagtc   900
gccagcattt  cccaacacaa  agattctgac  cttaaatgca  accatttgaa  accctgtag   960 gcctcaggtg  aaactccaga  tgccacaatg  gagctctgct  cccctaaagc  tcaaaacaa   1020 aggcctaatt  ctatgcctgt  cttaattttc  tttcacttaa  gttagttcca  ctgagacccc  1080
aggctgttag  gggttattgg  tgtaaggtac  tttcatattt  taaacagagg  atatcggcat  1140
ttgtttcttt  ctctgaggac  aagagaaaaa  agccaggttc  cacagaggac  acagagaagg  1200
tttgggtgtc  ctcctggggt  tcttttttgcc  aactttcccc  acgttaaagg  tgaacattgg  1260
ttctttcatt  tgctttggaa  gttttaatct  ctaacagtgg  acaaagttac  cagtgcctta  1320
aactctgtta  cacttttttgg  aagtgaaaac  tttgtagtat  gataggttat  tttgatgtaa  1380
agatgttctg  gataccatta  tatgttcccc  ctgtttcaga  ggctcagatt  gtaatatgta  1440
aatggtatgt  cattcgctac  tatgatttaa  tttgaaatat  ggtcttttgg  ttatgaatac  1500
tttgcagcac  agctgagagg  ctgtctgttg  tattcattgt  ggtcatagca  cctaacaaca  1560
ttgtagcctc  aatcgagtga  gacagactag  aagttcctag  tgatggctta  tgatagcaaa  1620
tggcctcatg  tcaaatattt  agatgtaatt  ttgtgtaaga  aatacagact  ggatgtacca  1680
ccaactacta  cctgtaatga  caggcctgtc  caacacatct  cccttttcca  tgactgtggt  1740
agccagcatc  ggaaagaacg  ctgatttaaa  gaggtcgctt  gggaatttta  ttgacacagt  1800
accatttaat  ggggaggaca  aaatggggca  ggggagggag  aagtttctgt  cgttaaaaac  1860
agatttggaa  agactggact  ctaaattctg  ttgattaaag  atgagctttg  tctacttcaa  1920
aagtttgttt  gcttacccct  tcagcctcca  attttttaag  tgaaaatata  actaataaca  1980
tgtgaaaaga  atagaagcta  aggtttagat  aaatattgag  cagatctata  ggaagattga  2040
acctgaatat  tgccattatg  cttgacatgg  tttccaaaaa  atggtactcc  acatacttca  2100
gtgagggtaa  gtattttcct  gttgtcaaga  atagcattgt  aaaagcattt  tgtaataata  2160
aagaatagct  ttaatgatat  gcttgtaact  aaaataattt  tgtaatgtat  caaatacatt  2220
taaaacatta  aaatataatc  tctataataa  aaaaaaaaa  aaa                       2263
```

<210> SEQ ID NO 23
<211> LENGTH: 2220
<212> TYPE: DNA
<213> ORGANISM: Homo sapiens

<400> SEQUENCE: 23

```
gaacttcttt cctggcacag gactcactgt gcccctccc gctgtgggta caaggtctgc      60
cccccacccc agctctccaa agcccaccgg cctccctgga ggccgaggtc gacggcccgt     120
cgcaccggga ggggggctc ccaggggtgc cccacgcacg gtcaaggtcc gcgccaagc       180
ggggaccggg ctgggccgga agcgggcacg gtactcgcgg caaactagcg tgggcgagtc     240
ctgattgcag tcggacctgc cgccgcggca cttaacagtt tgcagagtgc ttcccgcccc    300
tgatctcatt ggagccttcg gacagcccag cccatggcca ccgatgcccc catttcacgc    360
ctgaggaagc ggaggctcag acgggccacc agcccctccg gaggctggcc cgggagcgcc    420
tggcagcgtc gggtctagga gccggctccc tcctgctccc cctccgcgc cgcccggggt     480
gtgcccgccg tctgtgtgca ccactgctga gcccagctcc ggcgccctcg cctctgctgt    540
gggcccgggg gacgcggggt caggccaccg cgttggccag gccgctgcag gtaggcacgg    600
cccccaccag gcgccatgga ctggaagaca ctccaggccc tactgagcgg tgtgaacaag    660
tactccacag cgttcgggcg catctggctg tccgtggtgt tcgtcttccg ggtgctggta    720
tacgtggtgg ctgcagagcg cgtgtggggg gatgagcaga aggactttga ctgcaacacc    780
aagcagcccg gctgcaccaa cgtctgctac gacaactact tccccatctc caacatccgc    840
ctctgggccc tgcagctcat cttcgtcaca tgcccctcgc tgctggtcat cctgcacgtg    900
gcctaccgtg aggagcggga cgccggcac cgccagaaac acggggacca gtgcgccaag    960
ctgtacgaca acgcaggcaa gaagcacgga ggcctgtggt ggacctacct gttcagcctc   1020
atcttcaagc tcatcattga gttcctcttc ctctacctgc tgcacactct ctggcatggc   1080
ttcaatatgc cgcgcctggt gcagtgtgcc aacgtggccc cctgccccaa catcgtggac   1140
tgctacattg cccgacctac cgagaagaaa atcttcacct acttcatggt gggcgcctcc   1200
gccgtctgca tcgtactcac catctgtgag ctctgctacc tcatctgcca cagggtcctg   1260
cgaggcctgc acaaggacaa gccctcgaggg ggttgcagcc cctcgtcctc cgccagccga   1320
gcttccacct gccgctgcca ccacaagctg tggaggctg gggaggtgga tccagaccca   1380
ggcaataaca agctgcaggc ttcagcaccc aacctgaccc ccatctgacc acagggcagg   1440
ggtggggcaa catgcgggct gccaatggga catgcagggc ggtgtggcag gtggagaggt   1500
cctacagggg ctgagtgacc ccactctgag ttcactaagt tatgcaactt tcgttttggc   1560
agatattttt tgacactggg aactgggctg tctagccggg tataggtaac ccacaggccc   1620
agtgccagcc ctcaaaggac atagactttg aaacaagcga attaactatc tacgctgcct   1680
gcaagggggcc acttagggca ctgctagcag ggcttcaacc aggaagggat caacccagga   1740
agggatgatc aggagaggct tccctgagga cataatgtgt aagagaggtg agaagtgctc   1800
ccaagcagac acaacagcag cacagaggtc tggaggccac acaaaaagtg atgctcgccc   1860
tgggctagcc tcagcagacc taaggcatct ctactccctc cagaggagcc gcccagattc   1920
ctgcagtgga gaggaggtct tccagcagca gcaggtctgg agggctgaga atgaacctga   1980
ctagaggttc tggagatacc cagaggtccc ccaggtcatc acttggctca gtggaagccc   2040
tcttccccca atcctactc cctcagcctc aggcagtggt gctcccatct tcctccccac   2100
```

```
aactgtgctc aggctggtgc cagccttca gaccctgctc ccagggactt gggtggatgc    2160
gctgatagaa catcctcaag acagtttcct tgaaatcaat aaatactgtg ttttataaaa    2220
```

<210> SEQ ID NO 24
<211> LENGTH: 1243
<212> TYPE: DNA
<213> ORGANISM: Homo sapiens

<400> SEQUENCE: 24

```
caaggctccc aaggcctgag tgggcaggta gcacccaggt atagaccttc cacgtgcagc      60
acccaggaca cagccagcat gaactgggca tttctgcagg gcctgctgag tggcgtgaac     120
aagtactcca cagtgctgag ccgcatctgg ctgtctgtgg tgttcatctt tcgtgtgctg     180
gtgtacgtgg tggcagcgga ggaggtgtgg gacgatgagc agaaggactt tgtctgcaac     240
accaagcagc ccggctgccc caacgtctgc tatgacgagt tcttcccgt gtcccacgtg      300 cgcctctggg ccctacagct catcctggtc acgtgcccct cactgctcgt ggtcatgcac     360
gtggcctacc gcgaggaacg cgagcgcaag caccacctga acacgggcc caatgccccg      420 tccctgtacg acaacctgag caagaagcgg gcggactgt ggtggacgta cttgctgagc      480
ctcatcttca aggccgccgt ggatgctggc ttcctctata tcttccaccg cctctacaag     540
gattatgaca tgccccgcgt ggtggcctgc tccgtggagc cttgccccca cactgtggac     600
tgttacatct cccggcccac ggagaagaag gtcttcacct acttcatggt gaccacagct     660
gccatctgca tcctgctcaa cctcagtgaa gtcttctacc tggtgggcaa gaggtgcatg     720
gagatcttcg gccccaggca ccggcggcct cggtgccggg aatgcctacc cgatacgtgc     780
ccaccatatg tcctctccca gggagggcac cctgaggatg ggaactctgt cctaatgaag     840
gctgggtcgg ccccagtgga tgcagtgggg tatccataac ctgcgagatc agcagataag     900
atcaacaggt cccccccaca tgaggccacc caggaaaaaa ggcagggca gtggcatcct      960 tgccgtagca gggtggtgag gagggtggct gtggggctc aggaagctcg cccagggcc     1020 aatgtgggag gttgggggta gtttggtccc tgggtcctga gcctcagggg agggaggttg   1080
atagctactg gggattttgt atatggcaac agtatatgtc aaacctctta ttaaatatga   1140
ttttcccagt aaaaaaaaaa aaaaaaaaaa aaaaaaaaa aaaaaaaaaa aaaaaaaaaa     1200
aaaaaaaaaa aaaaaaaaaa aaaaaaaaaa aaaaaaaaaa aaa                       1243
```

<210> SEQ ID NO 25
<211> LENGTH: 1299
<212> TYPE: DNA
<213> ORGANISM: Homo sapiens

<400> SEQUENCE: 25

```
atgaaattca agctgcttgc tgagtcctat tgccggctgc tgggagccag agagccctg       60 aggagtagtc actcagtagc agctgacgcg tgggtccacc atgaactgga gtatctttga    120
gggactcctg agtgggtca acaagtactc cacagccttt gggcgcatct ggctgtctct     180
ggtcttcatc ttccgcgtgc tggtgtacct ggtgacggcc gagcgtgtgt ggagtgatga    240
ccacaaggac ttcgactgca atactcgcca gcccggctgc tccaacgtct gctttgatga    300
gttcttccct gtgtcccatg tgcgcctctg ggccctgcag cttatcctgg tgacatgccc    360
ctcactgctc gtggtcatgc acgtggccta ccggggaggtt caggagaaga ggcaccgaga    420
agcccatggg gagaacagtg ggcgcctcta cctgaacccc ggcaagaagc ggggtgggct    480
ctggtggaca tatgtctgca gcctagtgtt caaggcgagc gtggacatcg cctttctcta    540
```

```
tgtgttccac tcattctacc ccaaatatat cctccctcct gtggtcaagt gccacgcaga    600
tccatgtccc aatatagtgg actgcttcat ctccaagccc tcagagaaga acattttcac    660
cctcttcatg gtggccacag ctgccatctg catcctgctc aacctcgtgg agctcatcta    720
cctggtgagc aagagatgcc acgagtgcct ggcagcaagg aaagctcaag ccatgtgcac    780
aggtcatcac ccccacggta ccacctcttc ctgcaaacaa gacgacctcc tttcgggtga    840
cctcatcttt ctgggctcag acagtcatcc tcctctctta ccagaccgcc cccgagacca    900
tgtgaagaaa accatcttgt gagggctgc ctggactggt ctggcaggtt gggcctggat    960
ggggaggctc tagcatctct cataggtgca acctgagagt gggggagcta agccatgagg   1020
taggggcagg caagagagag gattcagacg ctctgggagc cagttcctag tcctcaactc   1080
cagccacctg ccccagctcg acggcactgg gccagttccc cctctgctct gcagctcggt   1140
ttccttttct agaatggaaa tagtgagggc caatgcccag ggttggaggg aggagggcgt   1200
tcatagaaga acacacatgc gggcaccttc atcgtgtgtg gcccactgtc agaacttaat   1260
aaaagtcaac tcatttgctg gaaaaaaaaa aaaaaaaaa                          1299
```

<210> SEQ ID NO 26
<211> LENGTH: 1805
<212> TYPE: DNA
<213> ORGANISM: Homo sapiens

<400> SEQUENCE: 26

```
ctgggaagac gctggtcagt tcacctgccc cactggttgt tttttaaaca aattctgata     60
caggcgacat cctcactgac cgagcaaaga ttgacattcg tatcatcact gtgcaccatt    120
ggcttctagg cactccagtg gggtaggaga aggaggtctg aaaccctcgc agagggatct    180
tgccctcatt ctttgggtct gaaacactgg cagtcgttgg aaacaggact cagggataaa    240
ccagcgcaat ggattggggg acgctgcaca cttttcatcgg gggtgtcaac aaacactcca    300
ccagcatcgg gaaggtgtgg atcacagtca tctttatttt ccgagtcatg atcctcgtgg    360
tggctgccca ggaagtgtgg ggtgacgagc aagaggactt cgtctgcaac acactgcaac    420
cgggatgcaa aaatgtgtgc tatgaccact ttttcccggt gtcccacatc cggctgtggg    480
ccctccagct gatcttcgtc tccaccccag cgctgctggt ggccatgcat gtggcctact    540
acaggcacga aaccactcgc aagttcaggc gaggagagaa gaggaatgat ttcaaagaca    600
tagaggacat taaaaagcag aaggttcgga tagagggtc gctgtggtgg acgtacacca    660
gcagcatctt tttccgaatc atctttgaag cagcctttat gtatgtgttt tacttccttt    720
acaatgggta ccacctgccc tgggtgttga atgtgggat tgacccctgc cccaaccttg    780
ttgactgctt tatttctagg ccaacagaga agaccgtgtt taccatttt atgatttctg    840 cgtctgtgat ttgcatgctg cttaacgtgg cagagttgtg ctacctgctg ctgaaagtgt    900
gttttaggag atcaaagaga gcacagacgc aaaaaaatca ccccaatcat gccctaaagg    960
agagtaagca gaatgaaatg aatgagctga tttcagatag tggtcaaaat gcaatcacag   1020
gtttcccaag ctaaacattt caaggtaaaa tgtagctgcg tcataaggag acttctgtct   1080
tctccagaag gcaataccaa cctgaaagtt ccttctgtag cctgaagagt ttgtaaatga   1140 cttttcataat aaatagacac ttgagttaac ttttttgtagg atacttgctc cattcataca   1200
caacgtaatc aaatatgtgg tccatctctg aaaacaagag actgcttgac aaaggagcat   1260
tgcagtcact ttgacaggtt ccttttaagt ggactctctg acaaagtggg tactttctga   1320
aaatttatat aactgttgtt gataaggaac atttatccag gaattgatac tttattagg    1380
```

```
aaaagatatt tttataggct tggatgtttt tagttctgac tttgaattta tataaagtat    1440
ttttataatg actggtcttc cttacctgga aaaacatgcg atgttagttt tagaattaca    1500
ccacaagtat ctaaatttgg aacttacaaa gggtctatct tgtaaatatt gttttgcatt    1560
gtctgttggc aaatttgtga actgtcatga tacgcttaag gtggaaagtg ttcattgcac    1620
aatatatttt tactgctttc tgaatgtaga cggaacagtg tggaagcaga aggcttttt    1680 aactcatccg tttgccaatc attgcaaaca actgaaatgt ggatgtgatt gcctcaataa    1740
agctcgtccc cattgcttaa gccttcaaaa aaaaaaaaaa aaaaaaaaaa aaaaaaaaaa    1800
aaaaa                                                                1805

<210> SEQ ID NO 27
<211> LENGTH: 2094
<212> TYPE: DNA
<213> ORGANISM: Homo sapiens

<400> SEQUENCE: 27
aaatgaaaga gggagcagga ggcgccggtc ccagccacct cccaaggtcc ctggctcagc      60
tctgacaccc cagtcccggc ccagggtga gtggggttgg gtggcggttt aggggcacca     120
ggggcgtgtg gggacctgtg taagtgtggg gtggggagga tctcaggaga tgtggaggct     180
ggaggcacag gaggccaggg aggagggaga agcctggtgc cgcactccca ccacgctggg     240
gtaggagggc agggacacct ccgacaaagg accctgtgag agttatgaaa gcggagttgc     300
ctctgtacca gccccccacc ctgagaggag ttcactgcag taaaaatggt gagagaaatg     360
gtgggccaag aaaggagtgg tctcgctgcc tctgccactc ccactcctcc catgggcacc     420
aaattgggtc tagcgtctcg ggttcgaggc tccactcttc ccacagcatc cttgacagct     480
aagggcaccg ctgggtttcc gcttccgaaa ccagccaagt caggggctgg tccagctgat     540
ctccaaggtc cttcctaaga atctgggatc tggaggatcc cagggtcgaa cggagacggc     600 tcaggggggtg cggctaaaat gcaaatgggg gatcctcccc agcacccatc ggtcccaaag     660
agaaggtaac ccatagctga gcgtcgcctg ctcccctcgg gccctccgt ggccctccgt     720 ttcatactgg tctcatcgct aaacccgggc ctctcctacc tcacgactca ccctgaagtc     780
agagaaggtc caacggaccc cacccgata ggcttggaag gggcaggggt ccctgacttg     840
ccccatcccc tgactcccg ccccgcgtcc ccagcgccat gggggagtgg gcgttcctgg     900
gctcgctgct ggacgccgtg cagctgcagt cgccgctcgt gggccgcctc tggctggtgg     960
tcatgctgat cttccgcatc ctggtgctgg ccacggtggg cggcgccgtg ttcgaggacg    1020
agcaagagga gttcgtgtgc aacacgctgc agccgggctg tcgccagacc tgctacgacc    1080
gcgccttccc ggtctcccac taccgcttct ggctcttcca catcctgctg ctctcggcgc    1140
ccccggtgct gttcgtcgtc tactccatgc accgggcagg caaggaggcg ggcggcgctg    1200
aggcggcggc gcagtgcgcc cccggactgc ccgaggccca gtgcgcgccg tgcgccctgc    1260
gcgcccgccg cgcgcgccgc tgctacctgc tgagcgtggc gctgcgcctg ctggccgagc    1320
tgaccttcct gggcggccag gcgctgctct acggcttccg cgtggccccg cacttcgcgt    1380
gcgccggtcc gccctgcccg cacacggtcg actgcttcgt gagccggccc accgagaaga    1440
ccgtcttcgt gctcttctat ttcgcggtgg ggctgctgtg ggcgctgctc agcgtagccg    1500
agctgggcca cctgctctgg aagggccgcc cgcgcgccgg ggagcgtgac aaccgctgca    1560
accgtgcaca cgaagaggcg cagaagctgc tcccgccgcc gccgccgcca cctattgttg    1620
tcacttggga agaaaacaga caccttcaag gagagggctc cctggtagc ccccacccca    1680
```

-continued

| | |
|---|---|
| agacagagct ggatgcccct cgcttccgta gggaaagcac ttctcctgca ggatggcatt | 1740 |
| gctctctccc cttccatggc acgtagtatg tgctcagtaa atatgtgttg gatgagaaac | 1800 |
| tgaaggtgtc cccaggccta caccactgcc atgcccgaac actatccatg ctatggtggg | 1860 |
| caccatctct ctgatgacag ttctgtgtcc acaacccaga cccctccaca caaacccaga | 1920 |
| tggggctgtg ccgctgtttt ccagatgtat tcattcaaca aatatttgta gggtacctac | 1980 |
| tgtgtgtcag aagatgttca agatcagcat catccgatgg aaatagcata tgagccatgt | 2040 |
| atgtagtttc aagttttttca ttagccgcat taaaaaagta aaaggaaaca aatg | 2094 |

<210> SEQ ID NO 28
<211> LENGTH: 840
<212> TYPE: DNA
<213> ORGANISM: Homo sapiens
<400> SEQUENCE: 28

| | |
|---|---|
| atgtgtggca ggttcctgcg gcggctgctg gcggaggaga gccggcgctc caccccgtg | 60 |
| gggcgcctct tgcttcccgt gctcctggga ttccgccttg tgctgctggc tgccagtggg | 120 |
| cctggagtct atggtgatga gcagagtgaa ttcgtgtgtc acacccagca gccgggctgc | 180 |
| aaggctgcct gcttcgatgc cttccacccc ctctccccgc tgcgtttctg ggtcttccag | 240 |
| gtcatcttgg tggctgtacc cagcgccctc tatatggggtt tcactctgta tcacgtgatc | 300 |
| tggcactggg aattatcagg aaaggggaag gaggaggaga ccctgatcca gggacgggag | 360 |
| ggcaacacag atgtcccagg ggctggaagc ctcaggctgc tctgggctta tgtggctcag | 420 |
| ctggggctc ggcttgtcct ggaggggca gccctgggt tgcagtacca cctgtatggg | 480 |
| ttccagatgc ccagctcctt tgcatgtcgc cgagaacctt gccttggtag tataacctgc | 540 |
| aatctgtccc gcccctctga aagaccatt ttcctaaaga ccatgtttgg agtcagcggt | 600 |
| ttctgtctct tgtttacttt tttggagctt gtgcttctgg gtttggggag atggtggagg | 660 |
| acctggaagc acaaatcttc ctcttctaaa tacttcctaa cttcagagag caccagaaga | 720 |
| cacaagaaag caaccgatag cctcccagtg gtggaaacca agagcaatt tcaagaagca | 780 |
| gttccaggaa gaagcttagc ccaggaaaaa caaagaccag ttggacccag agatgcctga | 840 |

<210> SEQ ID NO 29
<211> LENGTH: 672
<212> TYPE: DNA
<213> ORGANISM: Homo sapiens
<400> SEQUENCE: 29

| | |
|---|---|
| atgagttgga tgttcctcag agatctcctg agtggagtaa ataaatactc cactgggact | 60 |
| ggatggattt ggctggctgt cgtgtttgtc ttccgtttgc tggtctacat ggtggcagca | 120 |
| gagcacatgt ggaaagatga gcagaaagag tttgagtgca acagtagaca gcccggttgc | 180 |
| aaaaatgtgt gttttgatga cttcttcccc atttcccaag tcagactttg ggccttacaa | 240 |
| ctgataatgg tctccacacc ttcacttctg gtggttttac atgtagccta tcatgagggt | 300 |
| agagagaaaa ggcacagaaa gaaactctat gtcagcccag gtacaatgga tgggggccta | 360 |
| tggtacgctt atcttatcag cctcattgtt aaaactggtt ttgaaattgg cttccttgtt | 420 |
| ttattttata agctatatga tggctttagt gttccctacc ttataaagtg tgatttgaag | 480 |
| ccttgtccca cactgtgga ctgcttcatc tccaaaccca ctgagaagac gatcttcatc | 540 |
| ctcttcttgg tcatcaccctc atgcttgtgt attgtgttga atttcattga actgagtttt | 600 |

| | |
|---|---|
| ttggttctca agtgctttat taagtgctgt ctccaaaaat atttaaaaaa acctcaagtc | 660 |
| ctcagtgtgt ga | 672 |

<210> SEQ ID NO 30
<211> LENGTH: 1113
<212> TYPE: DNA
<213> ORGANISM: Homo sapiens

<400> SEQUENCE: 30

| | |
|---|---|
| atggaaggcg tggacttgct agggtttctc atcatcacat taaactgcaa cgtgaccatg | 60 |
| gtaggaaagc tctggttcgt cctcacgatg ctgctgcgga tgctggtgat tgtcttggcg | 120 |
| gggcgacccg tctaccagga cgagcaggag aggtttgtct gcaacacgct gcagccggga | 180 |
| tgcgccaatg tttgctacga cgtcttctcc cccgtgtctc acctgcggtt ctggctgatc | 240 |
| cagggcgtgt gcgtcctcct ccccctccgcc gtcttcagcg tctatgtcct gcaccgagga | 300 |
| gccacgctcg ccgcgctggg ccccgccgc tgccccgacc ccgggagcc ggcctccggg | 360 |
| cagagacgct gcccgcggcc attcgggag cgcgcggcc tccaggtgcc cgacttttcg | 420 |
| gccggctaca tcatccacct cctcctccgg accctgctgg aggcagcctt cggggccttg | 480 |
| cactactttc tctttggatt cctggccccg aagaagttcc cttgcacgcg ccctccgtgc | 540 |
| acgggcgtgg tggactgcta cgtgtcgcgg cccacagaga agtccctgct gatgctgttc | 600 |
| ctctgggcgg tcagcgcgct gtcttttctg ctgggcctcg ccgacctggt ctgcagcctg | 660 |
| cggcggcgga tgcgcaggag gccgggaccc ccacaagcc cctccatccg gaagcagagc | 720 |
| ggagcctcag gccacgcgga gggacgccgg actgacgagg agggtgggcg ggaggaagag | 780 |
| ggggcaccgg cgcccccggg tgcacgcgcc ggaggggagg gggctggcag ccccaggcgt | 840 |
| acatccaggg tgtcagggca cacgaagatt ccggatgagg atgagagtga ggtgacatcc | 900 |
| tccgccagcg aaaagctggg cagacagccc cggggcaggc cccaccgaga ggccgcccag | 960 |
| gaccccaggg gctcaggatc cgaggagcag ccctcagcag cccccagccg cctggccgcg | 1020 |
| ccccccttcct gcagcagcct gcagccccct gacccgcctg ccagctccag tggtgctccc | 1080 |
| cacctgagag ccaggaagtc tgagtgggtg tga | 1113 |

<210> SEQ ID NO 31
<211> LENGTH: 1632
<212> TYPE: DNA
<213> ORGANISM: Homo sapiens

<400> SEQUENCE: 31

| | |
|---|---|
| atgggggact ggaacttatt gggtggcatc ctagaggaag ttcactccca ctcaaccata | 60 |
| gtggggaaaa tctggctgac catcctcttc atcttccgaa tgctggtact tcgtgtggct | 120 |
| gctgaggatg tctgggatga tgaacagtca gcatttgcct gcaacacccg gcagccaggt | 180 |
| tgcaacaata tctgttatga tgatgcattc cctatctctt tgatcaggtt ctgggtttta | 240 |
| cagatcatct ttgtgtcttc tccttctttg gtctatatgg ccatgcact ttataggctc | 300 |
| agggcctttg agaaagacag gcagaggaaa agtcacacc ttagagccca gatggagaat | 360 |
| ccagatcttg acttggagga gcagcaaaga atagataggg aactgaggag ttagaggag | 420 |
| cagaagagga tccataaagt ccctctgaaa ggatgtctgc tgcgtactta tgtcttacac | 480 |
| atcttgacca gatctgtgct ggaagtagga ttcatgatag ccaatatat tctctatggg | 540 |
| tttcaaatgc acccccttta caatgcact caacctcctt gccccaatgc ggtggattgc | 600 |
| tttgtatcca ggcccactga gaagacaatt ttcatgcttt ttatgcacag cattgcagcc | 660 |

-continued

```
atttccttgt tactcaatat actggaaata tttcatctag gcatcagaaa aattatgagg    720
acactttata agaaatccag cagtgagggc attgaggatg aaacaggccc tccattccat    780
ttgaagaaat attctgtggc ccagcagtgt atgatttgct cttcattgcc tgaaagaatc    840
tctccacttc aagctaacaa tcaacagcaa gtcattcgag ttaatgtgcc aaagtctaaa    900
accatgtggc aaatcccaca gccaaggcaa cttgaagtag acccttccaa tgggaaaaag    960
gactggtctg agaaggatca gcatagcgga cagctccatg ttcacagccc gtgtccctgg   1020
gctggcagtg ctggaaatca gcacctggga cagcaatcag accattcctc atttggcctg   1080
cagaatacaa tgtctcagtc ctggctaggt acaactacgg ctcctagaaa ctgtccatcc   1140
tttgcagtag gaacctggga gcagtcccag gacccagaac cctcaggtga gcctctcaca   1200
gatcttcata gtcactgcag agacagtgaa ggcagcatga gagagagtgg ggtctggata   1260
gacagatctc gcccaggcag tcgcaaggcc agctttctgt ccagattgtt gtctgaaaag   1320
cgacatctgc acagtgactc aggaagctct ggttctcgga atagctcctg cttggatttt   1380
cctcactggg aaaacagccc ctcacctctg ccttcagtca ctgggcacag aacatcaatg   1440
gtaagacagg cagccctacc gatcatggaa ctatcacaag agctgttcca ttctggatgc   1500 tttcttttc ctttctttct tcctggggtg tgtatgtatg tttgtgttga cagagaggca   1560
gatggagggg gagattattt atggagagat aaaattattc attcgataca ttcagttaaa   1620
ttcaattcat aa                                                       1632
```

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32

```
ccaaggcagg ctagctacaa cgatccagtc a                                    31
```

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33

```
ccgtgggagg ctagctacaa cgagtgagag g                                    31
```

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34

```
ccgtgggagg ctaactacaa cgagtgagag g                                    31
```

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
agtcttttgg gctagctaca acgatgggct ca                                     32

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tttggagagg ctagctacaa cgaccgcagt c                                      31

<210> SEQ ID NO 37
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tttggagagg ctaactacaa cgaccgcagt c                                      31

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
acgaggaagg ctagctacaa cgatgtttct g                                      31

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ttgcggcggc tagctacaac gacgaggaat                                        30

<210> SEQ ID NO 40
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ccatgcgagg ctagctacaa cgatttgctc t                                      31

<210> SEQ ID NO 41
<211> LENGTH: 31
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 41
ttggtccagg ctagctacaa cgagatggct a                                          31

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gtaattgcgg caggaggaat tgtttctgtc                                            30

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gacagaaaca attcctcctg ccgcaattac                                            30

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ccaaggcact ccagtcac                                                         18

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tccgtgggac gtgagagga                                                        19

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
agtcttttga tgggctca                                                         18

<210> SEQ ID NO 47
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 47
ttttggagat ccgcagtct                                                    19

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
cacgaggaat tgtttctgt                                                    19

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tttgcggcac gaggaatt                                                     18

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
cccatgcgat tttgctctg                                                    19

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gttggtccac gatggctaa                                                    19

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gttgcagagg ctagctacaa cgaaaaatcg g                                      31

<210> SEQ ID NO 53
<211> LENGTH: 31
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 53
gttctttagg ctagctacaa cgactctccc t                                        31

<210> SEQ ID NO 54
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gtccttaaag gctagctaca acgatcgttc ttt                                      33

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tctcttcgag gctagctaca acgagtcctt aaa                                      33

<210> SEQ ID NO 56
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tctcttcgag gctaactaca acgagtcctt aaa                                      33

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gatacggagg ctagctacaa cgacttctgg g                                        31

<210> SEQ ID NO 58
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
cttcgatagg ctagctacaa cgaggacctt c                                        31

<210> SEQ ID NO 59
<211> LENGTH: 31
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 59
cttcgatagg ctaactacaa cgaggacctt c                                    31

<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ggtgaagagg ctagctacaa cgaagtcttt tct                                  33

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ccttaaactc gttctttatc tctcccttca                                      30

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
acttccctct ctatttcttg ctcaaattcc                                      30

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tacggacctt ctgggttttg atctcttcga                                      30

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
agcttctcta gttttgggtc ttccaggcat                                      30

<210> SEQ ID NO 65
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 65
gtaattgcgg caggaggaat tgtttctgtc                                        30

<210> SEQ ID NO 66
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ggctagctac aacga                                                        15

<210> SEQ ID NO 67
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ggctaactac aacga                                                        15
```